(12) United States Patent
Janusz

(10) Patent No.: US 12,187,715 B2
(45) Date of Patent: *Jan. 7, 2025

(54) SMALL MOLECULE ACTIVATORS OF TIE-2

(71) Applicant: EyePoint Pharmaceuticals, Inc., Watertown, MA (US)

(72) Inventor: John M. Janusz, West Chester, OH (US)

(73) Assignee: EYEPOINT PHARMACEUTICALS, INC., Watertown, MA (US)

( * ) Notice: Subject to any disclaimer, the term of this patent is extended or adjusted under 35 U.S.C. 154(b) by 39 days.

This patent is subject to a terminal disclaimer.

(21) Appl. No.: 18/169,496

(22) Filed: Feb. 15, 2023

(65) Prior Publication Data

US 2023/0265087 A1     Aug. 24, 2023

Related U.S. Application Data

(63) Continuation of application No. 17/082,612, filed on Oct. 28, 2020, now Pat. No. 11,613,534.

(60) Provisional application No. 62/927,233, filed on Oct. 29, 2019.

(51) Int. Cl.
    *C07D 417/04*     (2006.01)

(52) U.S. Cl.
    CPC ................ *C07D 417/04* (2013.01)

(58) Field of Classification Search
    CPC .................................... C07D 417/04
    USPC ...................................... 514/365
    See application file for complete search history.

(56) References Cited

U.S. PATENT DOCUMENTS

| | | |
|---|---|---|
| 953,924 A | 4/1910 | Schweimler |
| 7,589,212 B2 | 9/2009 | Gray |
| 7,622,593 B2 | 11/2009 | Gray |
| 7,795,444 B2 | 9/2010 | Gray |
| 8,106,078 B2 | 1/2012 | Gray et al. |
| 8,188,125 B2 | 5/2012 | Gray et al. |
| 8,258,311 B2 | 9/2012 | Gray et al. |
| 8,329,916 B2 | 12/2012 | Amarsinghe et al. |
| 8,338,615 B2 | 12/2012 | Gray et al. |
| 8,569,348 B2 | 10/2013 | Shalwitz et al. |
| 8,846,685 B2 | 9/2014 | Gray et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,284,285 B2 | 3/2016 | Gray et al. |
| 9,440,963 B2 | 9/2016 | Peters et al. |
| 9,539,245 B2 | 1/2017 | Peters |
| RE46,592 E | 10/2017 | Gray et al. |
| 9,795,594 B2 | 10/2017 | Gray et al. |
| 9,949,956 B2 | 4/2018 | Shalwitz et al. |
| 9,994,560 B2 | 6/2018 | Janusz et al. |
| 10,220,048 B2 | 3/2019 | Peters et al. |
| 10,463,650 B2 | 11/2019 | Gray et al. |
| 10,858,354 B2 | 12/2020 | Janusz et al. |
| 11,613,534 B2 * | 3/2023 | Janusz ............. C07D 277/28 514/365 |
| 2011/0236922 A1 | 9/2011 | Burns |
| 2013/0023543 A1 | 1/2013 | Gray et al. |
| 2016/0038467 A1 | 2/2016 | Peters |
| 2017/0079959 A1 | 3/2017 | Peters |
| 2018/0016245 A1 | 1/2018 | Shalwitz et al. |

FOREIGN PATENT DOCUMENTS

| | | |
|---|---|---|
| WO | WO-9622997 A1 | 8/1996 |
| WO | WO-2015138882 A1 | 9/2015 |

OTHER PUBLICATIONS

International Search Report and Written Opinion for International Application No. PCT/US2020/057641, Commissioner for Patents, United States, mailed on Jan. 28, 2021.

\* cited by examiner

*Primary Examiner* — Kahsay Habte

(74) *Attorney, Agent, or Firm* — Sterne, Kessler, Goldstein & Fox P.L.L.C.

(57) ABSTRACT

Disclosed herein are compounds effective for activation of Tie-2 and inhibition of HPTP-beta. The compounds can provide effective therapy for vascular disorders that can include, for example, retinopathies, ocular edema, and ocular neovascularization.

22 Claims, 4 Drawing Sheets

SMALL MOLECULE ACTIVATORS OF TIE-2

CROSS REFERENCE TO RELATED APPLICATIONS

This application is a continuation of U.S. patent application Ser. No. 17/082,612, filed Oct. 28, 2020, which claims priority to U.S. Provisional Application No. 62/927,233, filed Oct. 29, 2019, each of which is incorporated by reference herein in its entirety.

BACKGROUND

The human vascular system is an organ system responsible for the delivery of nutrients and removal of waste products from tissues, and the maintenance of homeostasis throughout the body. Tie-2 is a transmembrane tyrosine-protein kinase receptor expressed in the vascular endothelium that regulates vascular stability. Disease states associated with the deactivation of Tie-2 include vascular inflammation and leakage, pathologic neovascularization, and angiogenesis.

INCORPORATION BY REFERENCE

Each patent, publication, and non-patent literature cited in the application is hereby incorporated by reference in its entirety as if each was incorporated by reference individually.

SUMMARY

In some embodiments, the invention provides a compound of the formula:

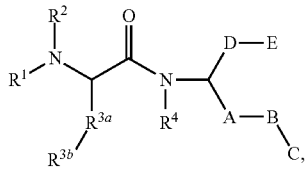

wherein:
A is alkylene that is unsubstituted or substituted, or a bond;
B is substituted or unsubstituted cycloalkylene, substituted or unsubstituted heterocycloalkylene, substituted arylene, substituted or unsubstituted heteroarylene that contains a sulfur atom as a ring member, or substituted or unsubstituted heteroarylene in which two ring members are heteroatoms and all other ring members of the heteroaryl are carbon atoms;
C is heterocycloalkyl, aryl, heteroaryl, alkyl, or cycloalkyl, any of which is unsubstituted or substituted, or hydrogen;
D is alkylene that is unsubstituted or substituted, or a bond;
E is cycloalkyl, heterocycloalkyl, aryl, or heteroaryl, any of which is unsubstituted or substituted;
$R^1$ is hydrogen, an acyl group, an alkoxycarbonyl group, an amidine group, or an amide group;
$R^2$ is alkyl, alkenyl, alkynyl, cycloalkyl, or cycloalkenyl, any of which is unsubstituted or substituted, or hydrogen;
$R^{3a}$ is alkylene that is unsubstituted or substituted, or a bond;
$R^{3b}$ is alkyl, alkenyl, alkynyl, cycloalkyl, cycloalkenyl, heterocycloalkyl, aryl, or heteroaryl, any of which is unsubstituted or substituted, or hydrogen; and
$R^4$ is alkyl, alkenyl, alkynyl, cycloalkyl, or cycloalkenyl, any of which is unsubstituted or substituted, or hydrogen;
wherein at least one of $R^2$ and $R^4$ is not hydrogen, or a pharmaceutically-acceptable salt or zwitterion thereof.

In some embodiments, the invention provides a compound that activates Tie-2, wherein the compound that activates Tie-2 comprises a carbamate linkage of a secondary amine.

In some embodiments, the invention provides a compound that activates Tie-2, wherein the compound that activates Tie-2 comprises an amide linkage of a secondary amine and a carbamate linkage of a primary amine.

In some embodiments, the invention provides a compound that activates Tie-2, wherein the compound that activates Tie-2 comprises an amide linkage of a secondary amine and a carbamate linkage of another secondary amine.

In some embodiments, the invention provides a Tie-2 activator, wherein the Tie-2 activator has a solubility in water of at least 30 mg/mL at about 23° C.

DETAILED DESCRIPTION

Figure 1:
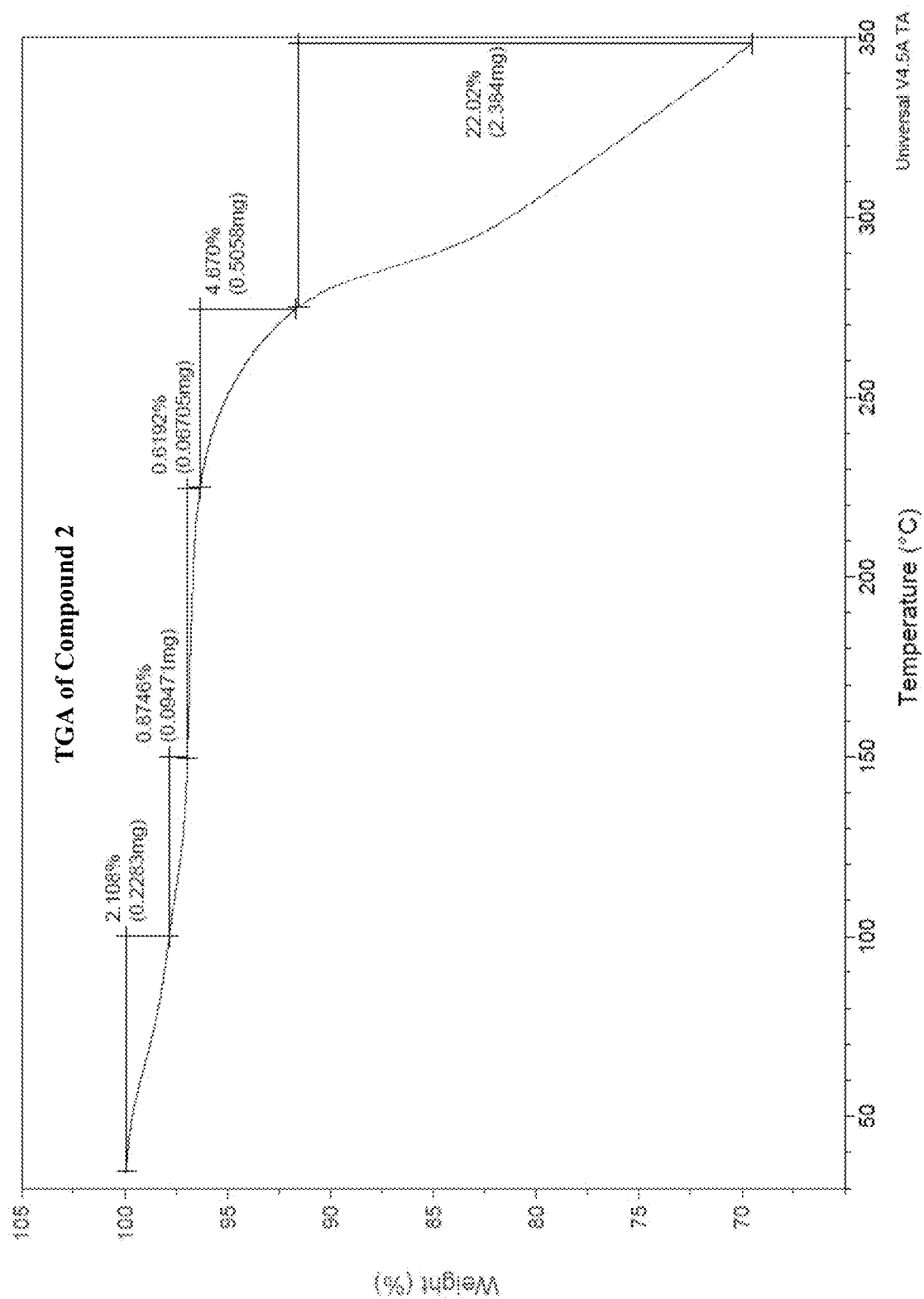
FIG. 1 illustrates the thermogravimetric analysis (TGA) thermogram of Compound 2.

Described herein are compounds that can activate Tie-2. A Tie-2 activator of the disclosure can activate Tie-2 signaling by promoting protein phosphorylation, such as phosphorylation of the Tie-2 protein.

Tie-2 (tyrosine kinase with immunoglobulin and epidermal growth factor homology domains 2) is a membrane receptor tyrosine kinase expressed primarily in vascular endothelial cells and a subset of hematopoietic stem cells (HSCs) and macrophages. The principal regulators of Tie-2 phosphorylation are angiopoietin 1 (Ang-1) and angiopoietin 2 (Ang-2). Ang-1 is an agonist of Tie-2, and binding of Ang-1 to Tie-2 promotes receptor phosphorylation. Ang-2 is a Tie-2 ligand that acts in a context-dependent antagonistic or agonistic manner. Binding of Ang-1 to Tie-2 increases the level of endogenous Tie-2 receptor phosphorylation and initiates downstream AKT signaling. This binding initiates a signaling cascade that can induce distinctive vascular remodeling through highly organized angiogenesis and tightening of the endothelial cell junctions (endothelium cell proximity). Within the vascular endothelium, Ang-1-Tie-2 signaling promotes endothelial cell proximity. In the HSC microenvironment, Ang-1-Tie-2 signaling contributes in a paracrine manner to the long-term repopulation of HSCs.

Under physiological conditions, the duration of Tie-2 phosphorylation is regulated by the human protein tyrosine phosphatase beta (often abbreviated as HPTPβ or HPTP beta), which removes the phosphate from the Tie-2 receptor.

By inhibiting HPTPβ, the level of Tie-2 phosphorylation substantially increases, restoring proper cell proximity. HPTPβ plays a functional role in endothelial cell proliferation, viability, differentiation, vasculogenesis, and angiogenesis. HPTPβ and vascular endothelial protein tyrosine phosphatase (VE-PTP; the mouse orthologue of HPTPβ) are expressed in vascular endothelial cells throughout development. A small molecule of the disclosure can activate Tie-2 downstream signaling by inhibiting HPTPβ/VE-PTP.

Compounds that activate Tie-2 can treat disorders and injuries associated with vascular instability, which include, for example, nephropathy, acute kidney injury, cancer, systemic vascular leak syndromes including acute lung injury (ALI) and acute respiratory distress syndrome (ARDS), hypertension including hypertensive crisis/urgency, pulmonary artery hypertension, hepatorenal syndrome, cerebrovascular leakage, and brain edema.

Compounds that activate Tie-2 can treat disorders of the vascular networks of the eye that include, for example, retinopathies, ocular edema, and ocular neovascularization. Non-limiting examples of diseases or conditions that involve retinopathy, ocular edema, or neovascularization can include, for example, diabetic macular edema, age-related macular degeneration (wet form), choroidal neovascularization, diabetic retinopathy, retinal vein occlusion (central or branch), ocular trauma, surgery induced edema, surgery induced neovascularization, cystoid macular edema, ocular ischemia, and uveitis. These diseases or conditions are characterized by changes in the ocular vasculature whether progressive or non-progressive, whether a result of an acute disease or condition, or a chronic disease or condition.

Compounds that activate Tie-2 can also treat disorders related to the impairment of aqueous humor outflow from the anterior chamber of the eye, which can include, for example, glaucoma, primary glaucoma, pseudoexfoliative glaucoma, pigmentary glaucoma, primary juvenile glaucoma, open angle glaucoma, wide-angle glaucoma, close-angle glaucoma, congenital glaucoma, acquired glaucoma, secondary glaucoma, inflammatory glaucoma, phacogenic glaucoma, or neovascular glaucoma. In some cases, a Tie-2 activator of the disclosure can stabilize vasculature associated with the trabecular meshwork, reducing intraocular pressure and treating ocular hypertension.

A compound of the disclosure can exhibit increased aqueous solubility and physical stability in solution relative to other Tie-2 activators. The presence of tertiary amide or tertiary carbamate functionality in the compounds disclosed herein can increase aqueous solubility and solution stability. The solubility of a therapeutic compound, or the ability of a compound to dissolve in a solvent to afford a homogeneous system, can be a principal factor in the ability of the compound to be absorbed and dispersed to the target site of therapy. Increased solubility and a faster rate of dissolution of a therapeutic compound can decrease the dosage required to achieve an efficacious outcome. Additionally, the stability of a compound in solution, or the ability of the compound to maintain a homogenous state over time, can contribute to enhanced shelf life.

Tie-2 Activators.

Compounds disclosed herein can be effective as Tie-2 activators. The compounds can promote Tie-2 activation, for example, by binding to or inhibiting HPTPβ. Such compounds can bind to HPTPβ, for example, by mimicking the binding mechanism of a native substrate, such as a phosphorylated compound. A compound can be a phosphate mimetic or bioisostere, for example, a sulfamic acid. The compound could also be derived from an amino acid building block or comprise an amino acid backbone for efficiency and economy of synthesis.

In some embodiments, the disclosure provides a compound that activates Tie-2, wherein the compound that activates Tie-2 comprises an amide linkage of a secondary amine.

In some embodiments, the disclosure provides a compound that inhibits HPTPβ, wherein the compound that activates Tie-2 comprises an amide linkage of a secondary amine.

In some embodiments, the disclosure provides a compound that activates Tie-2, wherein the compound that activates Tie-2 comprises a carbamate linkage of a secondary amine.

In some embodiments, the disclosure provides a compound that inhibits HPTPβ, wherein the compound that activates Tie-2 comprises a carbamate linkage of a secondary amine.

In some embodiments, the disclosure provides a compound that activates Tie-2, wherein the compound that activates Tie-2 comprises an amide linkage of a secondary amine and a carbamate linkage of another secondary amine.

In some embodiments, the disclosure provides a compound that inhibits HPTPβ, wherein the compound that inhibits HPTPβ comprises an amide linkage of a secondary amine and a carbamate linkage of another secondary amine.

In some embodiments, the disclosure provides a congener of a compound that activates Tie-2, wherein the congener of the compound that activates Tie-2 is alkylated on a heteroatom, wherein the compound that activates Tie-2 is not alkylated on a heteroatom that corresponds to the heteroatom that is alkylated in the congener of the compound that activates Tie-2.

In some embodiments, the congener is more soluble in water than is the compound that activates Tie-2 under the same experimental conditions, for example, temperature or pressure.

In some embodiments, the disclosure provides a congener of a compound that inhibits HPTPβ, wherein the congener of the compound that inhibits HPTPβ is alkylated on a heteroatom, wherein the compound that inhibits HPTPβ is not alkylated on a heteroatom that corresponds to the heteroatom that is alkylated in the congener of the compound that inhibits HPTPβ.

In some embodiments, the congener is more soluble in water than is the compound that activates HPTPβ under the same experimental conditions, for example, temperature or pressure. In some embodiments, the disclosure provides a Tie-2 activator that has a solubility in water of at least 30 mg/mL at about 23° C., at least 40 mg/mL at about 23° C., at least 50 mg/mL at about 23° C., at least 60 mg/mL at about 23° C., at least 70 mg/mL at about 23° C., at least 80 mg/mL at about 23° C., at least 90 mg/mL at about 23° C., at least 100 mg/mL at about 23° C., at least 110 mg/mL at about 23° C., at least 120 mg/mL at about 23° C., at least 130 mg/mL at about 23° C., at least 140 mg/mL at about 23° C., at least 150 mg/mL at about 23° C., at least 160 mg/mL at about 23° C., at least 170 mg/mL at about 23° C., at least 180 mg/mL at about 23° C., at least 190 mg/mL at about 23° C., at least 200 mg/mL at about 23° C., at least 210 mg/mL at about 23° C., at least 220 mg/mL at about 23° C., at least 230 mg/mL at about 23° C., at least 240 mg/mL at about 23° C., or at least 250 mg/mL at about 23° C.

In some embodiments, the Tie-2 activator has a molecular weight of no greater than 50,000 Da. In some embodiments, the Tie-2 activator has a molecular weight of no greater than 45,000 Da. In some embodiments, the Tie-2 activator has a molecular weight of no greater than 40,000 Da. In some embodiments, the Tie-2 activator has a molecular weight of no greater than 35,000 Da. In some embodiments, the Tie-2 activator has a molecular weight of no greater than 30,000 Da. In some embodiments, the Tie-2 activator has a molecular weight of no greater than 25,000 Da. In some embodiments, the Tie-2 activator has a molecular weight of no greater than 20,000 Da. In some embodiments, the Tie-2 activator has a molecular weight of no greater than 15,000 Da. In some embodiments, the Tie-2 activator has a molecular weight of no greater than 10,000 Da. In some embodiments, the Tie-2 activator has a molecular weight of no greater than 5,000 Da. In some embodiments, the Tie-2 activator has a molecular weight of no greater than 2,500 Da. In some embodiments, the Tie-2 activator has a molecular weight of no greater than 2,000 Da. In some embodiments, the Tie-2 activator has a molecular weight of no greater than 1,500 Da. In some embodiments, the Tie-2 activator has a molecular weight of no greater than 1,000 Da. In some embodiments, the Tie-2 activator has a molecular weight of no greater than 800 Da. In some embodiments, the Tie-2 activator has a molecular weight of no greater than 750 Da. In some embodiments, the Tie-2 activator has a molecular weight of no greater than 700 Da. In some embodiments, the Tie-2 activator has a molecular weight of no greater than 650 Da. In some embodiments, the Tie-2 activator has a molecular weight of no greater than 625 Da.

In some embodiments, the Tie-2 activator has a molecular weight of at least 200 Da. In some embodiments, the Tie-2 activator has a molecular weight of at least 300 Da. In some embodiments, the Tie-2 activator has a molecular weight of at least 400 Da. In some embodiments, the Tie-2 activator has a molecular weight of at least 450 Da. In some embodiments, the Tie-2 activator has a molecular weight of at least 500 Da. In some embodiments, the Tie-2 activator has a molecular weight of at least 550 Da. In some embodiments, the Tie-2 activator has a molecular weight of at least 560 Da. In some embodiments, the Tie-2 activator has a molecular weight of at least 570 Da. In some embodiments, the Tie-2 activator has a molecular weight of at least 580 Da. In some embodiments, the Tie-2 activator has a molecular weight of at least 590 Da. In some embodiments, the Tie-2 activator has a molecular weight of at least 600 Da.

In some embodiments, the Tie-2 activator has a molecular weight that is 450 Da to 700 Da, 450 Da to 650 Da, 450 Da to 625 Da, 450 Da to 600 Da, 450 Da to 575 Da, 450 Da to 550 Da, 475 Da to 700 Da, 475 Da to 650 Da, 475 Da to 625 Da, 475 Da to 600 Da, 475 Da to 575 Da, 475 Da to 550 Da, 500 Da to 700 Da, 500 Da to 650 Da, 500 Da to 625 Da, 500 Da to 600 Da, 500 Da to 575 Da, 500 Da to 550 Da, 525 Da to 700 Da, 525 Da to 650 Da, 525 Da to 625 Da, 525 Da to 600 Da, 525 Da to 575 Da, 525 Da to 550 Da, 550 Da to 700 Da, 550 Da to 650 Da, 550 Da to 625 Da, 550 Da to 600 Da, 550 Da to 575 Da, 575 Da to 700 Da, 575 Da to 650 Da, 575 Da to 625 Da, 575 Da to 600 Da, 600 Da to 700 Da, 600 Da to 650 Da, or 600 Da to 625 Da.

In some embodiments, a compound of the disclosure is a compound of the formula:

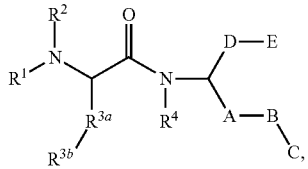

or a pharmaceutically-acceptable salt or zwitterion thereof, wherein: A is alkylene that is unsubstituted or substituted, or a bond; B is substituted or unsubstituted cycloalkylene, substituted or unsubstituted heterocycloalkylene, substituted arylene, substituted or unsubstituted heteroarylene that contains a sulfur atom as a ring member, or substituted or unsubstituted heteroarylene in which two ring members are heteroatoms and all other ring members of the heteroaryl are carbon atoms; C is cycloalkyl, heterocycloalkyl, aryl, heteroaryl, or alkyl, any of which is unsubstituted or substituted, or hydrogen; D is alkylene that is unsubstituted or substituted, or a bond; E is cycloalkyl, heterocycloalkyl, aryl, or heteroaryl, any of which is unsubstituted or substituted; $R^1$ is hydrogen, an acyl group, an alkoxycarbonyl group, an amidine group, or an amide group; $R^2$ is alkyl, alkenyl, alkynyl, cycloalkyl, or cycloalkenyl, any of which is unsubstituted or substituted, or hydrogen; $R^{3a}$ is alkylene that is unsubstituted or substituted, or a bond; $R^{3b}$ is alkyl, alkenyl, alkynyl, cycloalkyl, cycloalkenyl, heterocycloalkyl, aryl, or heteroaryl, any of which is unsubstituted or substituted, or hydrogen; and $R^4$ is alkyl, alkenyl, alkynyl, cycloalkyl, or cycloalkenyl, any of which is unsubstituted or substituted, or hydrogen, wherein at least one of $R^2$ and $R^4$ is not hydrogen.

In some embodiments, A is alkylene. In some embodiments, A is methylene, ethylene, or propylene. In some embodiments, A is a bond. In some embodiments, B is heteroarylene that contains a sulfur atom as a ring member. In some embodiments, B is heteroarylene that contains a sulfur atom as a ring member, and is substituted. In some embodiments, B is heteroarylene in which two ring members are heteroatoms and all other ring members of the heteroaryl are carbon atoms. In some embodiments, B is heteroarylene in which two ring members are heteroatoms and all other ring members of the heteroaryl are carbon atoms, and is substituted. In some embodiments, B is a 2-substituted-thiazol-4-yl group. In some embodiments, B is a 4-substituted-thiazol-2-yl group. In some embodiments, C is aryl. In some embodiments, C is phenyl that is unsubstituted or unsubstituted. In some embodiments, C is heteroaryl. In some embodiments, C is heteroaryl that is unsubstituted or substituted. In some embodiments, C is alkyl. In some embodiments, C is methyl, ethyl, propyl, butyl, isopropyl, isobutyl, or tert-butyl, any of which is unsubstituted or substituted. In some embodiments, C is aryl. In some embodiments, C is phenyl. In some embodiments, C is a thiophenyl group. In some embodiments, C is a thiophen-2-yl group. In some embodiments, C is a thiophen-3-yl group. In some embodiments, C is hydrogen. In some embodiments, D is alkylene. In some embodiments, D is methylene, ethylene, or propylene. In some embodiments, D is methylene. In some embodiments, D is a bond. In some embodiments, E is aryl. In some embodiments, E is phenyl. In some embodiments, E is substituted phenyl. In some embodiments, E is 2-substituted-phenyl. In some embodiments, E is 3-substituted-phenyl. In some embodiments, E is 4-substituted-phenyl. In some embodiments, E is 2-phenylsulfamic acid, 3-phenylsulfamic acid, or 4-phenylsulfamic acid, 2-phenylsulfonic acid, 3-phenylsulfonic acid, or 4-phenylsulfonic acid, 2-methanesulfonylphenyl, 3-methanesulfonylphenyl, 4-methanesulfonylphenyl, 2-toluenesulfonylphenyl, 3-toluenesulfonylphenyl, or 4-toluenesulfonylphenyl. In some embodiments, $R^1$ is hydrogen. In some embodiments, $R^1$ is an acyl group. In some embodiments, $R^1$ is acetyl, propionyl, or butyryl. In some embodiments, $R^1$ is an alkoxycarbonyl group. In some embodiments, $R^1$ is a methoxycarbonyl group. In some embodiments, $R^1$ is an ethoxycarbonyl group. In some embodiments, $R^1$ is a propyloxycarbonyl group. In some embodiments, $R^1$ is a butyloxycarbonyl group. In some embodiments, $R^1$ is an isopropyloxycarbonyl group. In some embodiments, $R^1$ is a tert-butyloxycarbonyl group. In some embodiments, $R^2$ is hydrogen. In some embodiments, $R^2$ is not hydrogen. In some embodiments, $R^2$ is alkyl. In some embodiments, $R^2$ is methyl, ethyl, propyl, or butyl. In some embodiments, $R^2$ is methyl. In some embodiments, $R^{3a}$ is alkylene. In some embodiments, $R^{3a}$ is methylene. In some embodiments, $R^{3a}$ is ethylene. In some embodiments, $R^{3a}$ is propylene. In some embodiments, $R^{3b}$ is aryl. In some embodiments, $R^{3b}$ is phenyl. In some embodiments, $R^4$ is hydrogen. In some embodiments, $R^4$ is not hydrogen. In some embodiments, $R^4$ is alkyl. In some embodiments, $R^4$ is methyl, ethyl, propyl, or butyl. In some embodiments, $R^4$ is methyl. In some embodiments, both $R^2$ and $R^4$ are not hydrogen. In some embodiments, both $R^2$ and $R^4$ are alkyl. In some embodiments, both $R^2$ and $R^4$ are methyl. In some embodiments, $R^2$ is hydrogen and $R^4$ is alkyl. In some embodiments, $R^2$ is hydrogen and $R^4$ is methyl. In some embodiments, $R^2$ is alkyl and $R^4$ is hydrogen. In some embodiments, $R^2$ is methyl and $R^4$ is hydrogen.

In some embodiments, A is a bond; B is heteroarylene that contains a sulfur atom as a ring member, or heteroarylene in which two ring members are heteroatoms and all other ring members of the heteroaryl are carbon atoms, any of which is unsubstituted or substituted; C is aryl, heteroaryl, alkyl, or cycloalkyl; D is alkylene; E is aryl or heteroaryl; $R^1$ is an acyl group or an alkoxycarbonyl group; $R^2$ is alkyl or hydrogen; $R^{3a}$ is alkylene; $R^{3b}$ is aryl or heteroaryl; and $R^4$ is alkyl or hydrogen, wherein at least one of $R^2$ and $R^4$ is alkyl.

In some embodiments, A is a bond; B is heteroarylene that contains a sulfur atom as a ring member, or heteroarylene in which two ring members are heteroatoms and all other ring members of the heteroaryl are carbon atoms, any of which is unsubstituted or substituted; C is heteroaryl; D is alkylene; E is aryl; $R^1$ is an alkoxycarbonyl group; $R^2$ is alkyl or hydrogen; $R^{3a}$ is alkylene; $R^{3b}$ is aryl or heteroaryl; and $R^4$ is alkyl or hydrogen, wherein at least one of $R^2$ and $R^4$ is alkyl.

In some embodiments, A is a bond; B is a thiazole group; C is heteroaryl; D is methylene; E is aryl; $R^1$ is an alkoxycarbonyl group; $R^2$ is alkyl or hydrogen; $R^{3a}$ is methylene; $R^{3b}$ is aryl; and $R^4$ is alkyl or hydrogen, wherein at least one of $R^2$ and $R^4$ is alkyl.

In some embodiments, A is a bond; B is a 2-substituted-thiazol-4-yl group or a 4-substituted-thiazol-2-yl group; C is heteroaryl; D is methylene; E is 4-substituted phenyl; $R^1$ is an alkoxycarbonyl group; $R^2$ is alkyl or hydrogen; $R^{3a}$ is methylene; $R^{3b}$ is phenyl; and $R^4$ is alkyl or hydrogen, wherein at least one of $R^2$ and $R^4$ is alkyl.

In some embodiments, A is a bond; B is a 2-substituted-thiazol-4-yl group or a 4-substituted-thiazol-2-yl group; C is a thiophenyl group; D is methylene; E is 4-substituted phenyl; $R^1$ is an alkoxycarbonyl group; $R^2$ is alkyl or hydrogen; $R^{3a}$ is methylene; $R^{3b}$ is phenyl; and $R^4$ is alkyl or hydrogen, wherein at least one of $R^2$ and $R^4$ is alkyl.

In some embodiments, A is a bond; B is a 2-substituted-thiazol-4-yl group or a 4-substituted-thiazol-2-yl group; C is a thiophen-2-yl group; D is methylene; E is 4-substituted phenyl; $R^1$ is an alkoxycarbonyl group; $R^2$ is alkyl or hydrogen; $R^{3a}$ is methylene; $R^{3b}$ is phenyl; and $R^4$ is alkyl or hydrogen, wherein at least one of $R^2$ and $R^4$ is alkyl.

In some embodiments, A is a bond; B is a 2-substituted-thiazol-4-yl group or a 4-substituted-thiazol-2-yl group; C is a thiophen-2-yl group; D is methylene; E is 4-substituted phenyl; $R^1$ is a methoxycarbonyl group; $R^2$ is alkyl or hydrogen; $R^{3a}$ is methylene; $R^{3b}$ is phenyl; and $R^4$ is alkyl or hydrogen, wherein at least one of $R^2$ and $R^4$ is alkyl.

In some embodiments, A is a bond; B is a 2-substituted-thiazol-4-yl group or a 4-substituted-thiazol-2-yl group; C is a thiophen-2-yl group; D is methylene; E is 4-substituted phenyl; $R^1$ is a methoxycarbonyl group; $R^2$ is methyl or hydrogen; $R^{3a}$ is methylene; $R^{3b}$ is phenyl; and $R^4$ is methyl or hydrogen, wherein at least one of $R^2$ and $R^4$ is methyl.

In some embodiments, A is a bond; B is a 2-substituted-thiazol-4-yl group or a 4-substituted-thiazol-2-yl group; C is a thiophen-2-yl group; D is methylene; E is 4-substituted phenyl; $R^1$ is a methoxycarbonyl group; $R^2$ is methyl; $R^{3a}$ is methylene; $R^{3b}$ is phenyl; and $R^4$ is methyl.

In some embodiments, A is a bond; B is a 2-substituted-thiazol-4-yl group or a 4-substituted-thiazol-2-yl group; C is a thiophen-2-yl group; D is methylene; E is 4-substituted phenyl; $R^1$ is a methoxycarbonyl group; $R^2$ is hydrogen; $R^{3a}$ is methylene; $R^{3b}$ is phenyl; and $R^4$ is methyl.

In some embodiments, A is a bond; B is a 2-substituted-thiazol-4-yl group or a 4-substituted-thiazol-2-yl group; C is a thiophen-2-yl group; D is methylene; E is 4-substituted phenyl; $R^1$ is a methoxycarbonyl group; $R^2$ is methyl; $R^{3a}$ is methylene; $R^{3b}$ is phenyl; and $R^4$ is hydrogen.

In some embodiments, A is a bond; B is a 2-substituted-thiazol-4-yl group or a 4-substituted-thiazol-2-yl group; C is a thiophen-2-yl group; D is methylene; $R^1$ is a methoxycarbonyl group; $R^2$ is methyl or hydrogen; $R^{3a}$ is methylene; $R^{3b}$ is phenyl; $R^4$ is methyl or hydrogen; and E is

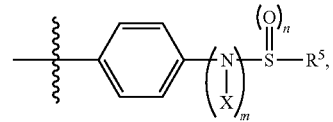

wherein X is methyl or hydrogen; m is 0 or 1; n is 0, 1, or 2; $R^5$ is hydrogen, hydroxyl, methyl, ethyl, phenyl, para-toluyl, N-piperidinyl, N-piperazinyl, N-pyrrolidinyl, $OR^6$, or $N(R^6)_2$, wherein each $R^6$ is hydrogen, methyl, ethyl, n-propyl, i-propyl, or n-butyl, wherein at least one of $R^2$ and $R^4$ is methyl. In some embodiments, X is hydrogen; m is 1; n is 2; and $R^5$ is hydroxyl, wherein at least one of $R^2$ and $R^4$ is methyl.

In some embodiments, a compound of the disclosure is a compound of the formula:

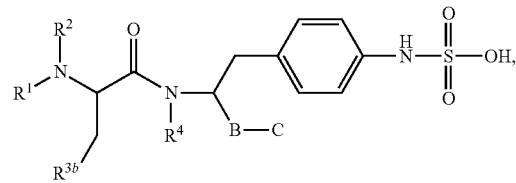

or a pharmaceutically-acceptable salt or zwitterion thereof, wherein: B is cycloalkylene, heterocycloalkylene, arylene, heteroarylene that contains a sulfur atom as a ring member, or heteroarylene in which two ring members are heteroatoms and all other ring members of the heteroaryl are carbon atoms, any of which is unsubstituted or substituted; C is cycloalkyl, heterocycloalkyl, aryl, heteroaryl, or alkyl, any of which is unsubstituted or substituted, or hydrogen; $R^1$ is hydrogen, an acyl group, an alkoxycarbonyl group, an amidine group, or an amide group; $R^2$ is alkyl, alkenyl, alkynyl, cycloalkyl, or cycloalkenyl, any of which is unsubstituted or substituted, or hydrogen; $R^{3b}$ is alkyl, alkenyl, alkynyl, cycloalkyl, cycloalkenyl, heterocycloalkyl, aryl, or heteroaryl, any of which is unsubstituted or substituted, or hydrogen; and $R^4$ is alkyl, alkenyl, alkynyl, cycloalkyl, or cycloalkenyl, any of which is unsubstituted or substituted, or hydrogen, wherein at least one of $R^2$ and $R^4$ is not hydrogen.

In some embodiments, B is heteroarylene that contains a sulfur atom as a ring member. In some embodiments, B is heteroarylene that contains a sulfur atom as a ring member, and is substituted. In some embodiments, B is heteroarylene in which two ring members are heteroatoms and all other ring members of the heteroaryl are carbon atoms. In some embodiments, B is heteroarylene in which two ring members are heteroatoms and all other ring members of the heteroaryl are carbon atoms, and is substituted. In some embodiments, B is a 2-substituted-thiazol-4-yl group. In some embodiments, B is a 4-substituted-thiazol-2-yl group. In some embodiments, C is aryl. In some embodiments, C is phenyl that is unsubstituted or unsubstituted. In some embodiments, C is heteroaryl. In some embodiments, C is heteroaryl that is unsubstituted or substituted. In some embodiments, C is alkyl. In some embodiments, C is methyl, ethyl, propyl, butyl, isopropyl, isobutyl, or tert-butyl, any of which is unsubstituted or substituted. In some embodiments, C is aryl. In some embodiments, C is phenyl. In some embodiments, C is a thiophenyl group. In some embodiments, C is a thiophen-2-yl group. In some embodiments, C is a thiophen-3-yl group. In some embodiments, C is hydrogen. In some embodiments, $R^1$ is hydrogen. In some embodiments, $R^1$ is an acyl group. In some embodiments, $R^1$ is acetyl, propionyl, or butyryl. In some embodiments, $R^1$ is an alkoxycarbonyl group. In some embodiments, $R^1$ is a methoxycarbonyl group. In some embodiments, $R^1$ is an ethoxycarbonyl group. In some embodiments, $R^1$ is a propyloxycarbonyl group. In some embodiments, $R^1$ is a butyloxycarbonyl group. In some embodiments, $R^1$ is an isopropyloxycarbonyl group. In some embodiments, $R^1$ is a tert-butyloxycarbonyl group. In some embodiments, $R^2$ is hydrogen. In some embodiments, $R^2$ is not hydrogen. In some embodiments, $R^2$ is alkyl. In some embodiments, $R^2$ is methyl, ethyl, propyl, or butyl. In some embodiments, $R^2$ is methyl. In some embodiments, $R^{3b}$ is aryl. In some embodiments, $R^{3b}$ is phenyl. In some embodiments, $R^4$ is hydrogen. In some embodiments, $R^4$ is not hydrogen. In some embodiments, $R^4$ is alkyl. In some embodiments, $R^4$ is methyl, ethyl, propyl, or butyl. In some embodiments, $R^4$ is methyl. In some embodiments, both $R^2$ and $R^4$ are not hydrogen. In some embodiments, both $R^2$ and $R^4$ are alkyl. In some embodiments, both $R^2$ and $R^4$ are methyl. In some embodiments, $R^2$ is hydrogen and $R^4$ is alkyl. In some embodiments, $R^2$ is hydrogen and $R^4$ is methyl. In some embodiments, $R^2$ is alkyl and $R^4$ is hydrogen. In some embodiments, $R^2$ is methyl and $R^4$ is hydrogen.

In some embodiments, B is heteroarylene that contains a sulfur atom as a ring member, or heteroarylene in which two ring members are heteroatoms and all other ring members of the heteroaryl are carbon atoms, any of which is unsubstituted or substituted; C is aryl, heteroaryl, alkyl, or cycloalkyl; $R^1$ is an acyl group or an alkoxycarbonyl group; $R^2$ is alkyl or hydrogen; $R^{3b}$ is aryl or heteroaryl; and $R^4$ is alkyl or hydrogen, wherein at least one of $R^2$ and $R^4$ is alkyl.

In some embodiments, B is heteroarylene that contains a sulfur atom as a ring member, or heteroarylene in which two ring members are heteroatoms and all other ring members of the heteroaryl are carbon atoms, any of which is unsubstituted or substituted; C is heteroaryl; $R^1$ is an alkoxycarbonyl group; $R^2$ is alkyl or hydrogen; $R^{3b}$ is aryl or heteroaryl; and $R^4$ is alkyl or hydrogen, wherein at least one of $R^2$ and $R^4$ is alkyl.

In some embodiments, B is a thiazole group; C is heteroaryl; $R^1$ is an alkoxycarbonyl group; $R^2$ is alkyl or hydrogen; $R^{3b}$ is aryl; and $R^4$ is alkyl or hydrogen, wherein at least one of $R^2$ and $R^4$ is alkyl.

In some embodiments, B is a 2-substituted-thiazol-4-yl group or a 4-substituted-thiazol-2-yl group; C is heteroaryl; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl.

In some embodiments, B is a 2-substituted-thiazol-4-yl group or a 4-substituted-thiazol-2-yl group; C is a thiophenyl group; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl.

In some embodiments, B is a 2-substituted-thiazol-4-yl group or a 4-substituted-thiazol-2-yl group; C is a thiophen-2-yl group; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl.

In some embodiments, B is a 2-substituted-thiazol-4-yl group or a 4-substituted-thiazol-2-yl group; C is a thiophen-2-yl group; $R^1$ is a methoxycarbonyl group; $R^2$ is alkyl or hydrogen; $R^{3b}$ is phenyl; and $R^4$ is alkyl or hydrogen, wherein at least one of $R^2$ and $R^4$ is alkyl.

In some embodiments, B is a 2-substituted-thiazol-4-yl group or a 4-substituted-thiazol-2-yl group; C is a thiophen-2-yl group; $R^1$ is a methoxycarbonyl group; $R^2$ is methyl or hydrogen; $R^{3b}$ is phenyl; and $R^4$ is methyl or hydrogen, wherein at least one of $R^2$ and $R^4$ is methyl.

In some embodiments, B is a 2-substituted-thiazol-4-yl group or a 4-substituted-thiazol-2-yl group; C is a thiophen-2-yl group; $R^1$ is a methoxycarbonyl group; $R^2$ is methyl; $R^{3b}$ is phenyl; and $R^4$ is methyl.

In some embodiments, B is a 2-substituted-thiazol-4-yl group or a 4-substituted-thiazol-2-yl group; C is a thiophen-2-yl group; $R^1$ is a methoxycarbonyl group; $R^2$ is hydrogen; $R^{3b}$ is phenyl; and $R^4$ is methyl.

In some embodiments, B is a 2-substituted-thiazol-4-yl group or a 4-substituted-thiazol-2-yl group; C is a thiophen-2-yl group; $R^1$ is a methoxycarbonyl group; $R^2$ is methyl; $R^{3b}$ is phenyl; and $R^4$ is hydrogen.

In some embodiments, a compound of the disclosure is a compound of the formula:

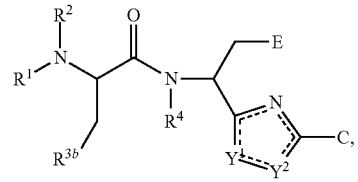

or a pharmaceutically-acceptable salt or zwitterion thereof, wherein: C is cycloalkyl, heterocycloalkyl, aryl, heteroaryl, or alkyl, any of which is unsubstituted or substituted, or hydrogen; E is cycloalkyl, heterocycloalkyl, aryl, or heteroaryl, any of which is unsubstituted or substituted; $R^1$ is hydrogen, an acyl group, an alkoxycarbonyl group, an amide group, or an amidine group; $R^2$ is alkyl, alkenyl, alkynyl, cycloalkyl, or cycloalkenyl, any of which is unsubstituted or substituted, or hydrogen; $R^{3b}$ is alkyl, alkenyl, alkynyl, cycloalkyl, cycloalkenyl, heterocycloalkyl, aryl, or heteroaryl, any of which is unsubstituted or substituted, or hydrogen; $R^4$ is alkyl, alkenyl, alkynyl, cycloalkyl, or cycloalkenyl, any of which is unsubstituted or substituted, or hydrogen; $Y^1$ is S or CH; $Y^2$ is S or CH; and each ===== is chosen to provide a six-electron system, wherein one of $Y^1$ and $Y^2$ is S, and wherein at least of $R^2$ and $R^4$ is not hydrogen.

In some embodiments, C is aryl. In some embodiments, C is phenyl that is unsubstituted or unsubstituted. In some embodiments, C is heteroaryl. In some embodiments, C is heteroaryl that is unsubstituted or substituted. In some embodiments, C is alkyl. In some embodiments, C is methyl, ethyl, propyl, butyl, isopropyl, isobutyl, or tert-butyl, any of which is unsubstituted or substituted. In some embodiments, C is phenyl. In some embodiments, C is a thiophenyl group. In some embodiments, C is a thiophen-2-yl group. In some embodiments, C is a thiophen-3-yl group. In some embodiments, C is hydrogen. In some embodiments, E is aryl. In some embodiments, E is phenyl. In some embodiments, E is substituted phenyl. In some embodiments, E is 2-substituted-phenyl. In some embodiments, E is 3-substituted-phenyl. In some embodiments, E is 4-substituted-phenyl. In some embodiments, E is 2-phenylsulfamic acid, 3-phenylsulfamic acid, or 4-phenylsulfamic acid, 2-phenylsulfonic acid, 3-phenylsulfonic acid, or 4-phenylsulfonic acid, 2-methanesulfonylphenyl, 3-methanesulfonylphenyl, 4-methanesulfonylphenyl, 2-toluenesulfonylphenyl, 3-toluenesulfonylphenyl, or 4-toluenesulfonylphenyl. In some embodiments, $R^1$ is hydrogen. In some embodiments, $R^1$ is an acyl group. In some embodiments, $R^1$ is acetyl, propionyl, or butyryl. In some embodiments, $R^1$ is an alkoxycarbonyl group. In some embodiments, $R^1$ is a methoxycarbonyl group. In some embodiments, $R^1$ is an ethoxycarbonyl group. In some embodiments, $R^1$ is a propyloxycarbonyl group. In some embodiments, $R^1$ is a butyloxycarbonyl group. In some embodiments, $R^1$ is an isopropyloxycarbonyl group. In some embodiments, $R^1$ is a tert-butyloxycarbonyl group. In some embodiments, $R^2$ is hydrogen. In some embodiments, $R^2$ is not hydrogen. In some embodiments, $R^2$ is alkyl. In some embodiments, $R^2$ is methyl, ethyl, propyl, or butyl. In some embodiments, $R^2$ is methyl. In some embodiments, $R^{3b}$ is aryl. In some embodiments, $R^{3b}$ is phenyl. In some embodiments, $R^4$ is hydrogen. In some embodiments, $R^4$ is not hydrogen. In some embodiments, $R^4$ is alkyl. In some embodiments, $R^4$ is methyl, ethyl, propyl, or butyl. In some embodiments, $R^4$ is methyl. In some embodiments, both $R^2$ and $R^4$ are not hydrogen. In some embodiments, both $R^2$ and $R^4$ are alkyl. In some embodiments, both $R^2$ and $R^4$ are methyl. In some embodiments, $R^2$ is hydrogen and $R^4$ is alkyl. In some embodiments, $R^2$ is hydrogen and $R^4$ is methyl. In some embodiments, $R^2$ is alkyl and $R^4$ is hydrogen. In some embodiments, $R^2$ is methyl and $R^4$ is hydrogen. In some embodiments, $Y^1$ is S and $Y^2$ and CH. In some embodiments, $Y^2$ is S and $Y^1$ and CH.

In some embodiments, C is aryl, heteroaryl, alkyl, or cycloalkyl; E is aryl or heteroaryl; $R^1$ is an acyl group or an alkoxycarbonyl group; $R^2$ is alkyl or hydrogen; $R^{3b}$ is aryl or heteroaryl; and $R^4$ is alkyl or hydrogen, wherein at least one of $R^2$ and $R^4$ is alkyl. In some embodiments, $Y^2$ is S and $Y^1$ and CH.

In some embodiments, C is heteroaryl; E is aryl; $R^1$ is an alkoxycarbonyl group; $R^2$ is alkyl or hydrogen; $R^{3b}$ is aryl or heteroaryl; and $R^4$ is alkyl or hydrogen, wherein at least one of $R^2$ and $R^4$ is alkyl. In some embodiments, $Y^2$ is S and $Y^1$ and CH.

In some embodiments, C is heteroaryl; E is aryl; $R^1$ is an alkoxycarbonyl group; $R^2$ is alkyl or hydrogen; $R^{3b}$ is aryl; and $R^4$ is alkyl or hydrogen, wherein at least one of $R^2$ and $R^4$ is alkyl. In some embodiments, $Y^2$ is S and $Y^1$ and CH.

In some embodiments, C is heteroaryl; E is 4-substituted phenyl; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl. In some embodiments, $Y^2$ is S and $Y^1$ and CH.

In some embodiments, C is a thiophenyl group; E is 4-substituted phenyl; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl. In some embodiments, $Y^2$ is S and $Y^1$ and CH.

In some embodiments, C is a thiophen-2-yl group; E is 4-substituted phenyl; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl. In some embodiments, $Y^2$ is S and $Y^1$ and CH.

In some embodiments, C is a thiophen-2-yl group; E is 4-substituted phenyl; $R^1$ is a methoxycarbonyl group; $R^2$ is alkyl or hydrogen; $R^{3b}$ is phenyl; and $R^4$ is alkyl or hydrogen, wherein at least one of $R^2$ and $R^4$ is alkyl. In some embodiments, $Y^2$ is S and $Y^1$ and CH.

In some embodiments, C is a thiophen-2-yl group; E is 4-substituted phenyl; $R^1$ is a methoxycarbonyl group; $R^2$ is methyl or hydrogen; $R^{3b}$ is phenyl; and $R^4$ is methyl or hydrogen, wherein at least one of $R^2$ and $R^4$ is methyl. In some embodiments, $Y^2$ is S and $Y^1$ and CH.

In some embodiments, C is a thiophen-2-yl group; E is 4-substituted phenyl; $R^1$ is a methoxycarbonyl group; $R^2$ is methyl; $R^{3b}$ is phenyl; and $R^4$ is methyl. In some embodiments, $Y^2$ is S and $Y^1$ and CH.

In some embodiments, C is a thiophen-2-yl group; E is 4-substituted phenyl; $R^1$ is a methoxycarbonyl group; $R^2$ is hydrogen; $R^{3b}$ is phenyl; and $R^4$ is methyl. In some embodiments, $Y^2$ is S and $Y^1$ and CH.

In some embodiments, C is a thiophen-2-yl group; E is 4-substituted phenyl; $R^1$ is a methoxycarbonyl group; $R^2$ is methyl; $R^{3b}$ is phenyl; and $R^4$ is hydrogen. In some embodiments, $Y^2$ is S and $Y^1$ and CH.

In some embodiments, a compound of the disclosure is a compound of the formula:

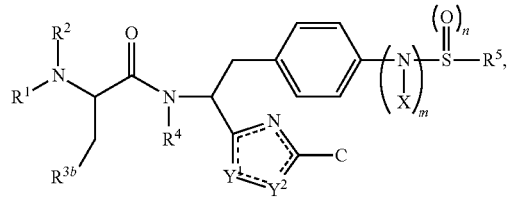

or a pharmaceutically-acceptable salt or zwitterion thereof, wherein: C is heterocycloalkyl, aryl, heteroaryl, alkyl, or cycloalkyl, any of which is unsubstituted or substituted, or hydrogen; $R^1$ is hydrogen, an acyl group, an alkoxycarbonyl group, an amidine group, or an amide group; $R^2$ is alkyl, alkenyl, alkynyl, cycloalkyl, or cycloalkenyl, any of which is unsubstituted or substituted, or hydrogen; $R^{3b}$ is alkyl, alkenyl, alkynyl, cycloalkyl, cycloalkenyl, heterocycloalkyl, aryl, or heteroaryl, any of which is unsubstituted or substituted, or hydrogen; $R^4$ is alkyl, alkenyl, alkynyl, cycloalkyl, or cycloalkenyl, any of which is unsubstituted or substituted, or hydrogen; $R^5$ is hydrogen, hydroxyl, methyl, ethyl, phenyl, or para-toluyl; X is methyl or hydrogen; m is 0 or 1; n is 0, 1, or 2; $Y^1$ is S or CH; $Y^2$ is S or CH; and each ═════ is chosen to provide a six-electron system, wherein one of $Y^1$ and $Y^2$ is S, and wherein at least one of $R^2$ and $R^4$ is not hydrogen.

In some embodiments, C is aryl. In some embodiments, C is phenyl that is unsubstituted or unsubstituted. In some embodiments, C is heteroaryl. In some embodiments, C is heteroaryl that is unsubstituted or substituted. In some embodiments, C is alkyl. In some embodiments, C is methyl, ethyl, propyl, butyl, isopropyl, isobutyl, or tert-butyl, any of which is unsubstituted or substituted. In some embodiments, C is aryl. In some embodiments, C is phenyl. In some embodiments, C is a thiophenyl group. In some embodiments, C is a thiophen-2-yl group. In some embodiments, C is a thiophen-3-yl group. In some embodiments, C is hydrogen. In some embodiments, $R^1$ is hydrogen. In some embodiments, $R^1$ is an acyl group. In some embodiments, $R^1$ is acetyl, propionyl, or butyryl. In some embodiments, $R^1$ is an alkoxycarbonyl group. In some embodiments, $R^1$ is a methoxycarbonyl group. In some embodiments, $R^1$ is an ethoxycarbonyl group. In some embodiments, $R^1$ is a propyloxycarbonyl group. In some embodiments, $R^1$ is a butyloxycarbonyl group. In some embodiments, $R^1$ is an isopropyloxycarbonyl group. In some embodiments, $R^1$ is a tert-butyloxycarbonyl group. In some embodiments, $R^2$ is hydrogen. In some embodiments, $R^2$ is not hydrogen. In some embodiments, $R^2$ is alkyl. In some embodiments, $R^2$ is methyl, ethyl, propyl, or butyl. In some embodiments, $R^2$ is methyl. In some embodiments, $R^{3b}$ is aryl. In some embodiments, $R^{3b}$ is phenyl. In some embodiments, $R^4$ is hydrogen. In some embodiments, $R^4$ is not hydrogen. In some embodiments, $R^4$ is alkyl. In some embodiments, $R^4$ is methyl, ethyl, propyl, or butyl. In some embodiments, $R^4$ is methyl. In some embodiments, both $R^2$ and $R^4$ are not hydrogen. In some embodiments, both $R^2$ and $R^4$ are alkyl. In some embodiments, both $R^2$ and $R^4$ are methyl. In some embodiments, $R^2$ is hydrogen and $R^4$ is alkyl. In some embodiments, $R^2$ is hydrogen and $R^4$ is methyl. In some embodiments, $R^2$ is alkyl and $R^4$ is hydrogen. In some embodiments, $R^2$ is methyl and $R^4$ is hydrogen. In some embodiments, $Y^1$ is S and $Y^2$ and CH. In some embodiments, $Y^2$ is S and $Y^1$ and CH. In some embodiments, $R^5$ is hydrogen, hydroxyl, methyl, ethyl, phenyl, or para-toluyl. In some embodiments, $R^5$ is hydroxyl. In some embodiments, X is hydrogen. In some embodiments, m is 1. In some embodiments, n is 2.

In some embodiments, C is aryl, heteroaryl, alkyl, or cycloalkyl; $R^1$ is an acyl group or an alkoxycarbonyl group; $R^2$ is alkyl or hydrogen; $R^{3b}$ is aryl or heteroaryl; $R^4$ is alkyl or hydrogen, wherein at least one of $R^2$ and $R^4$ is alkyl; $R^5$ is hydroxyl; X is hydrogen; m is 1; and n is 2. In some embodiments, $Y^2$ is S and $Y^1$ and CH.

In some embodiments, C is heteroaryl; $R^1$ is an alkoxycarbonyl group; $R^2$ is alkyl or hydrogen; $R^{3b}$ is aryl or heteroaryl; $R^4$ is alkyl or hydrogen, wherein at least one of $R^2$ and $R^4$ is alkyl; $R^5$ is hydroxyl; X is hydrogen; m is 1; and n is 2. In some embodiments, $Y^2$ is S and $Y^1$ and CH.

In some embodiments, C is heteroaryl; $R^1$ is an alkoxycarbonyl group; $R^2$ is alkyl or hydrogen; $R^{3b}$ is aryl; $R^4$ is alkyl or hydrogen, wherein at least one of $R^2$ and $R^4$ is alkyl; $R^5$ is hydroxyl; X is hydrogen; m is 1; and n is 2. In some embodiments, $Y^2$ is S and $Y^1$ and CH.

In some embodiments, C is heteroaryl; $R^1$ is an alkoxycarbonyl group; $R^2$ is alkyl or hydrogen; $R^{3b}$ is phenyl; $R^4$ is alkyl or hydrogen, wherein at least one of $R^2$ and $R^4$ is alkyl; $R^5$ is hydroxyl; X is hydrogen; m is 1; and n is 2. In some embodiments, $Y^2$ is S and $Y^1$ and CH.

In some embodiments, C is a thiophenyl group; $R^1$ is an alkoxycarbonyl group; $R^2$ is alkyl or hydrogen; $R^{3b}$ is phenyl; $R^4$ is alkyl or hydrogen, wherein at least one of $R^2$ and $R^4$ is alkyl; $R^5$ is hydroxyl; X is hydrogen; m is 1; and n is 2. In some embodiments, $Y^2$ is S and $Y^1$ and CH.

In some embodiments, C is a thiophen-2-yl group; $R^1$ is an alkoxycarbonyl group; $R^2$ is alkyl or hydrogen; $R^{3b}$ is phenyl; $R^4$ is alkyl or hydrogen, wherein at least one of $R^2$ and $R^4$ is alkyl; $R^5$ is hydroxyl; X is hydrogen; m is 1; and n is 2. In some embodiments, $Y^2$ is S and $Y^1$ and CH.

In some embodiments, C is a thiophen-2-yl group; $R^1$ is a methoxycarbonyl group; $R^2$ is alkyl or hydrogen; $R^{3b}$ is phenyl; $R^4$ is alkyl or hydrogen, wherein at least one of $R^2$ and $R^4$ is alkyl; $R^5$ is hydroxyl; X is hydrogen; m is 1; and n is 2. In some embodiments, $Y^2$ is S and $Y^1$ and CH.

In some embodiments, C is a thiophen-2-yl group; $R^1$ is a methoxycarbonyl group; $R^2$ is methyl or hydrogen; $R^{3b}$ is phenyl; $R^4$ is methyl or hydrogen, wherein at least one of $R^2$ and $R^4$ is methyl; $R^5$ is hydroxyl; X is hydrogen; m is 1; and n is 2. In some embodiments, $Y^2$ is S and $Y^1$ and CH.

In some embodiments, C is a thiophen-2-yl group; $R^1$ is a methoxycarbonyl group; $R^2$ is methyl; $R^{3b}$ is phenyl; $R^4$ is methyl; $R^5$ is hydroxyl; X is hydrogen; m is 1; and n is 2. In some embodiments, $Y^2$ is S and $Y^1$ and CH.

In some embodiments, C is a thiophen-2-yl group; $R^1$ is a methoxycarbonyl group; $R^2$ is hydrogen; $R^{3b}$ is phenyl; $R^4$ is methyl; $R^5$ is hydroxyl; X is hydrogen; m is 1; and n is 2. In some embodiments, $Y^2$ is S and $Y^1$ and CH.

In some embodiments, C is a thiophen-2-yl group; $R^1$ is a methoxycarbonyl group; $R^2$ is methyl; $R^{3b}$ is phenyl; $R^4$ is hydrogen; $R^5$ is hydroxyl; X is hydrogen; m is 1; and n is 2. In some embodiments, $Y^2$ is S and $Y^1$ and CH.

In some embodiments, a compound of the disclosure is a compound of the formula:

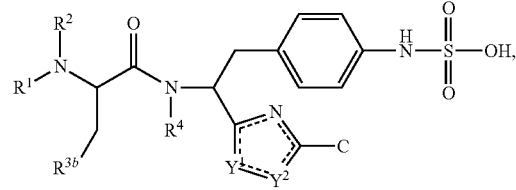

or a pharmaceutically-acceptable salt or zwitterion thereof, wherein: C is heterocycloalkyl, aryl, heteroaryl, alkyl, or cycloalkyl, any of which is unsubstituted or substituted, or hydrogen; $R^1$ is hydrogen, an acyl group, an alkoxycarbonyl group, an amide group, or an amidine group; $R^2$ is alkyl, alkenyl, alkynyl, cycloalkyl, or cycloalkenyl, any of which is unsubstituted or substituted, or hydrogen; $R^{3b}$ is alkyl, alkenyl, alkynyl, cycloalkyl, cycloalkenyl, heterocycloalkyl, aryl, or heteroaryl, any of which is unsubstituted or substituted, or hydrogen; $R^4$ is alkyl, alkenyl, alkynyl, cycloalkyl, or cycloalkenyl, any of which is unsubstituted or substituted, or hydrogen; $Y^1$ is S or CH; $Y^2$ is S or CH; and each ═════ is chosen to provide a six-electron system, wherein one of $Y^1$ and $Y^2$ is S, and wherein at least one of $R^2$ and $R^4$ is not hydrogen.

In some embodiments, C is aryl. In some embodiments, C is phenyl that is unsubstituted or unsubstituted. In some embodiments, C is heteroaryl. In some embodiments, C is heteroaryl that is unsubstituted or substituted. In some embodiments, C is alkyl. In some embodiments, C is methyl, ethyl, propyl, butyl, isopropyl, isobutyl, or tert-butyl, any of which is unsubstituted or substituted. In some embodiments, C is phenyl. In some embodiments, C is a thiophenyl group. In some embodiments, C is a thiophen-2-yl group. In some embodiments, C is a thiophen-3-yl group. In some embodiments, C is hydrogen. In some embodiments, $R^1$ is hydrogen. In some embodiments, $R^1$ is an acyl group. In some embodiments, $R^1$ is acetyl, propionyl, or butyryl. In some embodiments, $R^1$ is an alkoxycarbonyl group. In some embodiments, $R^1$ is a methoxycarbonyl group. In some embodiments, $R^1$ is an ethoxycarbonyl group. In some embodiments, $R^1$ is a propyloxycarbonyl group. In some embodiments, $R^1$ is a butyloxycarbonyl group. In some embodiments, $R^1$ is an isopropyloxycarbonyl group. In some embodiments, $R^1$ is a tert-butyloxycarbonyl group. In some embodiments, $R^2$ is hydrogen. In some embodiments, $R^2$ is not hydrogen. In some embodiments, $R^2$ is alkyl. In some embodiments, $R^2$ is methyl, ethyl, propyl, or butyl. In some embodiments, $R^2$ is methyl. In some embodiments, $R^{3b}$ is aryl. In some embodiments, $R^{3b}$ is phenyl. In some embodiments, $R^4$ is hydrogen. In some embodiments, $R^4$ is not hydrogen. In some embodiments, $R^4$ is alkyl. In some embodiments, $R^4$ is methyl, ethyl, propyl, or butyl. In some embodiments, $R^4$ is methyl. In some embodiments, both $R^2$ and $R^4$ are not hydrogen. In some embodiments, both $R^2$ and $R^4$ are alkyl. In some embodiments, both $R^2$ and $R^4$ are methyl. In some embodiments, $R^2$ is hydrogen and $R^4$ is alkyl. In some embodiments, $R^2$ is hydrogen and $R^4$ is methyl. In some embodiments, $R^2$ is alkyl and $R^4$ is hydrogen. In some embodiments, $R^2$ is methyl and $R^4$ is hydrogen. In some embodiments, $Y^1$ is S and $Y^2$ and CH. In some embodiments, $Y^2$ is S and $Y^1$ and CH.

In some embodiments, C is aryl, heteroaryl, alkyl, or cycloalkyl; $R^1$ is an acyl group or an alkoxycarbonyl group; $R^2$ is alkyl or hydrogen; $R^{3b}$ is aryl or heteroaryl; and $R^4$ is alkyl or hydrogen, wherein at least one of $R^2$ and $R^4$ is alkyl. In some embodiments, $Y^2$ is S and $Y^1$ and CH.

In some embodiments, C is heteroaryl; $R^1$ is an alkoxycarbonyl group; $R^2$ is alkyl or hydrogen; $R^{3b}$ is aryl or heteroaryl; and $R^4$ is alkyl or hydrogen, wherein at least one of $R^2$ and $R^4$ is alkyl. In some embodiments, $Y^2$ is S and $Y^1$ and CH.

In some embodiments, C is heteroaryl; $R^1$ is an alkoxycarbonyl group; $R^2$ is alkyl or hydrogen; $R^{3b}$ is aryl; and $R^4$ is alkyl or hydrogen, wherein at least one of $R^2$ and $R^4$ is alkyl. In some embodiments, $Y^2$ is S and $Y^1$ and CH.

In some embodiments, C is heteroaryl; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl. In some embodiments, $Y^2$ is S and $Y^1$ and CH.

In some embodiments, C is a thiophenyl group; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl. In some embodiments, $Y^2$ is S and $Y^1$ and CH.

In some embodiments, C is a thiophen-2-yl group; $R^1$ is an alkoxycarbonyl group; $R^2$ is alkyl or hydrogen; $R^{3b}$ is phenyl; and $R^4$ is alkyl or hydrogen, wherein at least one of $R^2$ and $R^4$ is alkyl. In some embodiments, $Y^2$ is S and $Y^1$ and CH.

In some embodiments, C is a thiophen-2-yl group; $R^1$ is a methoxycarbonyl group; $R^2$ is alkyl or hydrogen; $R^{3b}$ is phenyl; and $R^4$ is alkyl or hydrogen, wherein at least one of $R^2$ and $R^4$ is alkyl. In some embodiments, $Y^2$ is S and $Y^1$ and CH.

In some embodiments, C is a thiophen-2-yl group; $R^1$ is a methoxycarbonyl group; $R^2$ is methyl or hydrogen; $R^{3b}$ is phenyl; and $R^4$ is methyl or hydrogen, wherein at least one of $R^2$ and $R^4$ is methyl. In some embodiments, $Y^2$ is S and $Y^1$ and CH.

In some embodiments, C is a thiophen-2-yl group; $R^1$ is a methoxycarbonyl group; $R^2$ is methyl; $R^{3b}$ is phenyl; and $R^4$ is methyl. In some embodiments, $Y^2$ is S and $Y^1$ and CH.

In some embodiments, C is a thiophen-2-yl group; $R^1$ is a methoxycarbonyl group; $R^2$ is hydrogen; $R^{3b}$ is phenyl; and $R^4$ is methyl. In some embodiments, $Y^2$ is S and $Y^1$ and CH.

In some embodiments, C is a thiophen-2-yl group; $R^1$ is a methoxycarbonyl group; $R^2$ is methyl; $R^{3b}$ is phenyl; and $R^4$ is hydrogen. In some embodiments, $Y^2$ is S and $Y^1$ and CH.

In some embodiments, a compound of the disclosure is a compound of the formula:

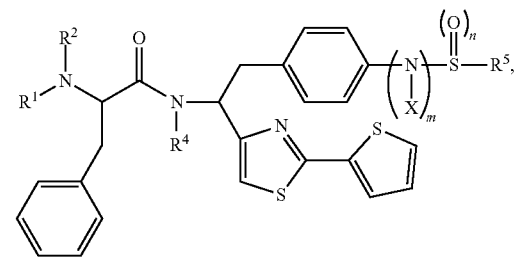

or a pharmaceutically-acceptable salt or zwitterion thereof, wherein: $R^1$ is hydrogen, an acyl group, an alkoxycarbonyl group, an amidine group, or an amide group; $R^2$ is alkyl, alkenyl, alkynyl, cycloalkyl, or cycloalkenyl, any of which is unsubstituted or substituted, or hydrogen; $R^4$ is alkyl, alkenyl, alkynyl, cycloalkyl, or cycloalkenyl, any of which is unsubstituted or substituted, or hydrogen; $R^5$ is hydrogen, hydroxyl, methyl, ethyl, phenyl, or para-toluyl; X is methyl or hydrogen; m is 0 or 1; and n is 0, 1, or 2, wherein at least one of $R^2$ and $R^4$ is not hydrogen.

In some embodiments, $R^1$ is hydrogen. In some embodiments, $R^1$ is an acyl group. In some embodiments, $R^1$ is acetyl, propionyl, or butyryl. In some embodiments, $R^1$ is an alkoxycarbonyl group. In some embodiments, $R^1$ is a methoxycarbonyl group. In some embodiments, $R^1$ is an ethoxycarbonyl group. In some embodiments, $R^1$ is a propyloxycarbonyl group. In some embodiments, $R^1$ is a butyloxycarbonyl group. In some embodiments, $R^1$ is an isopropyloxycarbonyl group. In some embodiments, $R^1$ is a tert-butyloxycarbonyl group. In some embodiments, $R^2$ is hydrogen. In some embodiments, $R^2$ is not hydrogen. In some embodiments, $R^2$ is alkyl. In some embodiments, $R^2$ is methyl, ethyl, propyl, or butyl. In some embodiments, $R^2$ is methyl. In some embodiments, $R^4$ is hydrogen. In some embodiments, $R^4$ is not hydrogen. In some embodiments, $R^4$ is alkyl. In some embodiments, $R^4$ is methyl, ethyl, propyl, or butyl. In some embodiments, $R^4$ is methyl. In some embodiments, both $R^2$ and $R^4$ are not hydrogen. In some embodiments, both $R^2$ and $R^4$ are alkyl. In some embodiments, both $R^2$ and $R^4$ are methyl. In some embodiments, $R^2$ is hydrogen and $R^4$ is alkyl. In some embodiments, $R^2$ is hydrogen and $R^4$ is methyl. In some embodiments, $R^2$ is alkyl and $R^4$ is hydrogen. In some embodiments, $R^2$ is methyl and $R^4$ is hydrogen. In some embodiments, $R^5$ is hydrogen, hydroxyl, methyl, ethyl, phenyl, or para-toluyl. In some embodiments, $R^5$ is hydroxyl. In some embodiments, X is hydrogen. In some embodiments, m is 1. In some embodiments, n is 2.

In some embodiments, $R^1$ is an acyl group or an alkoxycarbonyl group; $R^2$ is alkyl or hydrogen; $R^4$ is alkyl or hydrogen, wherein at least one of $R^2$ and $R^4$ is alkyl; $R^5$ is hydroxyl; X is hydrogen; m is 1; and n is 2.

In some embodiments, $R^1$ is an alkoxycarbonyl group; $R^2$ is alkyl or hydrogen; $R^4$ is alkyl or hydrogen, wherein at least one of $R^2$ and $R^4$ is alkyl; $R^5$ is hydroxyl; X is hydrogen; m is 1; and n is 2.

In some embodiments, $R^1$ is a methoxycarbonyl group; $R^2$ is alkyl or hydrogen; $R^4$ is alkyl or hydrogen, wherein at least one of $R^2$ and $R^4$ is alkyl; $R^5$ is hydroxyl; X is hydrogen; m is 1; and n is 2.

In some embodiments, $R^1$ is a methoxycarbonyl group; $R^2$ is methyl or hydrogen; $R^4$ is methyl or hydrogen, wherein at least one of $R^2$ and $R^4$ is methyl; $R^5$ is hydroxyl; X is hydrogen; m is 1; and n is 2.

In some embodiments, $R^1$ is a methoxycarbonyl group; $R^2$ is methyl; $R^4$ is methyl; $R^5$ is hydroxyl; X is hydrogen; m is 1; and n is 2.

In some embodiments, $R^1$ is a methoxycarbonyl group; $R^2$ is hydrogen; $R^4$ is methyl; $R^5$ is hydroxyl; X is hydrogen; m is 1; and n is 2.

In some embodiments, $R^1$ is a methoxycarbonyl group; $R^2$ is methyl; $R^4$ is hydrogen; $R^5$ is hydroxyl; X is hydrogen; m is 1; and n is 2.

In some embodiments, a compound of the disclosure is a compound of the formula:

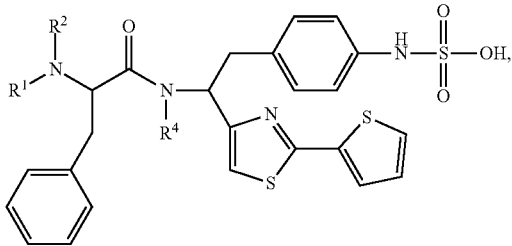

or a pharmaceutically-acceptable salt or zwitterion thereof, wherein: $R^1$ is hydrogen, an acyl group, an alkoxycarbonyl group, an amidine group, or an amide group; $R^2$ is alkyl, alkenyl, alkynyl, cycloalkyl, or cycloalkenyl, any of which is unsubstituted or substituted, or hydrogen; and $R^4$ is alkyl, alkenyl, alkynyl, cycloalkyl, or cycloalkenyl, any of which is unsubstituted or substituted, or hydrogen, wherein at least one of $R^2$ and $R^4$ is not hydrogen.

In some embodiments, $R^1$ is hydrogen. In some embodiments, $R^1$ is an acyl group. In some embodiments, $R^1$ is acetyl, propionyl, or butyryl. In some embodiments, $R^1$ is an alkoxycarbonyl group. In some embodiments, $R^1$ is a methoxycarbonyl group. In some embodiments, $R^1$ is an ethoxycarbonyl group. In some embodiments, $R^1$ is a propyloxycarbonyl group. In some embodiments, $R^1$ is a butyloxycarbonyl group. In some embodiments, $R^1$ is an isopropyloxycarbonyl group. In some embodiments, $R^1$ is a tert-butyloxycarbonyl group. In some embodiments, $R^2$ is hydrogen. In some embodiments, $R^2$ is not hydrogen. In some embodiments, $R^2$ is alkyl. In some embodiments, $R^2$ is methyl, ethyl, propyl, or butyl. In some embodiments, $R^2$ is methyl. In some embodiments, $R^4$ is hydrogen. In some embodiments, $R^4$ is not hydrogen. In some embodiments, $R^4$ is alkyl. In some embodiments, $R^4$ is methyl, ethyl, propyl, or butyl. In some embodiments, $R^4$ is methyl. In some embodiments, both $R^2$ and $R^4$ are not hydrogen. In some embodiments, both $R^2$ and $R^4$ are alkyl. In some embodiments, both $R^2$ and $R^4$ are methyl. In some embodiments, $R^2$ is hydrogen and $R^4$ is alkyl. In some embodiments, $R^2$ is hydrogen and $R^4$ is methyl. In some embodiments, $R^2$ is alkyl and $R^4$ is hydrogen. In some embodiments, $R^2$ is methyl and $R^4$ is hydrogen.

In some embodiments, $R^1$ is an acyl group or an alkoxycarbonyl group; $R^2$ is alkyl or hydrogen; and $R^4$ is alkyl or hydrogen, wherein at least one of $R^2$ and $R^4$ is alkyl.

In some embodiments, $R^1$ is an alkoxycarbonyl group; $R^2$ is alkyl or hydrogen; and $R^4$ is alkyl or hydrogen, wherein at least one of $R^2$ and $R^4$ is alkyl.

In some embodiments, $R^1$ is a methoxycarbonyl group; $R^2$ is alkyl or hydrogen; and $R^4$ is alkyl or hydrogen, wherein at least one of $R^2$ and $R^4$ is alkyl.

In some embodiments, $R^1$ is a methoxycarbonyl group; $R^2$ is methyl or hydrogen; and $R^4$ is methyl or hydrogen, wherein at least one of $R^2$ and $R^4$ is methyl.

In some embodiments, $R^1$ is a methoxycarbonyl group; $R^2$ is methyl; and $R^4$ is methyl.

In some embodiments, $R^1$ is a methoxycarbonyl group; $R^2$ is hydrogen; and $R^4$ is methyl.

In some embodiments, $R^1$ is a methoxycarbonyl group; $R^2$ is methyl; and $R^4$ is hydrogen.

In some embodiments, a compound of the disclosure is a compound of the formula:

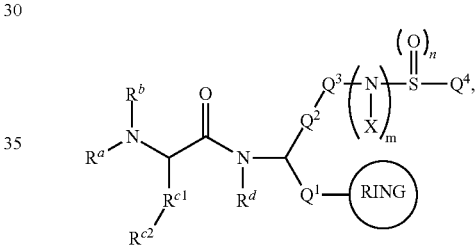

or a pharmaceutically-acceptable salt or zwitterion thereof, wherein: $Q^1$ is alkylene that is unsubstituted or substituted, or a bond; RING is a cyclic group that is unsubstituted or substituted; $Q^2$ is alkylene that is unsubstituted or substituted, or a bond; $Q^3$ is cycloalkyl, heterocycloalkyl, aryl, or heteroaryl, any of which is unsubstituted or substituted; $Q^4$ is hydrogen, hydroxyl, methyl, ethyl, phenyl, or para-toluyl; $R^a$ is hydrogen, an acyl group, an alkoxycarbonyl group, an amide group, or an amidine group; $R^b$ is alkyl, alkenyl, alkynyl, cycloalkyl, or cycloalkenyl, any of which is unsubstituted or substituted, or hydrogen; $R^{c1}$ is alkylene that is unsubstituted or substituted, or a bond; $R^{c2}$ is alkyl, alkenyl, alkynyl, cycloalkyl, cycloalkenyl, heterocycloalkyl, aryl, or heteroaryl, any of which is unsubstituted or substituted, or hydrogen; $R^d$ is alkyl, alkenyl, alkynyl, cycloalkyl, or cycloalkenyl, any of which is unsubstituted or substituted, or hydrogen; X is methyl or hydrogen; m is 0 or 1; and n is 0, 1, or 2, wherein at least one of $R^b$ and $R^d$ is not hydrogen.

In some embodiments, $Q^1$ is alkylene. In some embodiments, $Q^1$ is methylene, ethylene, or propylene. In some embodiments, $Q^1$ is a bond. In some embodiments, RING is a substituted cyclic group. In some embodiments, RING is cycloalkyl, heterocycloalkyl, aryl, or heteroaryl, any of which is unsubstituted or substituted. In some embodiments, RING is substituted heteroaryl. In some embodiments, RING is a 2-substituted-thiazol-4-yl group. In some embodiments, RING is a 4-substituted-thiazol-2-yl group. In some embodiments, RING is a 2-substituted-thiazol-4-yl group. In some embodiments, RING is a 4-substituted-thiazol-2-yl group. In some embodiments, RING is substituted with another cyclic group. In some embodiments, RING is substituted with an alkyl, cycloalkyl, heterocycloalkyl, aryl, or heteroaryl group, any of which is unsubstituted or substituted. In some embodiments, RING is substituted with a heteroaryl group. In some embodiments, RING is substituted with a thiophenyl group, a thiophen-2-yl group, or a thiophen-3-yl group. In some embodiments, RING is 2-(thiophen-2-yl)-thiazol-4-yl. In some embodiments, RING is 2-(thiophen-3-yl)-thiazol-4-yl. In some embodiments, RING is 4-(thiophen-2-yl)-thiazol-2-yl. In some embodiments, RING is 4-(thiophen-3-yl)-thiazol-2-yl. In some embodiments, $Q^2$ is alkylene. In some embodiments, $Q^2$ is methylene, ethylene, or propylene. In some embodiments, $Q^2$ is methylene. In some embodiments, $Q^2$ is a bond. In some embodiments, $Q^3$ is aryl. In some embodiments, $Q^3$ is phenyl. In some embodiments, $Q^3$ is substituted phenyl. In some embodiments, $Q^3$ is 2-substituted-phenyl. In some embodiments, $Q^3$ is 3-substituted-phenyl. In some embodiments, $Q^3$ is 4-substituted-phenyl. In some embodiments, $Q^4$ is hydrogen, hydroxyl, methyl, ethyl, phenyl, or para-toluyl. In some embodiments, $Q^4$ is hydroxyl. In some embodiments, $R^a$ is hydrogen. In some embodiments, $R^a$ is an acyl group. In some embodiments, $R^a$ is acetyl, propionyl, or butyryl. In some embodiments, $R^a$ is an alkoxycarbonyl group. In some embodiments, $R^a$ is a methoxycarbonyl group. In some embodiments, $R^a$ is an ethoxycarbonyl group. In some embodiments, $R^a$ is a propyloxycarbonyl group. In some embodiments, $R^a$ is a butyloxycarbonyl group. In some embodiments, $R^a$ is an isopropyloxycarbonyl group. In some embodiments, $R^a$ is a tert-butyloxycarbonyl group. In some embodiments, $R^b$ is hydrogen. In some embodiments, $R^b$ is not hydrogen. In some embodiments, $R^b$ is alkyl. In some embodiments, $R^b$ is methyl, ethyl, propyl, or butyl. In some embodiments, $R^b$ is methyl. In some embodiments, $R^{c1}$ is alkylene. In some embodiments, $R^{c1}$ is methylene. In some embodiments, $R^{c1}$ is ethylene. In some embodiments, $R^{c1}$ is propylene. In some embodiments, $R^{c2}$ is aryl. In some embodiments, $R^{c2}$ is phenyl. In some embodiments, $R^d$ is hydrogen. In some embodiments, $R^d$ is not hydrogen. In some embodiments, $R^d$ is alkyl. In some embodiments, $R^d$ is methyl, ethyl, propyl, or butyl. In some embodiments, $R^d$ is methyl. In some embodiments, both $R^b$ and $R^d$ are not hydrogen. In some embodiments, both $R^b$ and $R^d$ are alkyl. In some embodiments, both $R^b$ and $R^d$ are methyl. In some embodiments, $R^b$ is hydrogen and $R^d$ is alkyl. In some embodiments, $R^b$ is hydrogen and $R^d$ is methyl. In some embodiments, $R^b$ is alkyl and $R^d$ is hydrogen. In some embodiments, $R^b$ is methyl and $R^d$ is hydrogen. In some embodiments, X is hydrogen. In some embodiments, m is 1. In some embodiments, n is 2.

In some embodiments, $Q^1$ is a bond; RING is a substituted heteroaryl group; $Q^2$ is alkylene; $Q^3$ is aryl or heteroaryl; $Q^4$ is hydrogen, hydroxyl, methyl, ethyl, phenyl, or para-toluyl; $R^a$ is an acyl group or an alkoxycarbonyl group; $R^b$ is alkyl or hydrogen; $R^{c1}$ is alkylene; $R^{c2}$ is aryl or heteroaryl; $R^d$ is alkyl or hydrogen; X is hydrogen; m is 1; and n is 2, wherein at least one of $R^b$ and $R^d$ is alkyl.

In some embodiments, $Q^1$ is a bond; RING is a substituted heteroaryl group; $Q^2$ is alkylene; $Q^3$ is aryl; $Q^4$ is hydrogen, hydroxyl, methyl, ethyl, phenyl, or para-toluyl; $R^a$ is an alkoxycarbonyl group; $R^b$ is alkyl or hydrogen; $R^{c1}$ is alkylene; $R^{c2}$ is aryl or heteroaryl; $R^d$ is alkyl or hydrogen; X is hydrogen; m is 1; and n is 2, wherein at least one of $R^b$ and $R^d$ is alkyl.

In some embodiments, $Q^1$ is a bond; RING is a substituted heteroaryl group; $Q^2$ is methylene; $Q^3$ is aryl; $Q^4$ is hydrogen, hydroxyl, methyl, ethyl, phenyl, or para-toluyl; $R^a$ is an alkoxycarbonyl group; $R^b$ is alkyl or hydrogen; $R^{c1}$ is methylene; $R^{c2}$ is aryl; $R^d$ is alkyl or hydrogen; X is hydrogen; m is 1; and n is 2, wherein at least one of $R^b$ and $R^d$ is alkyl.

In some embodiments, $Q^1$ is a bond; RING is a 2-substituted-thiazol-4-yl group or a 4-substituted-thiazol-2-yl group; $Q^2$ is methylene; $Q^3$ is 4-substituted phenyl; $Q^4$ is hydrogen, hydroxyl, methyl, ethyl, phenyl, or para-toluyl; $R^a$ is an alkoxycarbonyl group; $R^b$ is alkyl or hydrogen; $R^{c1}$ is methylene; $R^{c2}$ is phenyl; $R^d$ is alkyl or hydrogen; X is hydrogen; m is 1; and n is 2, wherein at least one of $R^b$ and $R^d$ is alkyl.

In some embodiments, $Q^1$ is a bond; RING is a 2-(thiophenyl)-thiazol-4-yl group or a 4-(thiophenyl)-thiazol-2-yl group; $Q^2$ is methylene; $Q^3$ is 4-substituted phenyl; $Q^4$ is hydrogen, hydroxyl, methyl, ethyl, phenyl, or para-toluyl; $R^a$ is an alkoxycarbonyl group; $R^b$ is alkyl or hydrogen; $R^{c1}$ is methylene; $R^{c2}$ is phenyl; $R^d$ is alkyl or hydrogen; X is hydrogen; m is 1; and n is 2, wherein at least one of $R^b$ and $R^d$ is alkyl.

In some embodiments, $Q^1$ is a bond; RING is a 2-(thiophenyl)-thiazol-4-yl group or a 4-(thiophenyl)-thiazol-2-yl group; $Q^2$ is methylene; $Q^3$ is 4-substituted phenyl; $Q^4$ is hydrogen, hydroxyl, methyl, ethyl, phenyl, or para-toluyl; $R^a$ is a methoxycarbonyl group; $R^b$ is alkyl or hydrogen; $R^{c1}$ is methylene; $R^{c2}$ is phenyl; $R^d$ is alkyl or hydrogen; X is hydrogen; m is 1; and n is 2, wherein at least one of $R^b$ and $R^d$ is alkyl.

In some embodiments, $Q^1$ is a bond; RING is a 2-(thiophen-2-yl)-thiazol-4-yl group or a 4-(thiophen-2-yl)-thiazol-2-yl group; $Q^2$ is methylene; $Q^3$ is 4-substituted phenyl; $Q^4$ is hydroxyl; $R^a$ is a methoxycarbonyl group; $R^b$ is methyl or hydrogen; $R^{c1}$ is methylene; $R^{c2}$ is phenyl; $R^d$ is methyl or hydrogen; X is hydrogen; m is 1; and n is 2, wherein at least one of $R^b$ and $R^d$ is methyl.

In some embodiments, $Q^1$ is a bond; RING is a 2-(thiophen-2-yl)-thiazol-4-yl group or a 4-(thiophen-2-yl)-thiazol-2-yl group; $Q^2$ is methylene; $Q^3$ is 4-substituted phenyl; $Q^4$ is hydroxyl; $R^a$ is a methoxycarbonyl group; $R^b$ is methyl; $R^{c1}$ is methylene; $R^{c2}$ is phenyl; $R^d$ is methyl; X is hydrogen; m is 1; and n is 2.

In some embodiments, $Q^1$ is a bond; RING is a 2-(thiophen-2-yl)-thiazol-4-yl group or a 4-(thiophen-2-yl)-thiazol-2-yl group; $Q^2$ is methylene; $Q^3$ is 4-substituted phenyl; $Q^4$ is hydroxyl; $R^a$ is a methoxycarbonyl group; $R^b$ is hydrogen; $R^{c1}$ is methylene; $R^{c2}$ is phenyl; $R^d$ is methyl; X is hydrogen; m is 1; and n is 2.

In some embodiments, $Q^1$ is a bond; RING is a 2-(thiophen-2-yl)-thiazol-4-yl group or a 4-(thiophen-2-yl)-thiazol-2-yl group; $Q^2$ is methylene; $Q^3$ is 4-substituted phenyl; $Q^4$ is hydroxyl; $R^a$ is a methoxycarbonyl group; $R^b$ is methyl; $R^{c1}$ is methylene; $R^{c2}$ is phenyl; $R^d$ is hydrogen; X is hydrogen; m is 1; and n is 2.

In some embodiments, a compound of the disclosure is a compound of the formula:

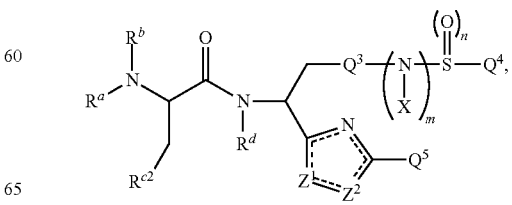

or a pharmaceutically-acceptable salt or zwitterion thereof, wherein: $Q^3$ is cycloalkyl, heterocycloalkyl, aryl, or heteroaryl, any of which is unsubstituted or substituted; $Q^4$ is hydrogen, hydroxyl, methyl, ethyl, phenyl, or para-toluyl; $Q^5$ is cycloalkyl, heterocycloalkyl, aryl, heteroaryl, alkyl, or any of which is unsubstituted or substituted, or hydrogen; $R^a$ is hydrogen, an acyl group, an alkoxycarbonyl group, an amide group, or an amidine group; $R^b$ is alkyl, alkenyl, alkynyl, cycloalkyl, or cycloalkenyl, any of which is unsubstituted or substituted, or hydrogen; $R^{c2}$ is alkyl, alkenyl, alkynyl, cycloalkyl, cycloalkenyl, heterocycloalkyl, aryl, or heteroaryl, any of which is unsubstituted or substituted, or hydrogen; $R^d$ is alkyl, alkenyl, alkynyl, cycloalkyl, or cycloalkenyl, any of which is unsubstituted or substituted, or hydrogen; X is methyl or hydrogen; m is 0 or 1; n is 0, 1, or 2; $Z^1$ is S or CH; $Z^2$ is S or CH; and each ==== is chosen to provide a six-electron system, wherein one of $Z^1$ and $Z^2$ is S, and wherein at least one of $R^b$ and $R^d$ is not hydrogen.

In some embodiments, $Q^3$ is aryl. In some embodiments, $Q^3$ is phenyl. In some embodiments, $Q^3$ is substituted phenyl. In some embodiments, $Q^3$ is 2-substituted-phenyl. In some embodiments, $Q^3$ is 3-substituted-phenyl. In some embodiments, $Q^3$ is 4-substituted-phenyl. In some embodiments, $Q^4$ is hydrogen, hydroxyl, methyl, ethyl, phenyl, or para-toluyl. In some embodiments, $Q^4$ is hydroxyl. In some embodiments, $Q^5$ is cycloalkyl, heterocycloalkyl, aryl, heteroaryl, or alkyl, any of which is unsubstituted or substituted, or hydrogen. In some embodiments, $Q^5$ is aryl. In some embodiments, $Q^5$ is phenyl that is unsubstituted or unsubstituted. In some embodiments, $Q^5$ is heteroaryl. In some embodiments, $Q^5$ is heteroaryl that is unsubstituted or substituted. In some embodiments, $Q^5$ is alkyl. In some embodiments, $Q^5$ is methyl, ethyl, propyl, butyl, isopropyl, isobutyl, or tert-butyl, any of which is unsubstituted or substituted. In some embodiments, $Q^5$ is aryl. In some embodiments, $Q^5$ is phenyl. In some embodiments, $Q^5$ is a thiophenyl group. In some embodiments, $Q^5$ is a thiophen-2-yl group. In some embodiments, $Q^5$ is a thiophen-3-yl group. In some embodiments, $Q^5$ is hydrogen. In some embodiments, $R^a$ is hydrogen. In some embodiments, $R^a$ is an acyl group. In some embodiments, $R^a$ is acetyl, propionyl, or butyryl. In some embodiments, $R^a$ is an alkoxycarbonyl group. In some embodiments, $R^a$ is a methoxycarbonyl group. In some embodiments, $R^a$ is an ethoxycarbonyl group. In some embodiments, $R^a$ is a propyloxycarbonyl group. In some embodiments, $R^a$ is a butyloxycarbonyl group. In some embodiments, $R^a$ is an isopropyloxycarbonyl group. In some embodiments, $R^a$ is a tert-butyloxycarbonyl group. In some embodiments, $R^b$ is hydrogen. In some embodiments, $R^b$ is not hydrogen. In some embodiments, $R^b$ is alkyl. In some embodiments, $R^b$ is methyl, ethyl, propyl, or butyl. In some embodiments, $R^b$ is methyl. In some embodiments, $R^{c2}$ is aryl. In some embodiments, $R^{c2}$ is phenyl. In some embodiments, $R^d$ is hydrogen. In some embodiments, $R^d$ is not hydrogen. In some embodiments, $R^d$ is alkyl. In some embodiments, $R^d$ is methyl, ethyl, propyl, or butyl. In some embodiments, $R^d$ is methyl. In some embodiments, both $R^b$ and $R^d$ are not hydrogen. In some embodiments, both $R^b$ and $R^d$ are alkyl. In some embodiments, both $R^b$ and $R^d$ are methyl. In some embodiments, $R^b$ is hydrogen and $R^d$ is alkyl. In some embodiments, $R^b$ is hydrogen and $R^d$ is methyl. In some embodiments, $R^b$ is alkyl and $R^d$ is hydrogen. In some embodiments, $Z^1$ is S and $R^d$ is hydrogen. In some embodiments, $Z^2$ is S and $Z^1$ and CH. In some embodiments, $Z^2$ is S and $Z^1$ and CH. In some embodiments, X is hydrogen. In some embodiments, m is 1. In some embodiments, n is 2.

In some embodiments, $Q^3$ is aryl or heteroaryl; $Q^4$ is hydrogen, hydroxyl, methyl, ethyl, phenyl, or para-toluyl; $Q^5$ is aryl, heteroaryl, alkyl, or cycloalkyl; $R^a$ is an acyl group or an alkoxycarbonyl group; $R^b$ is alkyl or hydrogen; $R^{c2}$ is aryl or heteroaryl; $R^d$ is alkyl or hydrogen; X is hydrogen; m is 1; and n is 2, wherein at least one of $R^b$ and $R^d$ is alkyl. In some embodiments, $Z^2$ is S and $Z^1$ and CH.

In some embodiments, $Q^3$ is aryl; $Q^4$ is hydrogen, hydroxyl, methyl, ethyl, phenyl, or para-toluyl; $Q^5$ is heteroaryl; $R^a$ is an alkoxycarbonyl group; $R^b$ is alkyl or hydrogen; $R^{c2}$ is aryl or heteroaryl; $R^d$ is alkyl or hydrogen; X is hydrogen; m is 1; and n is 2, wherein at least one of $R^b$ and $R^d$ is alkyl. In some embodiments, $Z^2$ is S and $Z^1$ and CH.

In some embodiments, $Q^3$ is aryl; $Q^4$ is hydrogen, hydroxyl, methyl, ethyl, phenyl, or para-toluyl; $Q^5$ is heteroaryl; $R^a$ is an alkoxycarbonyl group; $R^b$ is alkyl or hydrogen; $R^{c2}$ is aryl; $R^d$ is alkyl or hydrogen; X is hydrogen; m is 1; and n is 2, wherein at least one of $R^b$ and $R^d$ is alkyl. In some embodiments, $Z^2$ is S and $Z^1$ and CH.

In some embodiments, $Q^3$ is 4-substituted phenyl; $Q^4$ is hydrogen, hydroxyl, methyl, ethyl, phenyl, or para-toluyl; $Q^5$ is heteroaryl; $R^a$ is an alkoxycarbonyl group; $R^b$ is alkyl or hydrogen; $R^{c2}$ is phenyl; $R^d$ is alkyl or hydrogen; X is hydrogen; m is 1; and n is 2, wherein at least one of $R^b$ and $R^d$ is alkyl. In some embodiments, $Z^2$ is S and $Z^1$ and CH.

In some embodiments, $Q^3$ is 4-substituted phenyl; $Q^4$ is hydrogen, hydroxyl, methyl, ethyl, phenyl, or para-toluyl; $Q^5$ is a thiophenyl group; $R^a$ is an alkoxycarbonyl group; $R^b$ is alkyl or hydrogen; $R^{c2}$ is phenyl; $R^d$ is alkyl or hydrogen; X is hydrogen; m is 1; and n is 2, wherein at least one of $R^b$ and $R^d$ is alkyl. In some embodiments, $Z^2$ is S and $Z^1$ and CH.

In some embodiments, $Q^3$ is 4-substituted phenyl; $Q^4$ is hydrogen, hydroxyl, methyl, ethyl, phenyl, or para-toluyl; $Q^5$ is a thiophen-2-yl group; $R^a$ is an alkoxycarbonyl group; $R^b$ is alkyl or hydrogen; $R^{c2}$ is phenyl; $R^d$ is alkyl or hydrogen; X is hydrogen; m is 1; and n is 2, wherein at least one of $R^b$ and $R^d$ is alkyl. In some embodiments, $Z^2$ is S and $Z^1$ and CH.

In some embodiments, $Q^3$ is 4-substituted phenyl; $Q^4$ is hydrogen, hydroxyl, methyl, ethyl, phenyl, or para-toluyl; $Q^5$ is a thiophen-2-yl group; $R^a$ is a methoxycarbonyl group; $R^b$ is alkyl or hydrogen; $R^{c2}$ is phenyl; $R^d$ is alkyl or hydrogen; X is hydrogen; m is 1; and n is 2, wherein at least one of $R^b$ and $R^d$ is alkyl. In some embodiments, $Z^2$ is S and $Z^1$ and CH.

In some embodiments, $Q^3$ is 4-substituted phenyl; $Q^4$ is hydroxyl; $Q^5$ is a thiophen-2-yl group; $R^a$ is a methoxycarbonyl group; $R^b$ is methyl or hydrogen; $R^{c2}$ is phenyl; $R^d$ is methyl or hydrogen; X is hydrogen; m is 1; and n is 2, wherein at least one of $R^b$ and $R^d$ is methyl. In some embodiments, $Z^2$ is S and $Z^1$ and CH.

In some embodiments, $Q^3$ is 4-substituted phenyl; $Q^4$ is hydroxyl; $Q^5$ is a thiophen-2-yl group; $R^a$ is a methoxycarbonyl group; $R^b$ is methyl; $R^{c2}$ is phenyl; $R^d$ is methyl; X is hydrogen; m is 1; and n is 2. In some embodiments, $Z^2$ is S and $Z^1$ and CH.

In some embodiments, $Q^3$ is 4-substituted phenyl; $Q^4$ is hydroxyl; $Q^5$ is a thiophen-2-yl group; $R^a$ is a methoxycarbonyl group; $R^b$ is hydrogen; $R^{c2}$ is phenyl; $R^d$ is methyl; X is hydrogen; m is 1; and n is 2. In some embodiments, $Z^2$ is S and $Z^1$ and CH.

In some embodiments, $Q^3$ is 4-substituted phenyl; $Q^4$ is hydroxyl; $Q^5$ is a thiophen-2-yl group; $R^a$ is a methoxycarbonyl group; $R^b$ is methyl; $R^{c2}$ is phenyl; $R^d$ is hydrogen; X is hydrogen; m is 1; and n is 2. In some embodiments, $Z^2$ is S and $Z^1$ and CH.

In some embodiments, a compound of the disclosure is a compound of the formula:

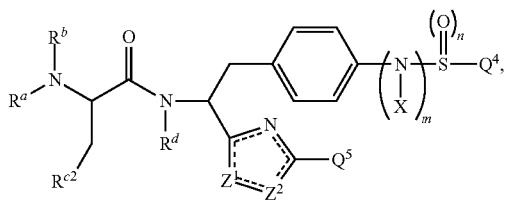

or a pharmaceutically-acceptable salt or zwitterion thereof, wherein: Q is hydrogen, hydroxyl, methyl, ethyl, phenyl, or para-toluyl; $Q^5$ is heterocycloalkyl, aryl, heteroaryl, alkyl, or cycloalkyl, any of which is unsubstituted or substituted, or hydrogen; $R^a$ is hydrogen, an acyl group, an alkoxycarbonyl group, an amide group, or an amidine group; $R^b$ is alkyl, alkenyl, alkynyl, cycloalkyl, or cycloalkenyl, any of which is unsubstituted or substituted, or hydrogen; $R^{c2}$ is alkyl, alkenyl, alkynyl, cycloalkyl, cycloalkenyl, heterocycloalkyl, aryl, or heteroaryl, any of which is unsubstituted or substituted, or hydrogen; $R^d$ is alkyl, alkenyl, alkynyl, cycloalkyl, or cycloalkenyl, any of which is unsubstituted or substituted, or hydrogen; X is methyl or hydrogen; m is 0 or 1; n is 0, 1, or 2; $Z^1$ is S or CH; $Z^2$ is S or CH; and each ===== is chosen to provide a ===== six-electron system, wherein one of $Z^1$ and $Z^2$ is S, and wherein at least one of $R^b$ and $R^d$ is not hydrogen.

In some embodiments, $Q^4$ is hydrogen, hydroxyl, methyl, ethyl, phenyl, or para-toluyl. In some embodiments, $Q^4$ is hydroxyl. In some embodiments, $Q^5$ is heterocycloalkyl, aryl, heteroaryl, alkyl, or cycloalkyl, any of which is unsubstituted or substituted, or hydrogen. In some embodiments, $Q^5$ is aryl. In some embodiments, $Q^5$ is phenyl that is unsubstituted or unsubstituted. In some embodiments, $Q^5$ is heteroaryl. In some embodiments, $Q^5$ is heteroaryl that is unsubstituted or substituted. In some embodiments, $Q^5$ is alkyl. In some embodiments, $Q^5$ is methyl, ethyl, propyl, butyl, isopropyl, isobutyl, or tert-butyl, any of which is unsubstituted or substituted. In some embodiments, $Q^5$ is phenyl. In some embodiments, $Q^5$ is a thiophenyl group. In some embodiments, $Q^5$ is a thiophen-2-yl group. In some embodiments, $Q^5$ is a thiophen-3-yl group. In some embodiments, $Q^5$ is hydrogen. In some embodiments, $R^a$ is hydrogen. In some embodiments, $R^a$ is an acyl group. In some embodiments, $R^a$ is acetyl, propionyl, or butyryl. In some embodiments, $R^a$ is an alkoxycarbonyl group. In some embodiments, $R^a$ is a methoxycarbonyl group. In some embodiments, $R^a$ is an ethoxycarbonyl group. In some embodiments, $R^a$ is a propyloxycarbonyl group. In some embodiments, $R^a$ is a butyloxycarbonyl group. In some embodiments, $R^a$ is an isopropyloxycarbonyl group. In some embodiments, $R^a$ is a tert-butyloxycarbonyl group. In some embodiments, $R^b$ is hydrogen. In some embodiments, $R^b$ is not hydrogen. In some embodiments, $R^b$ is alkyl. In some embodiments, $R^b$ is methyl, ethyl, propyl, or butyl. In some embodiments, $R^b$ is methyl. In some embodiments, $R^{c2}$ is aryl. In some embodiments, $R^{c2}$ is phenyl. In some embodiments, $R^d$ is hydrogen. In some embodiments, $R^d$ is not hydrogen. In some embodiments, $R^d$ is alkyl. In some embodiments, $R^d$ is methyl, ethyl, propyl, or butyl. In some embodiments, $R^d$ is methyl. In some embodiments, both $R^b$ and $R^d$ are not hydrogen. In some embodiments, both $R^b$ and $R^d$ are alkyl. In some embodiments, both $R^b$ and $R^d$ are methyl. In some embodiments, $R^b$ is hydrogen and $R^d$ is alkyl. In some embodiments, $R^b$ is hydrogen and $R^d$ is methyl. In some embodiments, $R^b$ is alkyl and $R^d$ is hydrogen. In some embodiments, $R^b$ is methyl and $R^d$ is hydrogen. In some embodiments, $Z^1$ is S and $Z^2$ is CH. In some embodiments, $Z^2$ is S and $Z^1$ is CH. In some embodiments, X is hydrogen. In some embodiments, m is 1. In some embodiments, n is 2.

In some embodiments, $Q^4$ is hydrogen, hydroxyl, methyl, ethyl, phenyl, or para-toluyl; $Q^5$ is aryl, heteroaryl, alkyl, or cycloalkyl; $R^a$ is an acyl group or an alkoxycarbonyl group; $R^b$ is alkyl or hydrogen; $R^{c2}$ is aryl or heteroaryl; $R^d$ is alkyl or hydrogen; X is hydrogen; m is 1; and n is 2, wherein at least one of $R^b$ and $R^d$ is alkyl. In some embodiments, $Z^2$ is S and $Z^1$ and CH.

In some embodiments, $Q^4$ is hydrogen, hydroxyl, methyl, ethyl, phenyl, or para-toluyl; $Q^5$ is heteroaryl; $R^a$ is an alkoxycarbonyl group; $R^b$ is alkyl or hydrogen; $R^{c2}$ is aryl or heteroaryl; $R^d$ is alkyl or hydrogen; X is hydrogen; m is 1; and n is 2, wherein at least one of $R^b$ and $R^d$ is alkyl. In some embodiments, $Z^2$ is S and $Z^1$ is CH.

In some embodiments, $Q^4$ is hydrogen, hydroxyl, methyl, ethyl, phenyl, or para-toluyl; $Q^5$ is heteroaryl; $R^a$ is an alkoxycarbonyl group; $R^b$ is alkyl or hydrogen; $R^{c2}$ is aryl; $R^d$ is alkyl or hydrogen; X is hydrogen; m is 1; and n is 2, wherein at least one of $R^b$ and $R^d$ is alkyl. In some embodiments, $Z^2$ is S and $Z^1$ is CH.

In some embodiments, $Q^4$ is hydrogen, hydroxyl, methyl, ethyl, phenyl, or para-toluyl; $Q^5$ is heteroaryl; $R^a$ is an alkoxycarbonyl group; $R^b$ is alkyl or hydrogen; $R^{c2}$ is phenyl; $R^d$ is alkyl or hydrogen; X is hydrogen; m is 1; and n is 2, wherein at least one of $R^b$ and $R^d$ is alkyl. In some embodiments, $Z^2$ is S and $Z^1$ is CH.

In some embodiments, $Q^4$ is hydrogen, hydroxyl, methyl, ethyl, phenyl, or para-toluyl; $Q^5$ is a thiophenyl group; $R^a$ is an alkoxycarbonyl group; $R^b$ is alkyl or hydrogen; $R^{c2}$ is phenyl; $R^d$ is alkyl or hydrogen; X is hydrogen; m is 1; and n is 2, wherein at least one of $R^b$ and $R^d$ is alkyl. In some embodiments, $Z^2$ is S and $Z^1$ is CH.

In some embodiments, $Q^4$ is hydrogen, hydroxyl, methyl, ethyl, phenyl, or para-toluyl; $Q^5$ is a thiophen-2-yl group; $R^a$ is an alkoxycarbonyl group; $R^b$ is alkyl or hydrogen; $R^{c2}$ is phenyl; $R^d$ is alkyl or hydrogen; X is hydrogen; m is 1; and n is 2, wherein at least one of $R^b$ and $R^d$ is alkyl. In some embodiments, $Z^2$ is S and $Z^1$ is CH.

In some embodiments, $Q^4$ is hydrogen, hydroxyl, methyl, ethyl, phenyl, or para-toluyl; $Q^5$ is a thiophen-2-yl group; $R^a$ is a methoxycarbonyl group; $R^b$ is alkyl or hydrogen; $R^{c2}$ is phenyl; $R^d$ is alkyl or hydrogen; X is hydrogen; m is 1; and n is 2, wherein at least one of $R^b$ and $R^d$ is alkyl. In some embodiments, $Z^2$ is S and $Z^1$ is CH.

In some embodiments, $Q^4$ is hydroxyl; $Q^5$ is a thiophen-2-yl group; $R^a$ is a methoxycarbonyl group; $R^b$ is methyl or hydrogen; $R^{c2}$ is phenyl; $R^d$ is methyl or hydrogen; X is hydrogen; m is 1; and n is 2, wherein at least one of $R^b$ and $R^d$ is methyl. In some embodiments, $Z^2$ is S and $Z^1$ is CH.

In some embodiments, $Q^4$ is hydroxyl; $Q^5$ is a thiophen-2-yl group; $R^a$ is a methoxycarbonyl group; $R^b$ is methyl; $R^{c2}$ is phenyl; $R^d$ is methyl; X is hydrogen; m is 1; and n is 2. In some embodiments, $Z^2$ is S and $Z^1$ is CH.

In some embodiments, $Q^4$ is hydroxyl; $Q^5$ is a thiophen-2-yl group; $R^a$ is a methoxycarbonyl group; $R^b$ is hydrogen; $R^{c2}$ is phenyl; $R^d$ is methyl; X is hydrogen; m is 1; and n is 2. In some embodiments, $Z^2$ is S and $Z^1$ is CH.

In some embodiments, $Q^4$ is hydroxyl; $Q^5$ is a thiophen-2-yl group; $R^a$ is a methoxycarbonyl group; $R^b$ is methyl; $R^{c2}$ is phenyl; $R^d$ is hydrogen; X is hydrogen; m is 1; and n is 2. In some embodiments, $Z^2$ is S and $Z^1$ is CH.

In some embodiments, a compound of the disclosure is a compound of the formula:

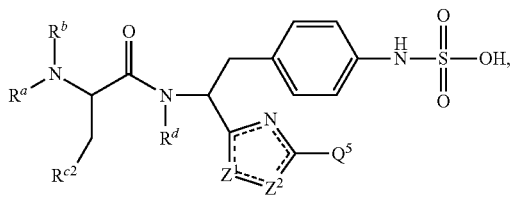

or a pharmaceutically-acceptable salt or zwitterion thereof, wherein:

$Q^5$ is heterocycloalkyl, aryl, heteroaryl, alkyl, or cycloalkyl, any of which is unsubstituted or substituted, or hydrogen;

$R^a$ is hydrogen, an acyl group, an alkoxycarbonyl group, an amidine group, or an amide group;

$R^b$ is alkyl, alkenyl, alkynyl, cycloalkyl, or cycloalkenyl, any of which is unsubstituted or substituted, or hydrogen;

$R^{c2}$ is alkyl, alkenyl, alkynyl, cycloalkyl, cycloalkenyl, heterocycloalkyl, aryl, or heteroaryl, any of which is unsubstituted or substituted, or hydrogen;

$R^d$ is alkyl, alkenyl, alkynyl, cycloalkyl, or cycloalkenyl, any of which is unsubstituted or substituted, or hydrogen;

$Z^1$ is S or CH;

$Z^2$ is S or CH; and each ====== is chosen to provide a six-electron system, wherein one of $Z^1$ and $Z^2$ is S, and wherein at least one of $R^b$ and $R^d$ is not hydrogen.

In some embodiments, $Q^5$ is cycloalkyl, heterocycloalkyl, aryl, heteroaryl, or alkyl, any of which is unsubstituted or substituted, or hydrogen. In some embodiments, $Q^5$ is aryl. In some embodiments, $Q^5$ is phenyl that is unsubstituted or unsubstituted. In some embodiments, $Q^5$ is heteroaryl. In some embodiments, $Q^5$ is heteroaryl that is unsubstituted or substituted. In some embodiments, $Q^5$ is alkyl. In some embodiments, $Q^5$ is methyl, ethyl, propyl, butyl, isopropyl, isobutyl, or tert-butyl, any of which is unsubstituted or substituted. In some embodiments, $Q^5$ is aryl. In some embodiments, $Q^5$ is phenyl. In some embodiments, $Q^5$ is a thiophenyl group. In some embodiments, $Q^5$ is a thiophen-2-yl group. In some embodiments, $Q^5$ is a thiophen-3-yl group. In some embodiments, $Q^5$ is hydrogen. In some embodiments, $R^a$ is hydrogen. In some embodiments, $R^a$ is an acyl group. In some embodiments, $R^a$ is acetyl, propionyl, or butyryl. In some embodiments, $R^a$ is an alkoxycarbonyl group. In some embodiments, $R^a$ is a methoxycarbonyl group. In some embodiments, $R^a$ is an ethoxycarbonyl group. In some embodiments, $R^a$ is a propyloxycarbonyl group. In some embodiments, $R^a$ is a butyloxycarbonyl group. In some embodiments, $R^a$ is an isopropyloxycarbonyl group. In some embodiments, $R^a$ is a tert-butyloxycarbonyl group. In some embodiments, $R^b$ is hydrogen. In some embodiments, $R^b$ is not hydrogen. In some embodiments, $R^b$ is alkyl. In some embodiments, $R^b$ is methyl, ethyl, propyl, or butyl. In some embodiments, $R^b$ is methyl. In some embodiments, $R^{c2}$ is aryl. In some embodiments, $R^{c2}$ is phenyl. In some embodiments, $R^d$ is hydrogen. In some embodiments, $R^d$ is not hydrogen. In some embodiments, $R^d$ is alkyl. In some embodiments, $R^d$ is methyl, ethyl, propyl, or butyl. In some embodiments, $R^d$ is methyl. In some embodiments, both $R^b$ and $R^d$ are not hydrogen. In some embodiments, both $R^b$ and $R^d$ are alkyl. In some embodiments, both $R^b$ and $R^d$ are methyl. In some embodiments, $R^b$ is hydrogen and $R^d$ is alkyl. In some embodiments, $R^b$ is hydrogen and $R^d$ is methyl. In some embodiments, $R^b$ is alkyl and $R^d$ is hydrogen. In some embodiments, $R^b$ is methyl and $R^d$ is hydrogen. In some embodiments, $Z^1$ is S and $Z^2$ is CH. In some embodiments, $Z^2$ is S and $Z^1$ and CH.

In some embodiments, $Q^5$ is aryl, heteroaryl, alkyl, or cycloalkyl; $R^a$ is an acyl group or an alkoxycarbonyl group; $R^b$ is alkyl or hydrogen; $R^{c2}$ is aryl or heteroaryl; and $R^d$ is alkyl or hydrogen, wherein at least one of $R^b$ and $R^d$ is alkyl. In some embodiments, $Z^2$ is S and $Z^1$ is CH.

In some embodiments, $Q^5$ is heteroaryl; $R^a$ is an alkoxycarbonyl group; $R^b$ is alkyl or hydrogen; $R^{c2}$ is aryl or heteroaryl; and $R^d$ is alkyl or hydrogen, wherein at least one of $R^b$ and $R^d$ is alkyl. In some embodiments, $Z^2$ is S and $Z^1$ is CH.

In some embodiments, $Q^5$ is heteroaryl; $R^a$ is an alkoxycarbonyl group; $R^b$ is alkyl or hydrogen; $R^{c2}$ is aryl; and $R^d$ is alkyl or hydrogen, wherein at least one of $R^b$ and $R^d$ is alkyl. In some embodiments, $Z^2$ is S and $Z^1$ is CH.

In some embodiments, $Q^5$ is heteroaryl; $R^a$ is an alkoxycarbonyl group; $R^b$ is alkyl or hydrogen; $R^{c2}$ is phenyl; and $R^d$ is alkyl or hydrogen, wherein at least one of $R^b$ and $R^d$ is alkyl. In some embodiments, $Z^2$ is S and $Z^1$ is CH.

In some embodiments, $Q^5$ is a thiophenyl group; $R^a$ is an alkoxycarbonyl group; $R^b$ is alkyl or hydrogen; $R^{c2}$ is phenyl; and $R^d$ is alkyl or hydrogen, wherein at least one of $R^b$ and $R^d$ is alkyl. In some embodiments, $Z^2$ is S and $Z^1$ is CH.

In some embodiments, $Q^5$ is a thiophen-2-yl group; $R^a$ is an alkoxycarbonyl group; $R^b$ is alkyl or hydrogen; $R^{c2}$ is phenyl; and $R^d$ is alkyl or hydrogen, wherein at least one of $R^b$ and $R^d$ is alkyl. In some embodiments, $Z^2$ is S and $Z^1$ is CH.

In some embodiments, $Q^5$ is a thiophen-2-yl group; $R^a$ is a methoxycarbonyl group; $R^b$ is alkyl or hydrogen; $R^{c2}$ is phenyl; and $R^d$ is alkyl or hydrogen, wherein at least one of $R^b$ and $R^d$ is alkyl. In some embodiments, $Z^2$ is S and $Z^1$ is CH.

In some embodiments, $Q^5$ is a thiophen-2-yl group; $R^a$ is a methoxycarbonyl group; $R^b$ is methyl or hydrogen; $R^{c2}$ is phenyl; and $R^d$ is methyl or hydrogen, wherein at least one of $R^b$ and $R^d$ is methyl. In some embodiments, $Z^2$ is S and $Z^1$ is CH.

In some embodiments, $Q^5$ is a thiophen-2-yl group; $R^a$ is a methoxycarbonyl group; $R^b$ is methyl; $R^{c2}$ is phenyl; and $R^d$ is methyl. In some embodiments, $Z^2$ is S and $Z^1$ is CH.

In some embodiments, $Q^5$ is a thiophen-2-yl group; $R^a$ is a methoxycarbonyl group; $R^b$ is hydrogen; $R^{c2}$ is phenyl; and $R^d$ is methyl. In some embodiments, $Z^2$ is S and $Z^1$ is CH.

In some embodiments, $Q^5$ is a thiophen-2-yl group; $R^a$ is a methoxycarbonyl group; $R^b$ is methyl; $R^{c2}$ is phenyl; and $R^d$ is hydrogen. In some embodiments, $Z^2$ is S and $Z^1$ is CH.

In some embodiments, a compound of the disclosure is a compound of the formula:

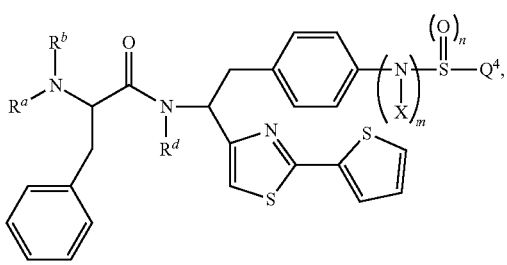

or a pharmaceutically-acceptable salt or zwitterion thereof, wherein: $Q^4$ is hydrogen, hydroxyl, methyl, ethyl, phenyl, or para-toluyl; $R^a$ is hydrogen, an acyl group, an alkoxycarbonyl group, an amide group, or an amidine group; $R^b$ is alkyl, alkenyl, alkynyl, cycloalkyl, or cycloalkenyl, any of which is unsubstituted or substituted, or hydrogen; $R^d$ is alkyl, alkenyl, alkynyl, cycloalkyl, or cycloalkenyl, any of which is unsubstituted or substituted, or hydrogen; X is methyl or hydrogen; m is 0 or 1; and n is 0, 1, or 2, wherein at least one of $R^b$ and $R^d$ is not hydrogen.

In some embodiments, $Q^4$ is hydrogen, hydroxyl, methyl, ethyl, phenyl, or para-toluyl. In some embodiments, $Q^4$ is hydroxyl. In some embodiments, $R^a$ is hydrogen. In some embodiments, $R^a$ is an acyl group. In some embodiments, $R^a$ is acetyl, propionyl, or butyryl. In some embodiments, $R^a$ is an alkoxycarbonyl group. In some embodiments, $R^a$ is a methoxycarbonyl group. In some embodiments, $R^a$ is an ethoxycarbonyl group. In some embodiments, $R^a$ is a propyloxycarbonyl group. In some embodiments, $R^a$ is a butyloxycarbonyl group. In some embodiments, $R^a$ is an isopropyloxycarbonyl group. In some embodiments, $R^a$ is a tert-butyloxycarbonyl group. In some embodiments, $R^b$ is hydrogen. In some embodiments, $R^b$ is not hydrogen. In some embodiments, $R^b$ is alkyl. In some embodiments, $R^b$ is methyl, ethyl, propyl, or butyl. In some embodiments, $R^b$ is methyl. In some embodiments, $R^d$ is hydrogen. In some embodiments, $R^d$ is not hydrogen. In some embodiments, $R^d$ is alkyl. In some embodiments, $R^d$ is methyl, ethyl, propyl, or butyl. In some embodiments, $R^d$ is methyl. In some embodiments, both $R^b$ and $R^d$ are not hydrogen. In some embodiments, both $R^b$ and $R^d$ are alkyl. In some embodiments, both $R^b$ and $R^d$ are methyl. In some embodiments, $R^b$ is hydrogen and $R^d$ is alkyl. In some embodiments, $R^b$ is hydrogen and $R^d$ is methyl. In some embodiments, $R^b$ is alkyl and $R^d$ is hydrogen. In some embodiments, $R^b$ is methyl and $R^d$ is hydrogen. In some embodiments, X is hydrogen. In some embodiments, m is 1. In some embodiments, n is 2.

In some embodiments, $Q^4$ is hydrogen, hydroxyl, methyl, ethyl, phenyl, or para-toluyl; $R^a$ is an acyl group or an alkoxycarbonyl group; $R^b$ is alkyl or hydrogen; $R^d$ is alkyl or hydrogen; X is hydrogen; m is 1; and n is 2, wherein at least one of $R^b$ and $R^d$ is alkyl.

In some embodiments, $Q^4$ is hydrogen, hydroxyl, methyl, ethyl, phenyl, or para-toluyl; $R^a$ is an alkoxycarbonyl group; $R^b$ is alkyl or hydrogen; $R^d$ is alkyl or hydrogen; X is hydrogen; m is 1; and n is 2, wherein at least one of $R^b$ and $R^d$ is alkyl.

In some embodiments, $Q^4$ is hydrogen, hydroxyl, methyl, ethyl, phenyl, or para-toluyl; $R^a$ is a methoxycarbonyl group; $R^b$ is alkyl or hydrogen; $R^d$ is alkyl or hydrogen; X is hydrogen; m is 1; and n is 2, wherein at least one of $R^b$ and $R^d$ is alkyl.

In some embodiments, $Q^4$ is hydroxyl; $R^a$ is a methoxycarbonyl group; $R^b$ is methyl or hydrogen; $R^d$ is methyl or hydrogen; X is hydrogen; m is 1; and n is 2, wherein at least one of $R^b$ and $R^d$ is methyl.

In some embodiments, $Q^4$ is hydroxyl; $R^a$ is a methoxycarbonyl group; $R^b$ is methyl; $R^d$ is methyl; X is hydrogen; m is 1; and n is 2.

In some embodiments, $Q^4$ is hydroxyl; $R^a$ is a methoxycarbonyl group; $R^b$ is hydrogen; $R^d$ is methyl; X is hydrogen; m is 1; and n is 2.

In some embodiments, $Q^4$ is hydroxyl; $R^a$ is a methoxycarbonyl group; $R^b$ is methyl; $R^d$ is hydrogen; X is hydrogen; m is 1; and n is 2.

In some embodiments, a compound of the disclosure is a compound of the formula:

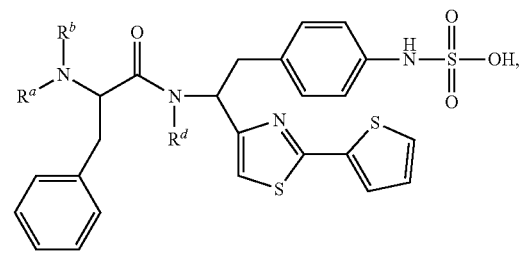

or a pharmaceutically-acceptable salt or zwitterion thereof, wherein: $R^a$ is hydrogen, an acyl group, an alkoxycarbonyl group, an amidine group, or an amide group; $R^b$ is alkyl, alkenyl, alkynyl, cycloalkyl, or cycloalkenyl, any of which is unsubstituted or substituted, or hydrogen; and $R^d$ is alkyl, alkenyl, alkynyl, cycloalkyl, or cycloalkenyl, any of which is unsubstituted or substituted, or hydrogen, wherein at least one of $R^b$ and $R^d$ is not hydrogen.

In some embodiments, $R^a$ is hydrogen. In some embodiments, $R^a$ is an acyl group. In some embodiments, $R^a$ is acetyl, propionyl, or butyryl. In some embodiments, $R^a$ is an alkoxycarbonyl group. In some embodiments, $R^a$ is a methoxycarbonyl group. In some embodiments, $R^a$ is an ethoxycarbonyl group. In some embodiments, $R^a$ is a propyloxycarbonyl group. In some embodiments, $R^a$ is a butyloxycarbonyl group. In some embodiments, $R^a$ is an isopropyloxycarbonyl group. In some embodiments, $R^a$ is a tert-butyloxycarbonyl group. In some embodiments, $R^b$ is hydrogen. In some embodiments, $R^b$ is not hydrogen. In some embodiments, $R^b$ is alkyl. In some embodiments, $R^b$ is methyl, ethyl, propyl, or butyl. In some embodiments, $R^b$ is methyl. In some embodiments, $R^d$ is hydrogen. In some embodiments, $R^d$ is not hydrogen. In some embodiments, $R^d$ is alkyl. In some embodiments, $R^d$ is methyl, ethyl, propyl, or butyl. In some embodiments, $R^d$ is methyl. In some embodiments, both $R^b$ and $R^d$ are not hydrogen. In some embodiments, both $R^b$ and $R^d$ are alkyl. In some embodiments, both $R^b$ and $R^d$ are methyl. In some embodiments, $R^b$ is hydrogen and $R^d$ is alkyl. In some embodiments, $R^b$ is hydrogen and $R^d$ is methyl. In some embodiments, $R^b$ is alkyl and $R^d$ is hydrogen. In some embodiments, $R^b$ is methyl and $R^d$ is hydrogen.

In some embodiments, $R^a$ is an acyl group or an alkoxycarbonyl group; $R^b$ is alkyl or hydrogen; and $R^d$ is alkyl or hydrogen, wherein at least one of $R^b$ and $R^d$ is alkyl.

In some embodiments, $R^a$ is an alkoxycarbonyl group; $R^b$ is alkyl or hydrogen; and $R^d$ is alkyl or hydrogen, wherein at least one of $R^b$ and $R^d$ is alkyl.

In some embodiments, $R^a$ is a methoxycarbonyl group; $R^b$ is alkyl or hydrogen; and $R^d$ is alkyl or hydrogen, wherein at least one of $R^b$ and $R^d$ is alkyl.

In some embodiments, $R^a$ is a methoxycarbonyl group; $R^b$ is methyl or hydrogen; and $R^d$ is methyl or hydrogen, wherein at least one of $R^b$ and $R^d$ is methyl.

In some embodiments, $R^a$ is a methoxycarbonyl group; $R^b$ is methyl; and $R^d$ is methyl.

In some embodiments, $R^a$ is a methoxycarbonyl group; $R^b$ is hydrogen; and $R^d$ is methyl.

In some embodiments, $R^a$ is a methoxycarbonyl group; $R^b$ is methyl; and $R^d$ is hydrogen.

Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, and ester groups.

Non-limiting examples of alkyl and alkylene groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Pharmaceutically-Acceptable Salts.

The present disclosure provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt. In some embodiments, a pharmaceutically-acceptable salt is a lithium salt. In some embodiments, a pharmaceutically-acceptable salt is a sodium salt.

Metal salts can arise from the addition of an inorganic base to a compound of the disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, imidazole, or pyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, a an imidazole salt, or a pyrazine salt.

Acid addition salts can arise from the addition of an acid to a compound of the disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

A compound herein can be a salt of an acidic group, for example:

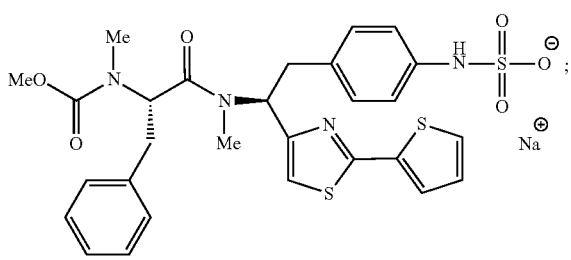

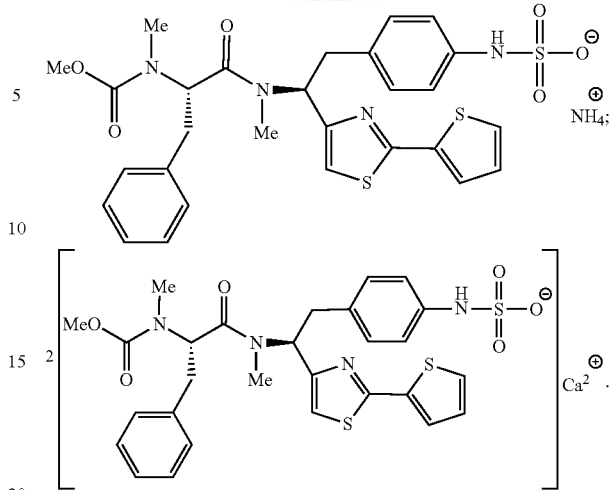

A compound herein can be a salt of a basic group formed from a strong acid, for example:

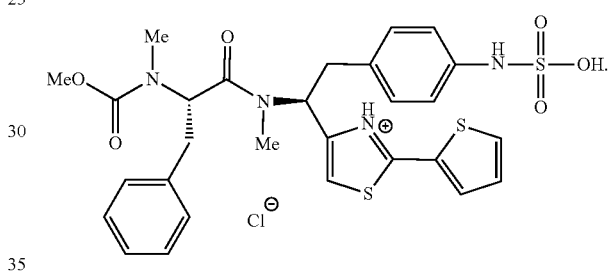

A compound herein can also exist in a zwitterionic form, for example:

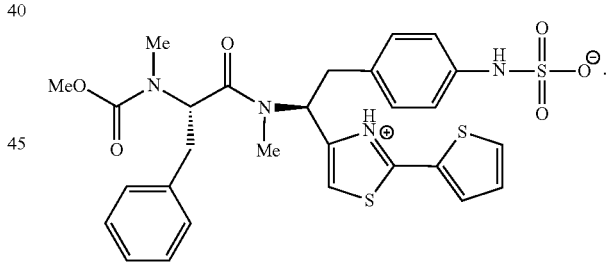

Formulations.

A pharmaceutical composition of the disclosure can provide a therapeutically-effective amount of an inhibitor of HPTPβ. A pharmaceutical composition of the disclosure can provide a therapeutically-effective amount of an activator of Tie-2.

The disclosed formulations can comprise one or more pharmaceutically-acceptable agents, which alone or in combination can solubilize a compound herein or a pharmaceutically-acceptable salt thereof.

In some embodiments, a compound or pharmaceutically-acceptable salt thereof is present in a formulation in an amount of from about 0.1 mg/mL to about 300 mg/mL, from about 0.1 mg/mL to about 1 mg/mL, from about 0.1 mg/mL to about 5 mg/mL, from about 5 mg/mL to about 10 mg/mL, from about 10 mg/mL to about 15 mg/mL, from about 15 mg/mL to about 20 mg/mL, from about 20 mg/mL to about 25 mg/mL, from about 25 mg/mL to about 30 mg/mL, from about 30 mg/mL to about 35 mg/mL, from about 35 mg/mL to about 40 mg/mL, from about 40 mg/mL to about 45 mg/mL, about 45 mg/mL to about 50 mg/mL, from about 50 mg/mL to about 55 mg/mL, from about 55 mg/mL to about 60 mg/mL, from about 60 mg/mL to about 65 mg/mL, from about 65 mg/mL to about 70 mg/mL, from about 70 mg/mL to about 75 mg/mL, about 75 mg/mL to about 80 mg/mL, from about 80 mg/mL to about 85 mg/mL, from about 85 mg/mL to about 90 mg/mL, from about 90 mg/mL to about 95 mg/mL, from about 95 mg/mL to about 100 mg/mL, from about 100 mg/mL to about 110 mg/mL, from about 110 mg/mL to about 120 mg/mL, from about 120 mg/mL to about 130 mg/mL, from about 130 mg/mL to about 140 mg/mL, from about 140 mg/mL to about 150 mg/mL, from about 150 mg/mL to about 160 mg/mL, from about 160 mg/mL to about 170 mg/mL, from about 170 mg/mL to about 180 mg/mL, from about 180 mg/mL to about 190 mg/mL, from about 190 mg/mL to about 200 mg/mL, from about 200 mg/mL to about 220 mg/mL, from about 220 mg/mL to about 240 mg/mL, from about 240 mg/mL to about 260 mg/mL, from about 260 mg/mL to about 280 mg/mL, or from about 280 mg/mL to about 300 mg/mL.

In some embodiments, a compound or pharmaceutically-acceptable salt thereof is present in a formulation in an amount of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

A formulation that is disclosed herein can be made more soluble by the addition of an additive or agent, for example, a cyclodextrin moiety. The improvement of solubility of the formulation can increase by about 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

A formulation disclosed herein can be stable for about 1 day, about 2 days, about 3 days, about 4 days, about 5 days, about 6 days, about 7 days, about 8 days, about 9 days, about 10 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C.

Alcohols.

A non-limiting example of a solubilizing agent includes an organic solvent. Non-limiting examples of organic solvents include alcohols, for example, $C_1$-$C_4$ linear alkyl, $C_3$-$C_4$ branched alkyl, ethanol, ethylene glycol, glycerin, 2-hydroxypropanol, propylene glycol, maltitol, sorbitol, xylitol; substituted or unsubstituted aryl, and benzyl alcohol.

Cyclodextrins.

Non-limiting examples of cyclodextrins include β-cyclodextrin, methyl β-cyclodextrin, 2-hydroxypropyl-β-cyclodextrin (HPβCD), sulfobutylether-β-cyclodextrin sodium salt (SBECD), hydroxyethyl-β-cyclodextrin (HE-β-CD), heptakis (2,6-di-O-methyl)-β-cyclodextrin (DMβCD), α-cyclodextrin, γ-cyclodextrin, and 2-hydroxypropyl-γ-cyclodextrin (HPγCD). A cyclodextrin can possess a large cyclic structure with a channel passing through the center of the structure. The interior of the cyclodextrin can be hydrophobic, and interact favorably with hydrophobic molecules. The exterior of the cyclodextrin can be highly hydrophilic owing to the several hydroxyl groups exposed to bulk solvent. Capture of a hydrophobic molecule, such as a compound disclosed herein, in the channel of the cyclodextrin can result in the formation of a complex stabilized by non-covalent hydrophobic interactions. The complex can be soluble in water, and carry the captured hydrophobic molecule into the bulk solvent.

Formulations of the disclosure can comprise randomly methylated β-cyclodextrins (RAMEB or RMCD). The formulations of the disclosure can comprise RAMEB comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 methyl groups.

The disclosed solubilizing systems comprise 2-hydroxypropyl-beta-cyclodextrin (HPβCD). 2-Hydroxypropyl-β-cyclodextrin [CAS No. 128446-35-5] is commercially available as Cavitron™. 2-Hydroxypropyl-β-cyclodextrin, also described known as hydroxypropyl-β-cyclodextrin, 2-hydroxypropyl-beta-cyclodextrin, hydroxypropyl-beta-cyclodextrin or HPβCD, can be represented by either of the following formulae:

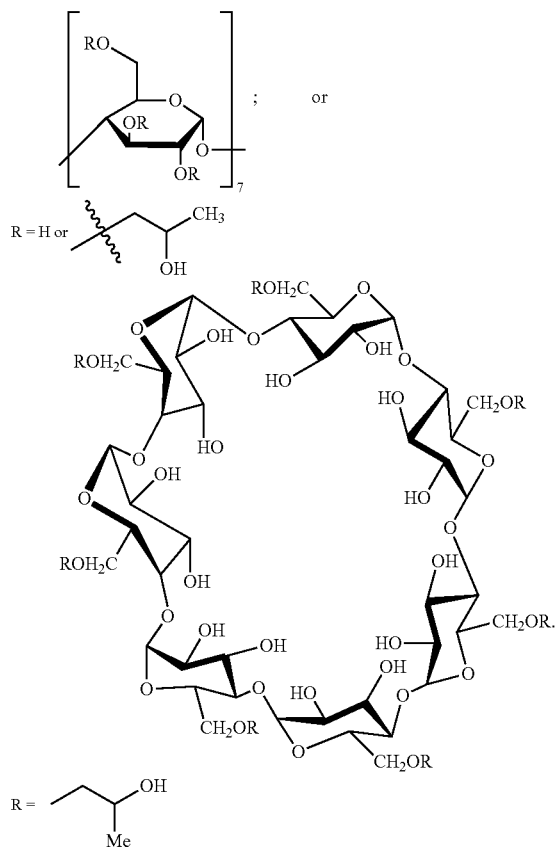

The average molecular weight of Cavitron™, is approximately 1396 Da, wherein the average degree of substitution is from about 0.5 to about 1.3 units of 2-hydroxypropyl per ring glucose unit.

In one embodiment, a formulation disclosed herein can comprise a ratio of about 20 parts of a compound herein or a pharmaceutically-acceptable salt thereof to about 1 part solubilizing system (about 20:about 1), to about 1 part of the compound herein or a pharmaceutically-acceptable salt thereof to about 20 parts solubilizing system (about 1:about 20). For example, a formulation containing about 100 mg of a compound herein or a pharmaceutically-acceptable salt thereof can contain from about 5 mg to about 2000 mg of a solubilizing agent, such as a cyclodextrin. In another embodiment, the ratio can be based on number, or moles, or compound compared to number, or moles, of the solubilizing system.

The following are non-limiting examples of ratios of a compound herein and a solubilizing agent, such as a cyclodextrin. The following examples alternatively describe the ratio of a solubilizing agent, such as a cyclodextrin, and a compound herein. The ratio can be: about 20:about 1; about 19.9:about 1; about 19.8:about 1; about 19.7:about 1; about 19.6 about 1; about 19.5:about 1; about 19.4:about 1; about 19.3:about 1; about 19.2:about 1; about 19.1:about 1; about 19:about 1; about 18.9:about 1; about 18.8:about 1; about 18.7 about 1; about 18.6:about 1; about 18.5:about 1; about 18.4:about 1; about 18.3:about 1; about 18.2:about 1; about 18.1:about 1; about 18:about 1; about 17.9:about 1; about 17.8 about 1; about 17.7:about 1; about 17.6:about 1; about 17.5:about 1; about 17.4:about 1; about 17.3:about 1; about 17.2:about 1; about 17.1:about 1; about 17:about 1; about 16.9 about 1; about 16.8:about 1; about 16.7:about 1; about 16.6:about 1; about 16.5:about 1; about 16.4:about 1; about 16.3:about 1; about 16.2:about 1; about 16.1:about 1; about 16 about 1; about 15.9:about 1; about 15.8:about 1; about 15.7:about 1; about 15.6:about 1; about 15.5:about 1; about 15.4:about 1; about 15.3:about 1; about 15.2:about 1; about 15.1 about 1; about 15:about 1; about 14.9:about 1; about 14.8:about 1; about 14.7:about 1; about 14.6:about 1; about 14.5:about 1; about 14.4:about 1; about 14.3:about 1; about 14.2:about 1; about 14.1:about 1; about 14:about 1; about 13.9:about 1; about 13.8:about 1; about 13.7:about 1; about 13.6:about 1; about 13.5:about 1; about 13.4:about 1; about 13.3:about 1; about 13.2:about 1; about 13.1:about 1; about 13:about 1; about 12.9:about 1; about 12.8 about 1; about 12.7:about 1; about 12.6:about 1; about 12.5:about 1; about 12.4:about 1; about 12.3:about 1; about 12.2:about 1; about 12.1:about 1; about 12:about 1; about 11.9:about 1; about 11.8:about 1; about 11.7:about 1; about 11.6:about 1; about 11.5:about 1; about 11.4:about 1; about 11.3:about 1; about 11.2:about 1; about 11.1:about 1; about 11:about 1; about 10.9:about 1; about 10.8:about 1; about 10.7:about 1:about 10.6:about 1; about 10.5:about 1; about 10.4:about 1; about 10.3:about 1; about 10.2:about 1; about 10.1 about 1; about 10:about 1; about 9.9:about 1; about 9.8:about 1; about 9.7:about 1; about 9.6:about 1; about 9.5:about 1; about 9.4:about 1; about 9.3:about 1; about 9.2:about 1; about 9.1:about 1; about 9:about 1; about 8.9:about 1; about 8.8:about 1; about 8.7:about 1; about 8.6:about 1; about 8.5:about 1; about 8.4:about 1; about 8.3:about 1; about 8.2:about 1; about 8.1:about 1; about 8:about 1; about 7.9:about 1; about 7.8:about 1; about 7.7:about 1; about 7.6:about 1; about 7.5:about 1; about 7.4:about 1; about 7.3:about 1; about 7.2:about 1; about 7.1:about 1; about 7:about 1; about 6.9:about 1; about 6.8:about 1; about 6.7:about 1; about 6.6:about 1; about 6.5:about 1; about 6.4:about 1; about 6.3:about 1; about 6.2:about 1; about 6.1:about 1; about 6:about 1; about 5.9:about 1; about 5.8:about 1; about 5.7 about 1; about 5.6:about 1; about 5.5:about 1; about 5.4:about 1; about 5.3:about 1; about 5.2:about 1; about 5.1:about 1; about 5:about 1; about 4.9:about 1; about 4.8:about 1; about 4.7:about 1; about 4.6:about 1; about 4.5:about 1; about 4.4:about 1; about 4.3:about 1; about 4.2:about 1; about 4.1:about 1; about 4:about 1; about 3.9:about 1; about 3.8:about 1; about 3.7:about 1; about 3.6:about 1; about 3.5:about 1; about 3.4:about 1; about 3.3:about 1; about 3.2:about 1; about 3.1:about 1; about 3:about 1; about 2.9:about 1; about 2.8:about 1; about 2.7:about 1; about 2.6:about 1; about 2.5:about 1; about 2.4:about 1; about 2.3:about 1; about 2.2:about 1; about 2.1:about 1; about 2:about 1; about 1.9:about 1; about 1.8 about 1; about 1.7:about 1; about 1.6:about 1; about 1.5:about 1; about 1.4:about 1; about 1.3:about 1; about 1.2:about 1; about 1.1:about 1; or about 1:about 1.

Polyvinylpyrrolidione.

Another non-limiting example of a solubilizing agent is polyvinylpyrrolidone (PVP), having the formula:

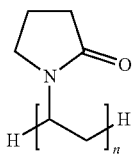

wherein the index n is from about 40 to about 200. PVP's can have an average molecular weight from about 5500 to about 28,000 g/mol. One non-limiting example is PVP-10, having an average molecular weight of approximately 10,000 g/mol.

Polyakyleneoxides and Ethers Thereof.

Another non-limiting example of solubilizing agents includes polyalkyleneoxides, and polymers of alcohols or polyols. Polymers can be mixed, or contain a single monomeric repeat subunit. For example, polyethylene glycols having an average molecular weight of from about 200 to about 20,000, for example, PEG 200, PEG 400, PEG 600, PEG 1000, PEG 1450, PEG 1500, PEG 4000, PEG 4600, and PEG 8000. In a same embodiment, a composition comprises one or more polyethylene glycols chosen from PEG 400, PEG 1000, PEG 1450, PEG 4600 and PEG 8000.

Other polyalkyleneoxides are polypropylene glycols having the formula:

$$HO[CH(CH_3)CH_2O]_xH$$

wherein the index x represents the average number of propyleneoxy units in the polymer. The index x can be represented by a whole number or a fraction. For example, a polypropylene glycol having an average molecular weight of 8,000 g/mole (PPG 8000) can be represented by the formulae:

$$HO[CH(CH_3)CH_2O]_{138}H \text{ or } HO[CH(CH_3)CH_2O]_{137.6}H$$

or the polypropylene glycol can be represented by the common, short hand notation: PPG 8000.

Another example of polypropylene glycols can have an average molecular weight from about 1200 g/mol to about 20,000 g/mol, i.e., a polypropylene glycol having an average molecular weight of about 8,000 g/mol, for example, PPG 8000.

Another solubilizing agent is Polysorbate 80 (Tween™ 80), which is an oleate ester of sorbitol and its anhydrides copolymerized with approximately 20 moles of ethylene oxide for each mole of sorbitol and sorbitol anhydrides. Polysorbate 80 is made up of sorbitan mono-9-octadecenoate poly(oxy-1,2-ethandiyl) derivatives.

Solubilizing agents also include poloxamers having the formula:

$$HO(CH_2CH_2)_{y1}(CH_2CH_2CH_2O)_{y2}(CH_2CH_2O)_{y3}OH$$

which are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol.

Excipients.

A pharmaceutical composition of the disclosure can be a combination of any pharmaceutical compounds described herein with other chemical components, such as carriers, stabilizers, diluents, dispersing agents, suspending agents, thickening agents, or excipients. The pharmaceutical composition facilitates administration of the compound to an organism. Pharmaceutical compositions can be administered in therapeutically-effective amounts as pharmaceutical compositions by various forms and routes including, for example, intravenous, intravitreal, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients. Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically-acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, granulating, dragee-making, levigating, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. The methods and pharmaceutical compositions described herein include the use of crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions, and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the present disclosure include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

The disclosure can be administered as an eye drop. The average volume of each drop administered to a subject can be about 5 µl, about 10 µl, about 15 µl, about 20 µl, about 30

μl, about 40 μl, about 50 μl, about 60 μl, about 70 μl, about 80 μl, about 90 μl, or about 100 μl. The eye drops can contain about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% of a compound of the disclosure. The drops can contain about 1 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 60 mg/ml, about 70 mg/ml, about 80 mg/ml, about 90 mg/ml, about 100 mg/ml, about 120 mg/ml, about 140 mg/ml, about 160 mg/ml, about 180 mg/ml, or about 200 mg/ml of a compound of the disclosure. The individual dose administered to a subject can be about 0.5 μg, about 1 μg, about 2 μg, about 3 μg, about 4 μg, about 5 μg, about 6 μg, about 7 μg, about 8 μg, about 9 μg, about 10 μg, about 20 μg, about 30 μg, about 40 μg, about 50 μg, about 60 μg, about 70 μg, about 80 μg, about 90 μg, about 100 μg, about 150 μg, about 200 μg, about 250 μg, about 300 μg, about 350 μg, about 400 μg, about 450 μg, about 500 μg, about 550 μg, about 600 μg, about 650 μg, about 700 μg, about 750 μg, about 800 μg, about 850 μg, about 900 μg, about 950 μg, about 1 mg, about 1.1 mg, about 1.2 mg, 1.3 mg, about 1.4 mg, about 1.5 mg, about 1.6 mg, about 1.7 mg, about 1.8 mg, about 1.9 mg, or about 2 mg of a compound of the disclosure. In some embodiments, more than one drop can be administered to an eye either at one time or at multiple times throughout the day.

Non-limiting examples of excipients suitable for use in eye drops in the present disclosure include cyclodextrin, α-cyclodextrin, β-cyclodextrin, 2-hydroxypropyl-β-cyclodextrin (HP-3-CD), random methyl-β-cyclodextrin (RM-3-CD), sulfobutyl ether β-cyclodextrin (SBE-β-CD), γ-cyclodextrin, hydroxypropyl-γ-cyclodextrin (HP-γ-CD), hydroxyethyl-β-cyclodextrin (HE-β-CD), heptakis (2,6-di-O-methyl)-β-cyclodextrin (DMβCD), saline, sodium bisulfate, metabisulfite, ascorbic acid, acetylcysteine, benzalkonium chloride, boric acid, hyaluronic acid, hypromellose, propylene glycol, potassium sorbate, sodium chloride, sodium acetate, disodium edetate, sodium dihydrogen phosphate monohydrate, disodium phosphate, sodium hydroxide, hydrochloric acid, glycerol, mannitol, trometamol, tyloxapol, and any combination thereof.

The individual dose administered to a subject can be about 0.5 mg, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, or about 500 mg of a compound of the present disclosure. The individual dose administered to a subject can be from about 0.1 mg to about 25 mg, about 0.1 mg to about 50 mg, about 0.1 mg to about 75 mg, or about 0.1 mg to about 100 mg. The individual dose administered to a subject can be from about 0.5 mg to about 10 mg, about 0.5 mg to about 20 mg, or about 0.5 mg to about 30 mg. In some embodiments, the individual dose administered to a subject can be about 10 mg of a compound of the present disclosure. In some embodiments, the individual dose administered to a subject can be about 15 mg of a compound of the present disclosure. In some embodiments, the individual dose administered to a subject can be about 20 mg of a compound of the present disclosure. In some embodiments, the individual dose administered to a subject can be about 30 mg of a compound of the present disclosure. In some embodiments, the individual dose of a compound of the present disclosure administered to a subject can be about 15 mg twice per day or about 30 mg per day.

Non-limiting examples of pharmaceutically-acceptable excipients suitable for use in the present disclosure include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, anti-microbial agents, plant cellulosic material and spheronization agents, and any combination thereof.

A composition of the present disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

The disclosed compositions can optionally comprise from about 0.001% to about 0.005% weight by volume pharmaceutically-acceptable preservatives. One non-limiting example of a suitable preservative is benzyl alcohol.

In some embodiments, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The disclosed methods include administration of an HPTPβ inhibitor, or a pharmaceutically-acceptable salt thereof, in combination with a pharmaceutically-acceptable carrier. The carrier can be selected to minimize any degradation of the active ingredient and to minimize any adverse side effects in the subject.

The disclosed methods include administration of a Tie-2 activator, or a pharmaceutically-acceptable salt thereof, in combination with a pharmaceutically-acceptable carrier. The carrier can be selected to minimize any degradation of the active ingredient and to minimize any adverse side effects in the subject.

The Tie-2 activator or a pharmaceutically-acceptable salt thereof herein can be conveniently formulated into pharmaceutical compositions composed of one or more pharmaceutically-acceptable carriers. See e.g., *Remington's Pharmaceutical Sciences*, latest edition, by E. W. Martin Mack Pub. Co., Easton, PA, which discloses typical carriers and conventional methods of preparing pharmaceutical compositions that can be used in conjunction with the preparation of formulations of the compound described herein and which is incorporated by reference herein. Such pharmaceuticals can be standard carriers for administration of compositions to humans and non-humans, including solutions such as sterile water, saline, and buffered solutions at physiological pH. Other compositions can be administered according to standard procedures. For example, pharmaceutical compositions can also include one or more additional active ingredients such as antimicrobial agents, anti-inflammatory agents, and anesthetics.

Non-limiting examples of pharmaceutically-acceptable carriers include saline solution, Ringer's solution, and dextrose solution. The pH of the solution can be from about 5 to about 8, and can be from about 7 to about 7.5. Further carriers include sustained release preparations such as semipermeable matrices of solid hydrophobic polymers containing the Tie-2 activator or a pharmaceutically-acceptable salt thereof, where the matrices are in the form of shaped articles, such as films, liposomes, microparticles, and microcapsules.

The disclosed methods relate to administering the Tie-2 activator or a pharmaceutically-acceptable salt thereof as part of a pharmaceutical composition. The disclosed methods relate to administering the HPTPβ inhibitor or a pharmaceutically-acceptable salt thereof as part of a pharmaceutical composition. In various embodiments, compositions of the present disclosure can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In some embodiments, the composition is an in situ gellable aqueous solution.

Pharmaceutical formulations can include additional carriers, as well as thickeners, diluents, buffers, preservatives, and surface active agents in addition to the compounds disclosed herein. Pharmaceutical formulations can also include one or more additional active ingredients such as antimicrobial agents, anti-inflammatory agents, or anesthetics.

An excipient can fill a role as simple and direct as being an inert filler, or an excipient as used herein can be part of a pH stabilizing system or coating to ensure delivery of the ingredients safely to the stomach.

The Tie-2 activator or a pharmaceutically-acceptable salt thereof can also be present in liquids, emulsions, or suspensions for delivery of active therapeutic agents in aerosol form to cavities of the body such as the nose, throat, or bronchial passages. The ratio of Tie-2 activator or a pharmaceutically-acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, for example, in unit dosage form suitable for single administration of a precise dosage. The compositions can contain, as noted above, an effective amount of the Tie-2 activator or a pharmaceutically-acceptable salt thereof in combination with a pharmaceutically-acceptable carrier and, in addition, can include other medicinal agents, pharmaceutical agents, carriers, adjuvants, diluents, etc.

For solid compositions, nontoxic solid carriers include, for example, pharmaceutical grades of mannitol, lactose, starch, magnesium stearate, sodium saccharin, talc, cellulose, glucose, sucrose, and magnesium carbonate. In one embodiment, a composition comprising the Tie-2 activator or a pharmaceutically-acceptable salt thereof in an amount of approximately 4 mg per 0.1 mL liquid is prepared. The liquid phase comprises sterile water and an appropriate amount of a saccharide or polysaccharide.

Pharmaceutical Compositions.

Pharmaceutical compositions containing the compounds described herein can be administered for prophylactic or therapeutic treatments. Compositions can contain any number of active agents. In therapeutic applications, the compositions can be administered to a subject already suffering from a disease or condition, in an amount sufficient to cure or at least partially arrest the symptoms of the disease or condition, or to cure, heal, improve, reduce, lessen, ameliorate, or reduce a likelihood of the disease or condition. Compounds can also be administered to lessen or reduce a likelihood of developing, contracting, or worsening a condition. Amounts effective for this use can vary based on the severity and course of the disease or condition, previous therapy, the subject's health status, weight, response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills or injections. The compounds can be packed together or separately, in a single package or in a plurality of packages. One or all of the therapeutic agents can be given in multiple doses. If not simultaneous, then the timing between the multiple doses can vary.

Compounds and compositions described herein can be packaged as a kit. In some embodiments, the present disclosure provides a kit comprising a compound disclosed herein, or a pharmaceutically-acceptable salt thereof, and written instructions on use of the kit in the treatment of a condition described herein. In some embodiments, the present disclosure provides a kit comprising a compound disclosed herein, or a pharmaceutically-acceptable salt thereof, an antibody, and written instructions on use of the kit in the treatment of a condition described herein.

The compounds described herein can be administered before, during, or after the occurrence of a disease or condition, and the timing of administering the composition containing a compound can vary. For example, the compounds can be used as a prophylactic and can be administered continuously to subjects with a propensity to conditions or diseases to lessen or reduce a likelihood of the occurrence of the disease or condition. The compounds and compositions can be administered to a subject during or as soon as possible after the onset of the symptoms. The administration of the compounds can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for parenteral injection can be presented in unit dosage form, for example, in ampoules, or in multi-dose containers with a preservative.

A Tie-2 activator described herein can be present in a composition in a range of from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg, from about 95 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, or from about 250 mg to about 300 mg.

A Tie-2 activator described herein can be present in a composition in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, or about 300 mg.

Treatment of Subjects with a Tie-2 Activator.

The present disclosure provides methods for treating a subject afflicted with vascular disorders with an activator of Tie-2 or an inhibitor of HPTPβ. The subject can be a human. Treatment can include treating a human in a clinical trial. A treatment can comprise administering to a subject a pharmaceutical composition comprising one or more of the activators of Tie-2 described throughout the disclosure. A treatment can comprise administrating to a subject a therapy that promotes the phosphorylation of a Tie-2 molecule.

The present disclosure provides methods for treating a subject afflicted with vascular disorders with a therapeutically-effective amount of an activator of Tie-2 or an inhibitor of HPTPβ. The subject can be a human. Treatment can include treating a human in a clinical trial. A treatment can comprise administering to a subject a pharmaceutical composition comprising one or more of the activators of Tie-2 described throughout the disclosure. A treatment can comprise administering to a subject a therapy that promotes the phosphorylation of a Tie-2 molecule. A therapeutically-effective amount can be from about 0.1 mg to about 100 mg or from about 0.5 mg to about 30 mg.

Non-limiting examples of possible subjects for administration include the following. Subjects can be humans, non-human primates such as chimpanzees, and other apes and monkey species; farm animals such as cattle, horses, sheep, goats, and swine; domestic animals such as rabbits, dogs, and cats; and laboratory animals including rats, mice, and guinea pigs. A subject can be of any age. Subjects can be, for example, elderly adults, adults, adolescents, pre-adolescents, children, toddlers, and infants.

A subject described herein can express Ang1. A subject described herein can express Ang2. A subject described herein can express both Ang1 and Ang2.

Some conditions can lead to an increase in the levels of Ang-2, altering the ratio of Ang-1/Ang-2 in circulation. In some aspects, a therapy can improve the outcome of a disease state by altering the ratio of Ang-1/Ang-2 in circulation. A therapy can provide an Ang-1/Ang-2 ratio or an Ang-2/Ang-1 ratio of about 1:about 1, about 2:about 1, about 3:about 1, about 4:about 1, about 5:about 1, about 6:about 1, about 7:about 1, about 8:about 1, about 9:about 1, or about 10:about 1.

TABLE 1 provides illustrative compounds of the present disclosure.

TABLE 1

| No. | Compound |
| --- | --- |
| 1 | (structure shown: MeO-carbamate-phenylalanine-amide linked to a benzyl-thiazole-thiophene with a sulfonamide-ONa group) |

TABLE 1-continued

| No. | Compound |
|---|---|
| 2 | sodium (4-{(S)-2-{(S)-2-[(methoxycarbonyl)amino]-3-phenylpropanamido}-2-[2-(thiophen-2-yl)thiazol-4-yl]ethyl}phenyl)sulfamate |
| 3 | sodium (4-{(S)-2-{(S)-2-[(methoxycarbonyl)(methyl)amino]-3-phenylpropanamido}-2-[2-(thiophen-2-yl)thiazol-4-yl]ethyl}phenyl)sulfamate |
| 4 | sodium (4-{(S)-2-{(S)-2-[(methoxycarbonyl)amino]-N-methyl-3-phenylpropanamido}-2-[2-(thiophen-2-yl)thiazol-4-yl]ethyl}phenyl)sulfamate |
| 5 | sodium (4-{(S)-2-{(S)-2-[(methoxycarbonyl)(methyl)amino]-N-methyl-3-phenylpropanamido}-2-[2-(thiophen-2-yl)thiazol-4-yl]ethyl}phenyl)sulfamate |
|  | 4-{(S)-2-[(S)-2-(methoxycarbonylamino)-3-phenylpropanamido]-2-(4-ethylthiazol-2-yl)ethyl}phenylsulfamic acid |

EXAMPLES

Example 1: Preparation of Compound 2 as Shown in Table 1

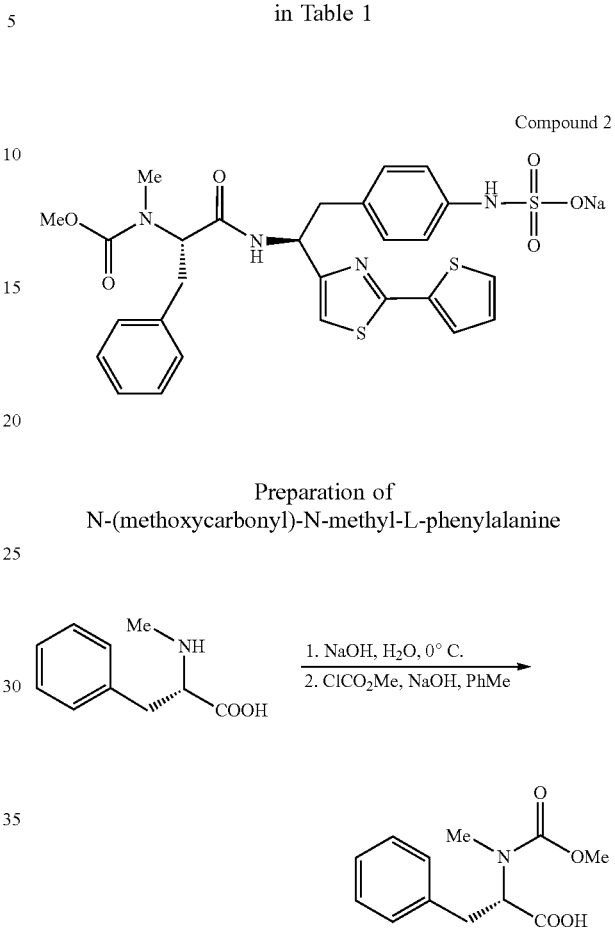

Compound 2

Preparation of N-(methoxycarbonyl)-N-methyl-L-phenylalanine

N-Methyl-L-phenylalanine (23 g, 128.3 mmol, 1 eq.), H$_2$O (115 mL), and an aqueous solution of NaOH (1 mol/L, 140 mL) were added to a 1 L three-necked round-bottomed flask. The resulting solution was cooled to 0° C. A solution of methyl chloroformate (12.06 g, 128.3 mmol, 1 eq.) in toluene (69 mL) and an aqueous solution of NaOH (1 M, 110 mL) were added to the solution dropwise simultaneously via two addition funnels. The pH of the reaction solution was maintained at 8-9 and the reaction temperature was maintained below 10° C. by adjusting the addition rate of both solutions. After complete addition of the chloroformate solution, the reaction mixture was stirred at room temperature for 30 min. The reaction mixture was then washed with methyl tert-butyl ether (50 mL×2). The aqueous layer was acidified to pH 3-4 by a dilute HCl solution (1 M), and extracted with dichloromethane (200 mL×2). The combined dichloromethane phases were dried over anhydrous Na$_2$SO$_4$ (100 g). After filtration and concentration, N-(methoxycarbonyl)-N-methyl-L-phenylalanine was obtained as a clear oil. The oil solidified upon standing at room temperature for 2 days (29 g, 95% yield).

LC-MS: (ES$^+$ m/z) 260 [(M+Na)$^+$]; $^1$H NMR (300 MHz, CDCl$_3$) δ 9.71 (brs, 1H), 7.19-7.34 (m, 5H), 4.82-4.99 (m, 1H), 3.61-3.69 (m, 3H), 3.32-3.43 (m, 1H), 2.99-3.15 (m, 1H), 2.78-2.86 (m, 3H).

Preparation of methyl methyl((S)-1-(((S)-2-(4-nitrophenyl)-1-(2-(thiophen-2-yl)thiazol-4-yl)ethyl)amino)-1-oxo-3-phenylpropan-2-yl)carbamate

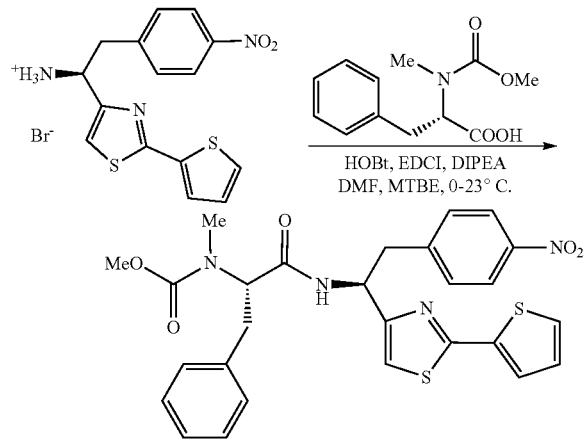

(S)-2-(4-Nitrophenyl)-1-(2-(thiophen-2-yl)thiazol-4-yl)ethan-1-amine hydrobromide (15.66 g, 38 mmol, 1 eq.), hydroxybenzotriazole (HOBt) (8.72 g, 64.6 mmol, 1.7 eq.), 1-ethyl-3-(3-dimethylaminopropyl)carbodiimide (EDCI) (8.74 g, 45.6 mmol, 1.2 eq.), and N,N-diisopropylethylamine (DIPEA) (14.7 g, 114 mmol, 3 eq.) were added to a solution of N-(methoxycarbonyl)-N-methyl-L-phenylalanine (9 g, 38 mmol) in dimethylformamide (DMF) (90 mL) and methyl tert-butyl ether (51 mL). The resulting mixture was stirred at 0° C. for 30 min, and was then allowed to warm to room temperature and stirred overnight. After the completion of the reaction as indicated by thin-layer chromatography (TLC), the reaction mixture was quenched with water (400 mL) and extracted with EtOAc (200 mL×2). The combined organic phase was washed with a diluted aqueous HCl solution (1 M, 200 mL), followed by 5% aqueous NaHCO$_3$ solution (200 mL) and water (200 mL). The organic layer was dried over anhydrous Na$_2$SO$_4$ (100 g), filtered, and concentrated in vacuo to afford crude methyl methyl((S)-1-(((S)-2-(4-nitrophenyl)-1-(2-(thiophen-2-yl)thiazol-4-yl)ethyl)amino)-1-oxo-3-phenylpropan-2-yl)carbamate (20 g, 95% yield).

LC-MS: (ES$^+$ m/z) 551 [(M+H)$^+$]; $^1$H NMR (300 MHz, CDCl$_3$) δ 8.10 (d, J=8.4 Hz, 2H), 7.52 (d, J=3.6 Hz, 1H), 7.44 (d, J=4.8 Hz, 1H), 7.10-7.25 (m, 7H), 6.61-6.68 (m, 2H), 5.38 (m, 1H), 4.75-4.87 (m, 1H), 3.60-3.71 (m, 3H), 3.25-3.36 (m, 3H), 2.90-2.97 (m, 1H), 2.73-2.88 (m, 3H).

Preparation of methyl ((S)-1-(((S)-2-(4-aminophenyl)-1-(2-(thiophen-2-yl)thiazol-4-yl)ethyl)amino)-1-oxo-3-phenylpropan-2-yl)(methyl)carbamate

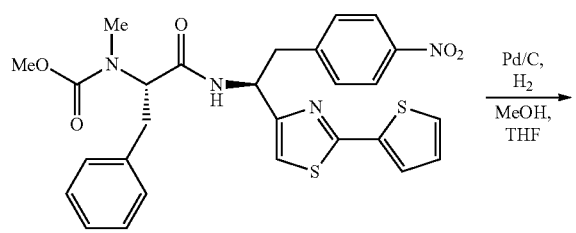

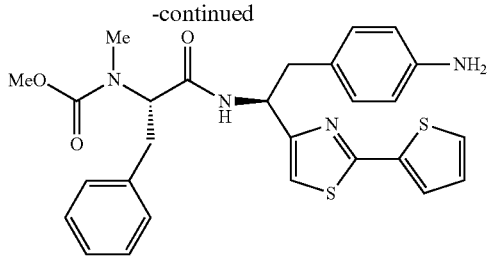

Palladium supported on activated carbon (Pd/C) (5 g) was added to a solution of methyl methyl((S)-1-(((S)-2-(4-nitrophenyl)-1-(2-(thiophen-2-yl)thiazol-4-yl)ethyl)amino)-1-oxo-3-phenylpropan-2-yl)carbamate (24.6 g, 44.7 mmol, 1 eq.) in MeOH (350 mL) and tetrahydrofuran (THF) (30 mL). The resulting suspension was stirred under 0.4 MPa (3.9 atm) of H$_2$ at room temperature for 4 h. Upon the completion of the reaction as indicated by TLC, the reaction mixture was filtered through a pad of Celite. The filtrate was concentrated to dryness to afford crude methyl ((S)-1-(((S)-2-(4-aminophenyl)-1-(2-(thiophen-2-yl)thiazol-4-yl)ethyl)amino)-1-oxo-3-phenylpropan-2-yl)(methyl)carbamate (20.5 g, 88% yield).

HPLC purity: 99.4%; LC-MS: (ES$^+$ m/z) 521 [(M+H)$^+$]; $^1$H NMR (300 MHz, CDCl$_3$) δ 7.51 (d, J=3.3 Hz, 1H), 7.41 (d, J=5.1 Hz, 1H), 7.08-7.24 (m, 5H), 6.85 (d, J=8.1 Hz, 2H), 6.56-6.61 (m, 4H), 5.32-5.25 (m, 1H), 4.72-4.96 (m, 1H), 3.50-3.76 (m, 6H), 3.27-3.34 (m, 1H), 3.1 (m, 2H), 2.71-3.00 (m, 4H).

Preparation of (4-((S)-2-((S)-2-((methoxycarbonyl)(methyl)amino)-3-phenylpropanamido)-2-(2-(thiophen-2-yl)thiazol-4-yl)ethyl)phenyl)sulfamic acid

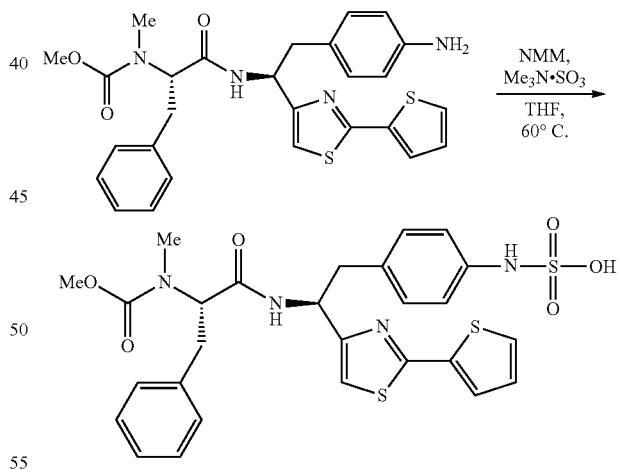

N-Methylmorpholine (NMM) (0.57 g, 5.6 mmol, 2 eq.) and Me$_3$N—SO$_3$ (0.67 g, 4.9 mmol, 1.8 eq.) were added to a solution of crude methyl ((S)-1-(((S)-2-(4-aminophenyl)-1-(2-(thiophen-2-yl)thiazol-4-yl)ethyl)amino)-1-oxo-3-phenylpropan-2-yl)(methyl)carbamate (1.4 g, 2.7 mmol, 1 eq.) in THF (10 mL) at room temperature. The resulting mixture was heated to 60° C. and stirred at 60° C. for 1.5 h. Upon the completion of the reaction as indicated by TLC, the reaction mixture was filtered. The filtrate was concentrated to dryness to afford crude (4-((S)-2-((S)-2-((methoxycarbonyl)(methyl)amino)-3-phenylpropanamido)-2-(2-(thiophen- 2-yl)thiazol-4-yl)ethyl)phenyl)sulfamic acid (2.3 g, 142% yield). The product was used in the next step without further purification.

Preparation of sodium (4-((S)-2-((S)-2-((methoxycarbonyl)(methyl)amino)-3-phenylpropanamido)-2-(2-(thiophen-2-yl)thiazol-4-yl)ethyl)phenyl)sulfamate (Compound 2)

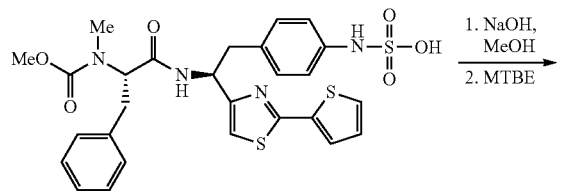

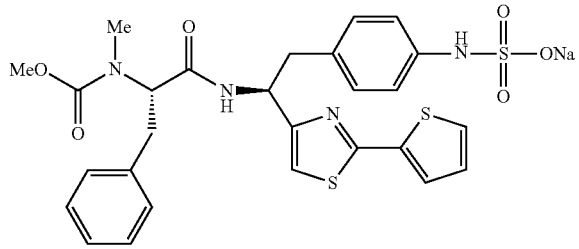

An aqueous solution of NaOH (1.69 g in 2.5 g of H₂O, 42.2 mmol, 1.2 eq.) was added dropwise at room temperature over 10 min to a solution of crude (4-((S)-2-((S)-2-((methoxycarbonyl)(methyl)amino)-3-phenylpropanamido)-2-(2-(thiophen-2-yl)thiazol-4-yl)ethyl)phenyl) sulfamic acid (21.1 g, 35 mmol, 1 eq.) in MeOH (210 mL). The resulting mixture was stirred at room temperature for 1 h. Methyl tert-butyl ether (MTBE) (950 mL) was then added dropwise to the reaction mixture at room temperature over 50 min. A large amount of solid precipitated, and the suspension was stirred at room temperature overnight. The solid was collected by vacuum filtration to afford 11 g of crude sodium (4-((S)-2-((S)-2-((methoxycarbonyl)(methyl) amino)-3-phenylpropanamido)-2-(2-(thiophen-2-yl)thiazol-4-yl)ethyl)phenyl)sulfamate. The crude product was slurried in isopropyl alcohol (100 mL) at room temperature for 5 h. After filtration, sodium (4-((S)-2-((S)-2-((methoxycarbonyl)(methyl)amino)-3-phenylpropanamido)-2-(2-(thiophen-2-yl)thiazol-4-yl)ethyl)phenyl)sulfamate was obtained as an off-white solid (6.5 g, 51% yield).

LC-MS: (ES⁻ m/z) 599 [(M−Na+)⁻]; HPLC purity: 99.5%; ¹H NMR (300 MHz, DMSO-d6) δ 8.41-8.45 (m, 1H) 7.64-7.72 (m, 3H), 7.15-7.25 (m, 7H), 6.91 (m, 4H), 4.82-5.11 (m, 2H), 3.35-3.53 (m, 2H), 3.03-3.18 (m, 2H), 2.77-2.96 (m, 3H), 2.70 (s, 3H).

Example 2: Preparation of Compound 3 as Shown in Table 1

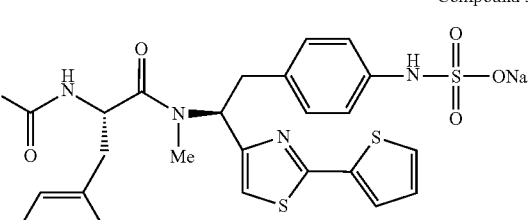

Compound 3

Preparation of (methoxycarbonyl)-L-phenylalanine

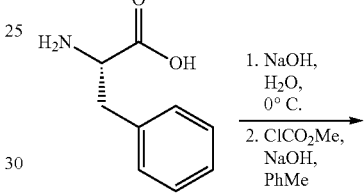

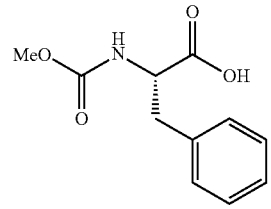

L-Phenylalanine (60 g, 363 mmol, 1.0 eq.), H₂O (300 mL), and an aqueous solution of NaOH (1 mol/L, 240 mL) was added to a 1 L three-necked round-bottomed flask. After cooling to 0° C., a solution of methyl chloroformate (34.4 g, 363 mmol, 1.0 eq.) in toluene (300 mL) and an aqueous solution of NaOH (1 mol/L, 480 mL) were added dropwise to the reaction mixture simultaneously via two addition funnels. The pH of the reaction solution was maintained at 8-9, and the reaction temperature was kept below 10° C. by adjusting the addition rate of both solutions. After the addition was complete, the reaction was stirred at room temperature for 30 min. The reaction mixture was washed with MTBE (50 mL×2), and the aqueous layer was treated with a HCl solution (1 M) to adjust the pH to 3-4. The resulting aqueous solution was extracted with dichloromethane (200 mL×2), dried over anhydrous Na₂SO₄ (100 g), filtered, and concentrated in vacuo to afford crude (methoxycarbonyl)-L-phenylalanine (80 g, 98% yield).

LC-MS: (ES⁺ m/z) 246 [(M+Na)⁺]; ¹H NMR (300 MHz, DMSO-d6) δ 12.73 (s, 1H), 7.52 (d, J=8.4 Hz, 1H), 7.19-7.51 (m, 5H), 4.09-4.17 (m, 1H), 3.46 (s, 3H), 3.02-3.08 (m, 1H), 2.77-2.85 (m, 1H).

Preparation of tert-butyl (S)-(2-(4-nitrophenyl)-1-(2-(thiophen-2-yl)thiazol-4-yl)ethyl)carbamate

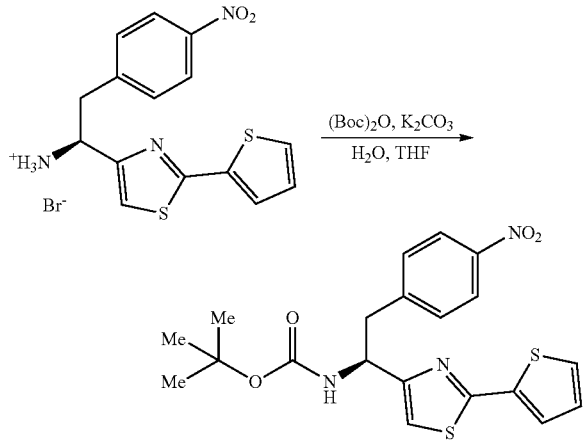

(S)-2-(4-Nitrophenyl)-1-(2-(thiophen-2-yl)thiazol-4-yl) ethan-1-amine hydrobromide (72 g, 174.8 mmol, 1.0 eq.), H$_2$O (650 mL), THF (650 mL), di-tert-butyl dicarbonate ((Boc)$_2$O) (38.12 g, 174.8 mmol, 1.0 eq.), and K$_2$CO$_3$ (36 g, 231.5 mmol, 1.32 eq.) were added to a 1 L three-necked round-bottomed flask. The reaction mixture was stirred at room temperature for about 3 h. After the completion of the reaction as indicated by TLC, the reaction mixture was extracted with EtOAc (500 mL×2), dried over anhydrous Na$_2$SO$_4$ (50 g), filtered, and concentrated in vacuo to yield 81 g of crude product, which was then slurried in n-hexane (80 mL) for 3 h. The solid was collected by vacuum filtration to provide tert-butyl (S)-(2-(4-nitrophenyl)-1-(2-(thiophen-2-yl)thiazol-4-yl)ethyl)carbamate as a white solid (67.9 g, 90% yield).

LC-MS: (ES$^+$ m/z) 432 [(M+H)$^+$]; $^1$H NMR (300 MHz, CDCl$_3$) δ 8.10 (d, J=8.4 Hz, 2H), 7.52 (d, J=5.2 Hz, 1H), 7.44 (d, J=5.2 Hz, 1H), 7.26 (d, J=8.4 Hz, 2H), 7.10-7.13 (m, 1H), 6.74 (s, 1H), 5.35-5.37 (m, 1H), 5.03-5.05 (m, 1H), 3.26-3.39 (m, 2H), 1.50 (s, 9H).

Preparation of tert-butyl (S)-methyl(2-(4-nitrophenyl)-1-(2-(thiophen-2-yl)thiazol-4-yl)ethyl)carbamate

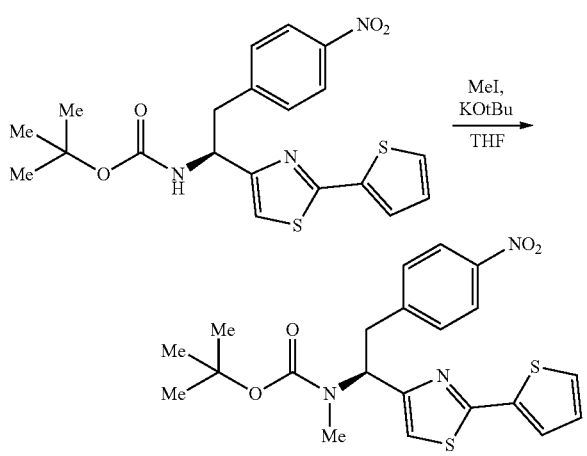

Methyl iodide (9.81 g, 69.6 mmol, 5.0 eq.) was added to a solution of tert-butyl (S)-(2-(4-nitrophenyl)-1-(2-(thiophen-2-yl)thiazol-4-yl)ethyl)carbamate (6 g, 13.92 mmol, 1.0 eq.) in THE (60 mL). Potassium tert-butoxide (3.65 g, 27.84 mmol, 2 eq.) was then added portionwise over 30 min. The completion of the reaction was monitored by TLC (note: the starting material was not consumed completely, and extension of the reaction time would result in more impurities). The reaction was then quenched by water (40 mL). Five parallel reactions at the same scale were carried out, consolidated, and worked up together. The consolidated reaction mixtures were extracted with EtOAc (500 mL×2). The resulting organic phase was dried over anhydrous Na$_2$SO$_4$ (50 g), filtered, and concentrated in vacuo to yield 30 g of a crude product, which was then was purified by silica gel column chromatography (EtOAc:Hexane=1:10) to afford tert-butyl (S)-methyl(2-(4-nitrophenyl)-1-(2-(thiophen-2-yl)thiazol-4-yl)ethyl)carbamate (23.5 g, 76% yield).

LC-MS: (ES$^+$ m/z) 468 [(M+Na)$^+$]; $^1$H-NMR (300 MHz, CDCl$_3$) δ 8.15-8.27 (m, 2H), 7.50-7.80 (m, 4H), 6.90-7.20 (m, 2H), 5.50-5.85 (m, 1H), 3.62-3.75 (m, 1H), 3.25-3.40 (m, 1H), 2.82 (s, 3H), 1.39 (s, 9H).

Preparation of(S)—N-methyl-2-(4-nitrophenyl)-1-(2-(thiophen-2-yl)thiazol-4-yl)ethan-1-amine

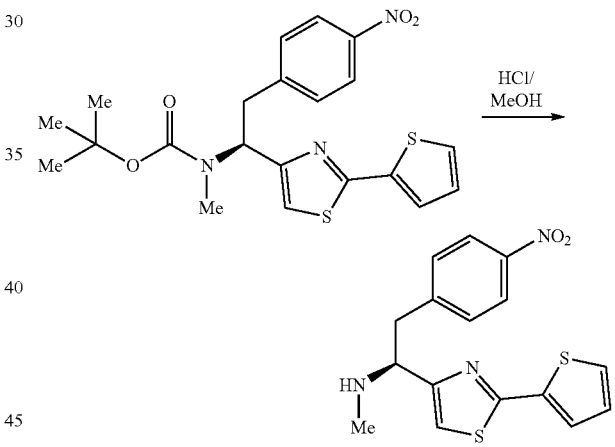

tert-Butyl (S)-methyl(2-(4-nitrophenyl)-1-(2-(thiophen-2-yl)thiazol-4-yl)ethyl)carbamate (27.9 g, 62.7 mmol, 1.0 eq.) was dissolved in a saturated, methanolic HCl solution (160 mL), and stirred at room temperature overnight, whereafter TLC analysis showed complete consumption of starting material. The reaction solution was then concentrated to dryness, and the residue was treated with aqueous K$_2$CO$_3$ solution (2 N, 200 mL) and extracted with dichloromethane (DCM) (200 mL×3). The combined DCM extract was dried over anhydrous Na$_2$SO$_4$, filtered, and concentrated in vacuo to provide crude product (20 g). The crude product was purified by silica gel column chromatography (DCM:MeOH=1:40, 1% triethylamine) to afford (S)—N-methyl-2-(4-nitrophenyl)-1-(2-(thiophen-2-yl)thiazol-4-yl)ethan-1-amine as a yellow oil (17 g, 78.6% yield).

LC-MS: (ES$^+$ m/z) 346 [(M+H)$^+$]; $^1$H NMR (300 MHz, CDCl$_3$) δ 8.09 (d, J=8.4 Hz, 2H), 7.52 (d, J=3.6 Hz, 1H), 7.42 (d, J=5.1 Hz, 1H), 7.26 (d, J=8.4 Hz, 2H), 7.09-7.12 (t, J=4.5 Hz, 1H), 6.78 (s, 1H), 3.93 (t, J=6.9 Hz, 1H), 3.28 (d, J=6.9 Hz, 2H), 2.37 (s, 3H).

Preparation of methyl ((S)-1-(methyl((S)-2-(4-nitrophenyl)-1-(2-(thiophen-2-yl)thiazol-4-yl)ethyl)amino)-1-oxo-3-phenylpropan-2-yl)carbamate

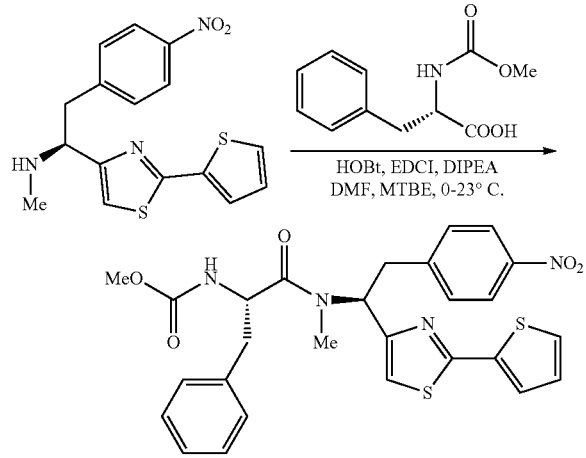

(Methoxycarbonyl)-L-phenylalanine (11.38 g, 51.01 mmol, 1.1 eq.), HOBt (10.67 g, 78.84 mmol, 1.7 eq.), EDCl (13.2 g, 69.56 mmol, 1.5 eq.), and DIPEA (18.02 g, 139.13 mmol, 3 eq.) were added to a solution of (S)—N-methyl-2-(4-nitrophenyl)-1-(2-(thiophen-2-yl)thiazol-4-yl)ethan-1-amine (16 g, 46.38 mmol, 1 eq.) in DMF (370 mL) and MTBE (135 mL) at 0° C. The resulting mixture was stirred at 0° C. for 30 min and at room temperature overnight. The completion of the reaction was monitored by TLC. When the starting material was consumed, the reaction mixture was quenched by water (400 mL) and extracted with EtOAc (300 mL×3). The combined organic phase was washed with aqueous HCl (1 M, 200 mL), followed by 5% NaHCO₃ solution (200 mL) and water (200 mL). The organic layer was dried over anhydrous Na₂SO₄, filtered, and concentrated in vacuo to yield 28 g of crude product, which was then slurried in a mixture of solvents (MTBE:EtOAc=1:1, 50 mL) for 1 h, and filtered to afford ((S)-1-(methyl((S)-2-(4-nitrophenyl)-1-(2-(thiophen-2-yl)thiazol-4-yl)ethyl)amino)-1-oxo-3-phenylpropan-2-yl)carbamate as a yellow solid (22 g, 86% yield).

LC-MS: (ES⁺ m/z) 551 [(M+H)⁺]; ¹H NMR (300 MHz, CDCl₃) δ 8.09 (d, J=8.4 Hz, 2H), 7.52 (d, J=3.0 Hz, 1H), 7.43 (d, J=4.5 Hz, 1H), 7.37 (d, J=8.4 Hz, 2H), 7.09-7.18 (m, 6H), 6.64 (s, 1H), 6.14 (t, J=7.5 Hz, 1H), 5.35-5.50 (m, 1H), 4.80 (m, 1H), 3.66 (s, 3H), 3.58-3.65 (m, 1H), 3.15-3.28 (m, 1H), 2.94-2.96 (m, 2H), 2.72 (s, 3H).

Preparation of methyl ((S)-1-(((S)-2-(4-aminophenyl)-1-(2-(thiophen-2-yl)thiazol-4-yl)ethyl)(methyl)amino)-1-oxo-3-phenylpropan-2-yl)carbamate

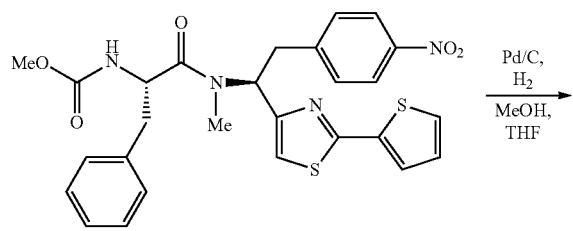

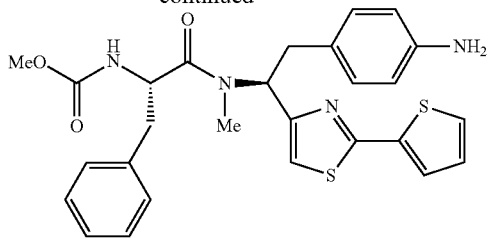

Pd/C (4.4 g, 10%) was added to a solution of ((S)-1-(methyl((S)-2-(4-nitrophenyl)-1-(2-(thiophen-2-yl)thiazol-4-yl)ethyl)amino)-1-oxo-3-phenylpropan-2-yl)carbamate (22 g, 40 mmol, 1 eq.) in MeOH (300 mL) and THF (400 mL). The reaction was stirred at room temperature under 0.4 MPa (3.9 atm) of H₂ for 4.5 h, whereafter TLC analysis indicated the complete consumption of starting material. The reaction mixture was then filtered through a pad of Celite. The filtrate was concentrated to dryness to afford 25.5 g of crude product, which was then purified by silica gel column chromatography (MeOH:DCM=1:10, 1% triethylamine) to provide methyl ((S)-1-(((S)-2-(4-aminophenyl)-1-(2-(thiophen-2-yl)thiazol-4-yl)ethyl)(methyl)amino)-1-oxo-3-phenylpropan-2-yl)carbamate (20 g, 96% yield).

LC-MS: (ES⁺ m/z) 521 [(M+H)⁺]; HPLC purity: 95.4%; ¹H NMR (300 MHz, CDCl₃) δ 7.52 (d, J=3.6 Hz, 1H), 7.43 (d, J=5.1 Hz, 1H), 7.03-7.15 (m, 6H), 6.98 (d, J=8.4 Hz, 2H), 6.72 (s, 1H), 6.56 (d, J=8.4 Hz, 2H), 6.01 (t, J=7.5 Hz, 1H), 5.40-5.50 (m, 1H), 4.80 (m, 1H), 3.69 (s, 3H), 3.50-3.69 (m, 3H), 3.30-3.38 (m, 1H), 2.94-2.96 (m, 4H), 2.74 (s, 3H).

Preparation of sodium (4-((S)-2-((S)-2-((methoxycarbonyl)amino)-N-methyl-3-phenylpropanamido)-2-(2-(thiophen-2-yl)thiazol-4-yl)ethyl)phenyl)sulfamate (Compound 3)

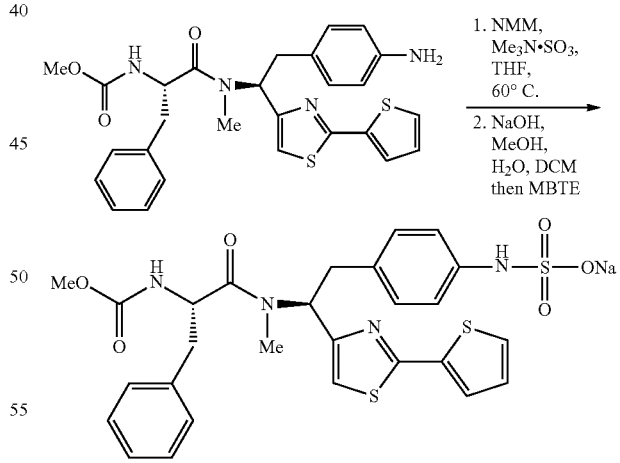

NMM (3.11 g, 30.73 mmol, 2 eq.) and Me₃NSO₃ (3.21 g, 23.08 mmol, 1.5 eq.) were added to a solution of methyl ((S)-1-(((S)-2-(4-aminophenyl)-1-(2-(thiophen-2-yl)thiazol-4-yl)ethyl)(methyl)amino)-1-oxo-3-phenylpropan-2-yl)carbamate (8 g, 15.38 mmol, 1 eq.) in THF (80 mL). The resulting mixture was heated to 60° C. and stirred for 1.5 h, whereafter TLC analysis showed complete consumption of starting material. The reaction was concentrated to dryness, and the resulting residue was then dissolved in a mixture of solvents (MeOH:H₂O:DCM=4:1:2, 70 mL). A 40% aqueous NaOH solution (3.07 g, 30.73 mmol, 2.0 eq.) was then added to the resulting solution dropwise at room temperature over 30 min. After the addition, the reaction was stirred at room temperature for 1 h. MTBE (650 mL) was then added dropwise over 5 h, and the resulting suspension was stirred at room temperature overnight. The suspension was filtered, and the filter cake was slurried in IPA (50 mL) at room temperature overnight. After filtration, sodium (4-((S)-2-((S)-2-((methoxycarbonyl)amino)-N-methyl-3-phenylpropanamido)-2-(2-(thiophen-2-yl)thiazol-4-yl)ethyl)phenyl) sulfamate was obtained (6.3 g, 65.8% yield).

LC-MS: (ES⁻ m/z) 599 [(M–Na⁺)⁻]; HPLC purity: 99.8%; ¹H NMR (300 MHz, CD₃OD) δ 7.54-7.56 (m, 2H), 7.00-7.40 (m, 11H), 5.97 (t, J=7.2 Hz, 0.66H), 5.50-5.55 (m, 0.37H), 4.76-4.78 (m, 1H), 3.70-3.65 (s, 3H).

Example 3: Preparation of Compound 4 as Shown in Table 1

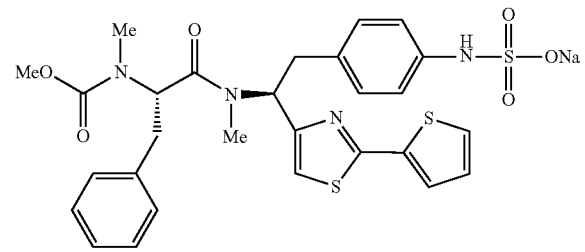

Compound 4

Preparation of (S)—N-(2,4-dimethoxybenzyl)-N-methyl-2-(4-nitrophenyl)-1-(2-(thiophen-2-yl)thiazol-4-yl)ethan-1-amine

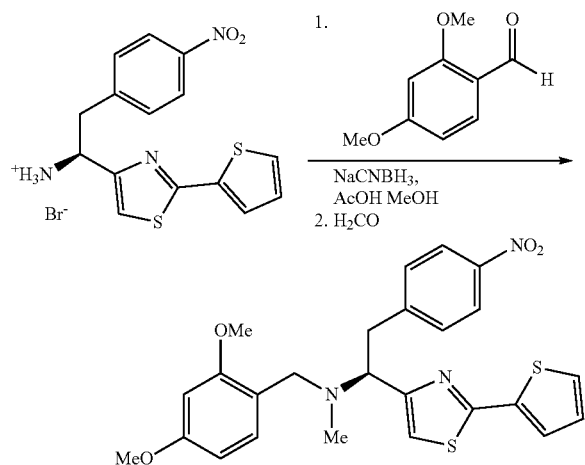

2,4-Dimethoxybenzaldehyde (DMB) (7 g, 42.2 mmol, 1.0 eq.), NaCNBH₃ (8.7 g, 138.4 mmol, 3.3 eq.), and acetic acid (8.7 mL) were added to a solution of (S)-2-(4-nitrophenyl)-1-(2-(thiophen-2-yl)thiazol-4-yl)ethan-1-amine hydrobromide (17.4 g, 42.2 mmol, 1.0 eq.) in MeOH (180 mL). The resulting mixture was stirred at room temperature for about 1 h, whereafter TLC analysis indicated ~50% consumption of starting material. An additional aliquot of DBM (0.7 eq.) and then NaCNBH₃ (1 eq.) were added portionwise until the complete consumption of starting material was achieved (~3 h). An aqueous solution of formaldehyde (37%, 3.7 g) was then added in one portion, and the resulting mixture was stirred at room temperature for 30 min, whereafter TLC analysis indicated the complete consumption of the monoalkylated amine intermediate. The reaction was quenched by water (500 mL), and the pH was adjusted to 7-8 with saturated NaHCO₃ solution. The reaction mixture was extracted with DCM (200 mL×3), and the combined organic phases were dried over anhydrous Na₂SO₄ (50 g), filtered, and concentrated in vacuo to yield 30 g of crude product. The crude product was purified by silica gel column chromatography (EtOAc:Petroleum ether=1:10, 1% triethylamine) to provide (S)—N-(2,4-dimethoxybenzyl)-N-methyl-2-(4-nitrophenyl)-1-(2-(thiophen-2-yl)thiazol-4-yl)ethan-1-amine as a white solid (19 g, 90% yield).

LC-MS: (ES⁺ m/z) 496 [(M+H)⁺]; ¹H NMR (300 MHz, CDCl₃) δ 8.06 (d, J=8.4 Hz, 2H), 7.52 (d, J=3.3 Hz, 1H), 7.41 (d, J=4.8 Hz, 1H), 7.26 (d, J=8.4 Hz, 2H), 7.08-7.17 (m, 2H), 6.90 (s, 1H), 6.40-6.49 (m, 2H), 4.09 (t, J=7.2 Hz, 1H), 3.70-3.90 (m, 6H), 3.40-3.60 (m, 4H), 2.32 (s, 3H).

Preparation of (S)—N-methyl-2-(4-nitrophenyl)-1-(2-(thiophen-2-yl)thiazol-4-yl)ethan-1-amine

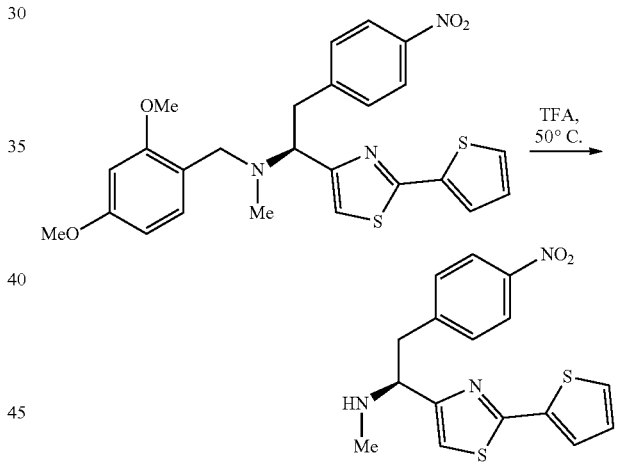

A solution of (S)—N-(2,4-dimethoxybenzyl)-N-methyl-2-(4-nitrophenyl)-1-(2-(thiophen-2-yl)thiazol-4-yl)ethan-1-amine (19 g, 38.3 mmol) in trifluoroacetic acid (TFA) (100 mL) was stirred at 50° C. for 2 h, whereafter TLC analysis indicated the complete consumption of starting material. The reaction mixture was then concentrated to dryness under vacuum, and the residue was treated with aqueous K₂CO₃ solution (2 N, 50 mL) and 200 mL of DCM. After phase separation, the aqueous layer was extracted with DCM (200 mL×3). The combined organic layers were dried over anhydrous Na₂SO₄, filtered, and concentrated in vacuo to yield 15 g of crude product, which was then purified by silica gel column chromatography (MeOH:DCM=1:40, 1% triethylamine) to afford (S)—N-methyl-2-(4-nitrophenyl)-1-(2-(thiophen-2-yl)thiazol-4-yl)ethan-1-amine as a yellow oil (11 g, 83% yield).

LC-MS: (ES⁺ m/z) 346 [(M+H)⁺]; HPLC purity: 98.6%; ¹H NMR (300 MHz, CDCl₃) δ 8.09 (d, J=8.4 Hz, 2H), 7.52 (d, J=3.6 Hz, 1H), 7.42 (d, J=5.1 Hz, 1H), 7.26 (d, J=8.4 Hz, 2H), 7.09-7.12 (t, J=4.5 Hz, 1H), 6.78 (s, 1H), 3.93 (t, J=6.9 Hz, 1H), 3.28 (d, J=6.9 Hz, 2H), 2.37 (s, 3H).

Preparation of methyl methyl((S)-1-(methyl((S)-2-(4-nitrophenyl)-1-(2-(thiophen-2-yl)thiazol-4-yl)ethyl)amino)-1-oxo-3-phenylpropan-2-yl)carbamate

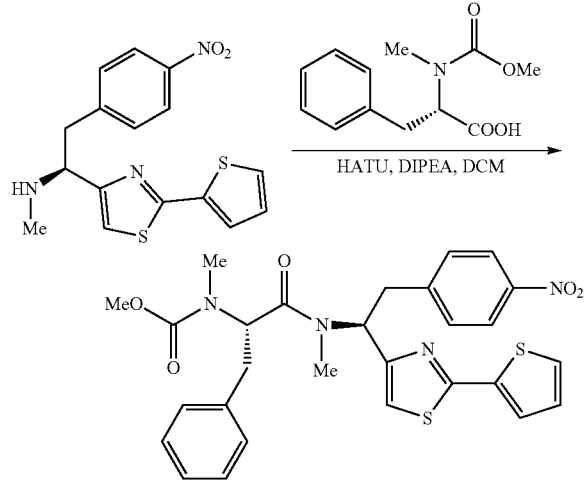

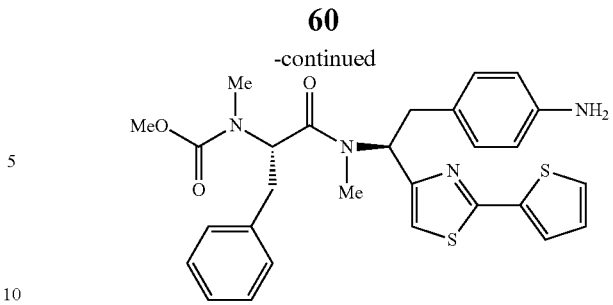

N-(Methoxycarbonyl)-N-methyl-L-phenylalanine (12.14 g, 51.01 mmol, 1.1 eq.), 1-[bis(dimethylamino)methylene]-1H-1,2,3-triazolo[4,5-b]pyridinium 3-oxide hexafluorophosphate (HATU) (23.53 g, 60.29 mmol, 1.3 eq.), and DIPEA (18. g, 139 mmol, 3 eq.) were added to a solution of (S)—N-methyl-2-(4-nitrophenyl)-1-(2-(thiophen-2-yl)thiazol-4-yl)ethan-1-amine (16 g, 46.38 mmol, 1 eq.) in DCM (160 mL). The reaction mixture was stirred at room temperature overnight, whereafter TLC analysis indicated the complete consumption of starting material. The reaction was quenched with water (400 mL) and extracted with EtOAc (200 mL×2). The combined organic phases were washed with a dilute HCl solution (1 mol/L, 200 mL), followed by 5% aqueous NaHCO₃ solution (200 mL) and water (200 mL). The organic phase was dried over anhydrous Na₂SO₄ (50 g), filtered, and concentrated in vacuo to yield 28 g of crude product, which was then purified by silica gel column chromatography (MeOH:DCM=1:40, 1% triethylamine) to provide methyl methyl((S)-1-(methyl((S)-2-(4-nitrophenyl)-1-(2-(thiophen-2-yl)thiazol-4-yl)ethyl)amino)-1-oxo-3-phenylpropan-2-yl)carbamate as a yellow oil (25 g, 95.5% yield).

LC-MS: (ES⁺ m/z) 565 [(M+H)⁺].

Preparation of methyl ((S)-1-(((S)-2-(4-aminophenyl)-1-(2-(thiophen-2-yl)thiazol-4-yl)ethyl)(methyl)amino)-1-oxo-3-phenylpropan-2-yl)(methyl)carbamate

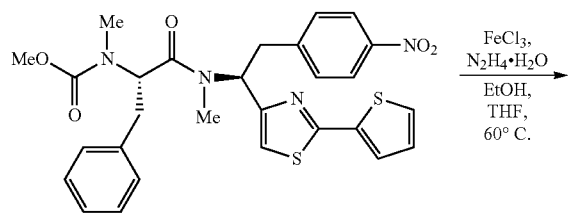

FeCl₃ (1.32 g, 8.16 mmol, 0.2 eq.) and N₂H₄·H₂O (65 g, 1.3 mol, 32 eq.) were added to a solution of methyl methyl ((S)-1-(methyl((S)-2-(4-nitrophenyl)-1-(2-(thiophen-2-yl)thiazol-4-yl)ethyl)amino)-1-oxo-3-phenylpropan-2-yl)carbamate (23 g, 40.78 mmol, 1 eq.) in ethanol (920 mL) and THF (200 mL). The reaction mixture was then stirred at 60° C. overnight, whereafter TLC analysis showed the consumption of the starting material. The reaction mixture was then filtered, and the filtrate was concentrated to dryness to provide 20 g of crude methyl ((S)-1-(((S)-2-(4-aminophenyl)-1-(2-(thiophen-2-yl)thiazol-4-yl)ethyl)(methyl)amino)-1-oxo-3-phenylpropan-2-yl)(methyl)carbamate, which was used for the next step without any further purification.

LC-MS: (ES⁺ m/z) 535 [(M+H)⁺]; HPLC purity: 96.5%.

Preparation of sodium (4-((S)-2-((S)-2-((methoxycarbonyl)(methyl)amino)-N-methyl-3-phenylpropanamido)-2-(2-(thiophen-2-yl)thiazol-4-yl)ethyl)phenyl)sulfamate (Compound 4

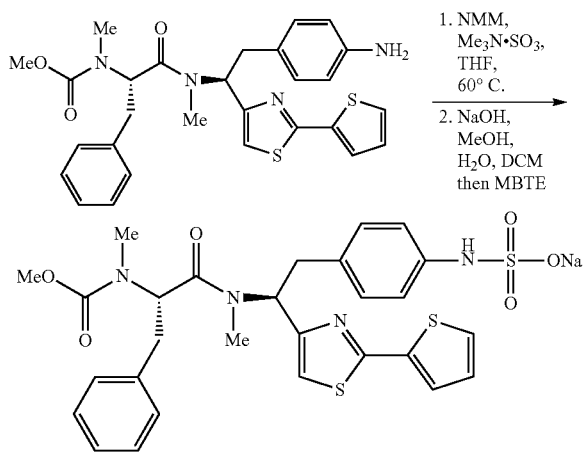

NMM (3.11 g, 29.96 mmol, 2 eq.) and Me₃NSO₃ (3.21 g, 22.47 mmol, 1.5 eq.) were added to a solution of methyl ((S)-1-(((S)-2-(4-aminophenyl)-1-(2-(thiophen-2-yl)thiazol-4-yl)ethyl)(methyl)amino)-1-oxo-3-phenylpropan-2-yl)(methyl)carbamate (8 g, 14.98 mmol, 1 eq.) in THF (80 mL). The resulting mixture was stirred at 60° C. for about 1.5 h, whereafter TLC analysis indicated complete consumption of the starting material. The reaction mixture was concentrated to dryness and dissolved in a mixture of solvents (MeOH:H₂O:DCM=4:1:2, 70 mL). 40% aqueous NaOH solution (3.0 g, 30.73 mmol, 2.0 eq.) was added dropwise to the solution and the resulting mixture was stirred at room temperature for 1 h. MTBE (650 mL) was then added dropwise to the solution over 5 h. A large amount of solid was observed to precipitate during the addition. The resulting suspension was stirred at room temperature overnight, and the solid was collected by vacuum filtration. The isolated solid was slurried in IPA (50 mL) overnight, and the resulting suspension was filtered to provide 8.8 g of sodium (4-((S)-2-((S)-2-((methoxycarbonyl)(methyl)amino)-N-methyl-3-phenylpropanamido)-2-(2-(thiophen-2-yl)thiazol-4-yl)ethyl)phenyl)sulfamate as a white solid (8.8 g, 92% yield).

LC-MS: (ES$^-$ m/z) 613 [(M–Na$^+$)$^-$]; HPLC purity: 99%.

Example 4: Water Solubility, and Solution, Physical, and Chemical Stability of Compounds 2-4

Solubility Testing of Compounds 2-4 as Shown in Table 1.

The solubility of compounds 2-4 was determined by portionwise addition of the compounds to water until saturation was obtained. Water (10 mL) was added to a 20-mL vial. About 100 mg of Compound 2 was added. The suspension was stirred at room temperature for 20 minutes until the contents became a clear solution. Compound 2 (~100 mg portionwise) was added repeatedly with 30 min stirring time between the additions. Once a suspension was obtained after continuous stirring for 2 hours, the suspension was stirred overnight. The same procedure was used for the suspension preparations of Compound 3 and Compound 4. The results are summarized in TABLE 2.

TABLE 2

|  | Compound | | |
| --- | --- | --- | --- |
|  | 2 | 3 | 4 |
| Amount (g) | 2.528 | 2.323 | 0.624 |
| Physical appearance | Precipitate | No precipitate (too viscous to stir) | Precipitate |
| Filtration | Yes | No | Yes |
| T = 0 | Clear | Hazy | Clear |
| T = 1 day | Clear | Hazy | Clear |
| T = 2 day | Clear | Hazy | Clear |
| T = 3 day | Slightly hazy | Hazy | Clear |
| T = 4 day | Small precipitate | Hazy | Clear |
| T = 5 day | Small precipitate | Hazy | Clear |
| T = 6 day | Precipitate | Hazy | Clear |
| T = 2 week | Precipitate | Hazy | Clear |
| T = 3 week | Precipitate | Hazy | Clear |
| T = 4 week | Precipitate | Hazy | Clear |

All three methylated analogues demonstrated high water solubility compared to Compound 1. Compound 2 formed a suspension after 2.53 g were added to 10 mL of water. Compound 3 did not give a suspension after 2.323 g of the solid were added, but gave a hazy, highly viscous mixture. Compound 4 formed a suspension after 0.624 g of the solid was added. After stirring overnight, filtration of each sample was attempted. Due to differences in viscosity, filtration of Compound 4 proceeded readily whereas filtration of Compound 2 was difficult and Compound 3 was not filtered successfully.

No gelation or precipitation was observed throughout the 4-week study period for Compound 3 or Compound 4. However, the solution of Compound 2 started to show some haziness after 3 days at room temperature, and gradually developed a precipitate over 5 weeks. An aliquot of the suspension of Compound 2 was filtered through a 0.22 micron inline syringe filter. The concentration of Compound 2 in the clear filtrate was determined to be 49.5 mg/mL, which was 25% of the concentration of the initial, supersaturated solution.

About 1 mL of the aqueous solutions prepared above was diluted with water by 50%. The pH of the 50% diluted solutions was adjusted to pH 7 either by 0.1 N HCl or by 0.1 N NaOH. Solubility values for the three compounds in the solutions/suspensions before and after dilution are given in the in TABLE 3.

TABLE 3

|  | Compound | | |
| --- | --- | --- | --- |
|  | 2 | 3 | 4 |
| Before dilution T = 0 | ~250 mg/mL* (suspension) | >230 mg/mL (viscous solution) | 62 mg/mL (solution) |
| Before dilution T = 5 weeks | 49.5 mg/mL** | No change* | No change* |
| 50% dilution T = 4 weeks | ~125 mg/mL* (solution) *** | >115 mg/mL* (solution) | 31 mg/mL* (solution) |

*Concentration estimated based on weight of compound added.
**Concentration determined versus standard curve.
***Some precipitate was observed after 2.5 months.

Syringability testing was carried out by applying 200 g of weight on top of a BD 1-mL syringe plunger and measuring the time required to expel 1 mL of the saturated solutions through a 27 G needle. The times are recorded in TABLE 4. At T=0, 43 seconds were required to expel 1 mL of Compound 2, while 8 seconds were required to expel 1 mL of Compound 4. In contrast, approximately 5 minutes were required to expel only 0.1 mL of Compound 3, based on the very high viscosity of the solution relative to that of the other two. After a small increase from T=0 to T=1 day, Compound 4 showed very consistent syringability times at multiple time points over 4 weeks.

TABLE 4

|  | Compound | | |
| --- | --- | --- | --- |
|  | 2 | 3 | 4 |
| T = 0 | 43 sec | ~5 min* | 8 sec |
| T = 1 day | 52 sec | ND** | 12 sec |
| T = 2 day | 65 sec | ND | 15 sec |
| T = 3 day | 58 sec | ND | 12 sec |
| T = 4 day | ND | ND | 13 sec |
| T = 5 day | ND | ND | 14 sec |
| T = 6 day | ND | ND | 14 sec |
| T = 2 week | ND | ND | 13 sec |
| T = 3 week | ND | ND | 12 sec |
| T = 4 week | ND | ND | 13 sec |

*Only 0.1 mL of the solution was ejected in 5 min.
**ND = not determined.

The 50% diluted solutions showed no precipitation or gelation while standing at room temperature for 4 weeks. Syringability test results of the 50% diluted solutions (TABLE 5) indicated a slight increase in viscosity (syringability test for water was 10 sec). All three solutions remained easily syringable.

TABLE 5

|  | Compound | | |
| --- | --- | --- | --- |
|  | 2 | 3 | 4 |
| T = 0 | ND* | ND | ND |
| T = 1 day | ND | ND | ND |
| T = 2 day | 10 sec | 13 sec | 12 sec |
| T = 3 day | 15 sec | 14 sec | 14 sec |
| T = 4 day | 18 sec | 17 sec | 15 sec |

TABLE 5-continued

|  | Compound | | |
|---|---|---|---|
|  | 2 | 3 | 4 |
| T = 5 day | ND | ND | ND |
| T = 6 day | ND | ND | ND |
| T = 7 day | 15 sec | 15 sec | 12 sec |
| T = 2 week | 14 sec | 12 sec | 13 sec |
| T = 3 week | 11 sec | 13 sec | 13 sec |
| T = 4 week | 11 sec | 15 sec | 14 sec |

*ND = not determined.

HPLC purity analyses of the undiluted samples over 5 weeks at room temperature showed a decrease in purity to 97.3% for Compound 3 and 96.53% for Compound 4 in 5 weeks at room temperature (TABLE 6). Greater degradation of Compound 2 to 88.99% purity was seen at 5 weeks. This decrease in purity led to reanalysis of the Compound 2 sample after 7 weeks, which gave increased purity (93.9%) in two separate analyses. HPLC purity analyses of the 50% diluted samples showed a similar decrease in purity to 97.9% for Compound 3 and to 97.69% for Compound 4 in 4 weeks at room temperature (TABLE 7). Degradation was observed for Compound 2 with purity at 82%. Reanalysis of the Compound 2 sample after 6 weeks showed an increase in purity (96.9%) in two separate analyses.

TABLE 6

|  | Compound | | |
|---|---|---|---|
|  | 2 | 3 | 4 |
| T = 0 (dry sample) | 99.59% | 99.08% | 98.72% |
| T = 1 day | 98.7% | 98.26% | 98.2% |
| T = 5 weeks | 88.99% | 97.3% | 96.53% |
| T = 7 weeks | 93.93% | ND | ND |

TABLE 7

|  | Compound | | |
|---|---|---|---|
|  | 2 | 3 | 4 |
| T = 4 weeks | 82% | 97.9% | 97.69% |
| T = 6 weeks | 96.95% | ND | ND |

Figure 2:
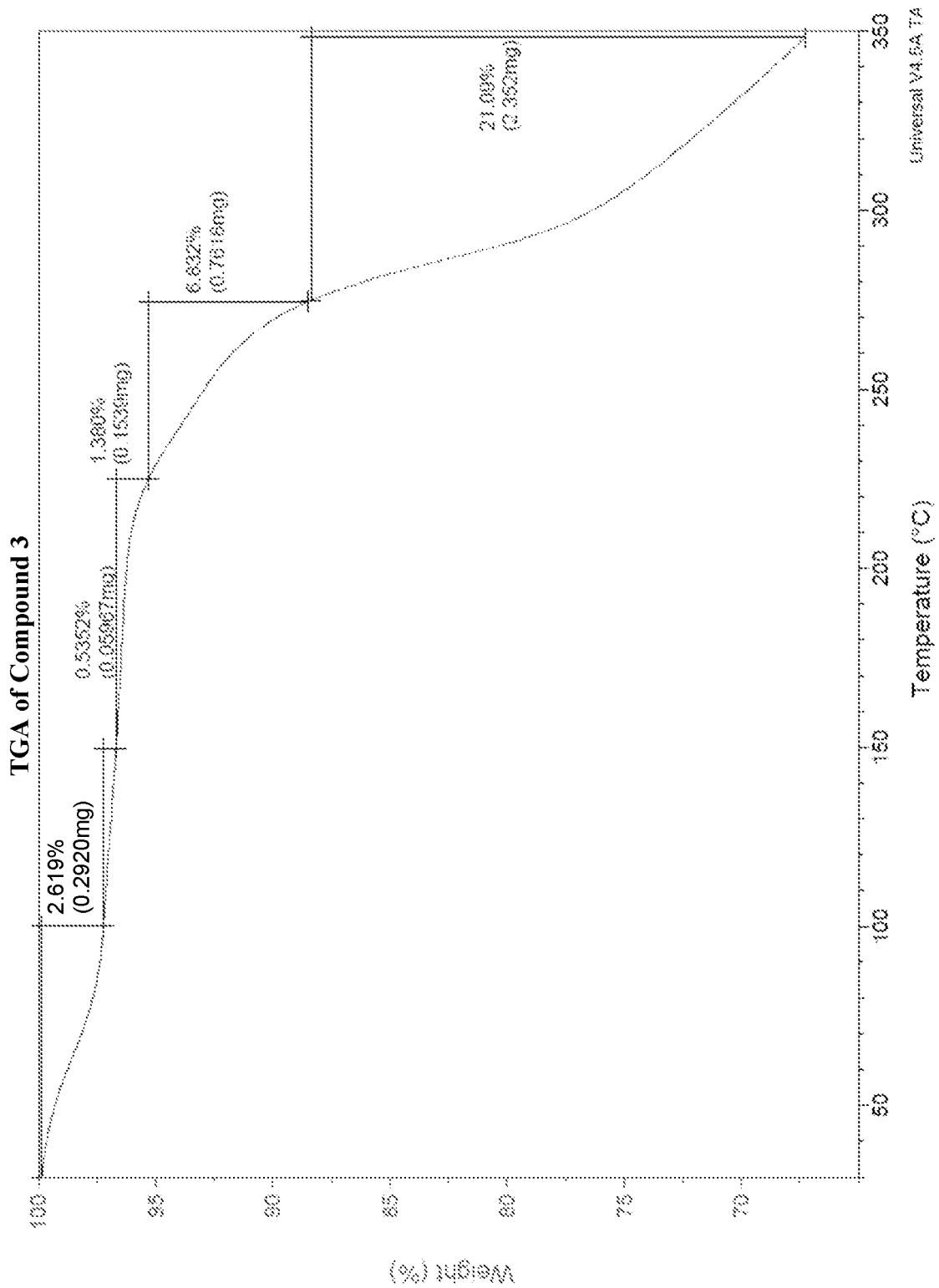
FIG. 2 illustrates the TGA thermogram of Compound 3.

Thermogravimetric (TGA) analysis was performed on Compound 2 and Compound 3, and the results are summarized in FIG. 1 and FIG. 2, respectively. Compound 2 and Compound 3 both showed about a 3% weight loss below 150° C., with significant further weight loss observed at above 200° C. The melting points of Compound 2, Compound 3, and Compound 4 were 152-175, 150-180, and 146-170° C., respectively.

Conclusions.

The solubility of Compounds 2-4 was determined by portionwise addition of the compounds to water until saturation was obtained. After stirring overnight, the suspensions were filtered and analyzed by HPLC. Compound 2 demonstrated initial solubility at about 200 mg/mL (oversaturation), and fell to about 50 mg/mL in 5 weeks. The solubility of Compound 3 was >200 mg/mL. The absolute solubility of Compound 3 was not determined because in the course of analysis, the solution of Compound 3 became too viscous to stir. The solubility of Compound 4 was about 58 mg/mL. Solutions of Compound 2 and Compound 4 were syringable but solutions of Compound 3 were too viscous to syringe. The 50% diluted solutions of Compounds 2-4 were not viscous, and the compounds remained in solution for 4 weeks. Precipitation was observed for Compound 2 after about 2.5 months at room temperature. All of the diluted solutions were easily syringable over 4 weeks' time.

Example 5: Evaluation of Compounds 2-4 for Activation of Phospho-Akt in Human Umbilical Vein Endothelial Cells The ability of the small molecule analogues as shown in EXAMPLES 1-3 to stimulate production of phospho-Akt1 (pAkt) was tested. Akt plays a critical role in controlling cell survival and apoptosis, and Akt phosphorylation is increased by the activation of Tie-2. Akt activation can be detected by an antibody that recognizes phosphorylation on the serine 473 residue on Akt.

Material Methods and Experimental Design

Phospho-Akt Activation Assay

Human Umbilical Vein Endothelial Cell Maintenance.

HUVECs were seeded at 500,000 cells/mL in chemically-defined basal media, and supplemented with distinct growth factors (EGM-2). The following growth factors were required for survival and normal phenotypic expression of endothelial characteristics: fetal bovine serum 2%, hydrocortisone, human fibroblast growth factor-B, vascular endothelial growth factor, recombinant insulin growth factor R3, ascorbic acid, human epidermal growth factor, gentamicin sulfate, amphotericin B, and heparin. Cells were derived from one female donor, cultivated in 10 cm dishes, and expanded upon reaching 90% confluence. After three passages, the cells were expanded and ready for testing.

Endothelial Cell Preparation, Treatment, and Cell Lysis.

The cells were seeded at 25,000 cells/mL in 6-well plates, and covered with 2 mL of complete media. The cells were fed on day 2 of culture with 2 mL of fresh EGM-2 media. 72 hours after plating, the cells were serum starved by rinsing twice with 2 mL of sterile phosphate buffered saline, and then placed at 37° C. for 3 hours in the presence of basal EGM-2 media (1.5 mL/well without growth factors). The serum starvation allowed the cells to become quiescent.

Compounds 2-4 were dissolved in distilled deionized water at the following concentrations:

Compound 2 (Molecular weight: 622.7): 31 mg/ml.
Compound 3 (Molecular weight: 622.7): 26 mg/ml.
Compound 4 (Molecular weight: 636.7): 32 mg/ml.

All compounds were stored at 4° C. Upon addition of water to Compound 4, the resulting solution exhibited a slightly milky appearance, and cleared within 5 minutes at room temperature. Stock concentrations of the above molecules were made at a final working concentration of 1 mM. Specific microliter volumes of the working concentration were added to each 6 well plate at the following concentrations: 3, 10, and 30 micromolar (µM). Cells were treated for 30 minutes.

Lysis Buffer and Protease Inhibitor Preparation.

10× cell lysis buffer was diluted fresh with $dH_2O$. The 1× cell lysis buffer contained: 20 mM Tris-HCl (pH 7.5), 150 mM NaCl, 1 mM $Na_2$EDTA, 1 mM EGTA, 1% Triton, 2.5 mM sodium pyrophosphate, 1 mM β-glycerophosphate, 1 mM $Na_3VO_4$, 1 µg/ml leupeptin, and 1 mM PMSF. Immediately before use, 1 mM PMSF was prepared by diluting from a stock of 1 M PMSF made up in DMSO. In addition, a 1× concentration of a Halt protease & phosphatase inhibitor cocktail was included. At the end of the 30 minute treatment, the media was discarded from the cell culture wells by shaking out, and the remaining media was aspirated off the wells. Ice-cold lysis buffer was added at 140 μL/well, and the culture was placed on ice or in a cold room for 30 minutes while rocking. Cell lysates were collected using a cell scraper, placed in microfuge tubes, and stored at −80° C. The levels of protein were quantitated using a microtiter plate BCA protein assay.

Protein Electrophoresis and Blotting.

2× Laemmli sample buffer was added in equal volume to the 10× cell lysis buffer, which contained the lysed endothelial cells. The solution was heated at 100° C. for 5 minutes and then sonicated for 10 seconds. After sonication, the lysates were spun by centrifuge at 4° C. for 5 minutes at 17,000 rpm. 70-100 μg of protein calculated from BCA assay prior to addition of 2× Laemmli sample were added per well of an 8% polyacrylamide gel.

Electrophoresis was performed at 150 volts for approximately 90 minutes at room temperature with 1× Laemmli running buffer. The proteins from the gel were transferred to nitrocellulose at 100 volts for 45 minutes on ice.

The nitrocellulose membranes were removed quickly without drying and placed in phosphate buffered saline (pH 7.3) with 1% nonfat dried milk. The membranes were blocked in the milk solution while rocking for 2 hours at room temperature or overnight at 4° C. A rabbit mAb primary antibody directed against pAkt (Ser473) was added at a concentration of 1:2,000 in blocking solution at approximately 15 mL/blot. For total Akt levels, an antibody against Akt was used at 1:1,000 in blocking buffer. Incubation was done for two hours at room temperature or overnight at 4° C. The membranes were washed three times for 5 minutes while rocking with 20 mL of PBS.

A secondary antibody (donkey anti-rabbit) was added at 1:2,500 in blocking buffer and incubated with the membranes for 1 hour at room temperature while rocking. The membranes were washed as before with PBS and then developed to determine levels of pAkt. For quantification, the data were expressed above control as a percentage of density compared to controls and negative controls. The standard error of the method was less than 5%.

Results

Effects of Compounds 2-4 on Levels of Phospho-Akt in HUVECs.

Figure 3:
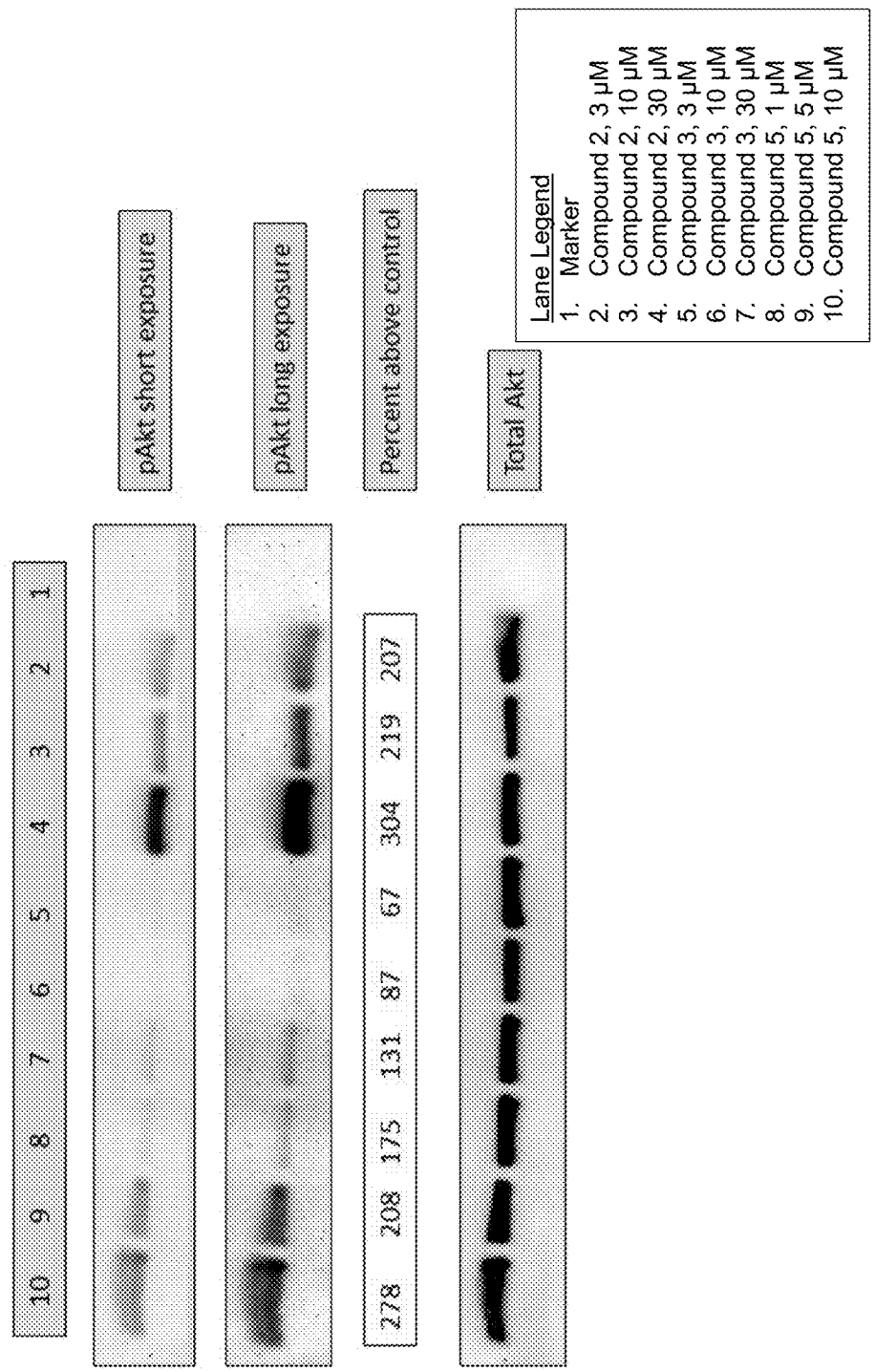
FIG. 3 illustrates pAkt activity in human umbilical vein endothelial cells in the presence of Compound 2 and Compound 3.
Figure 4:
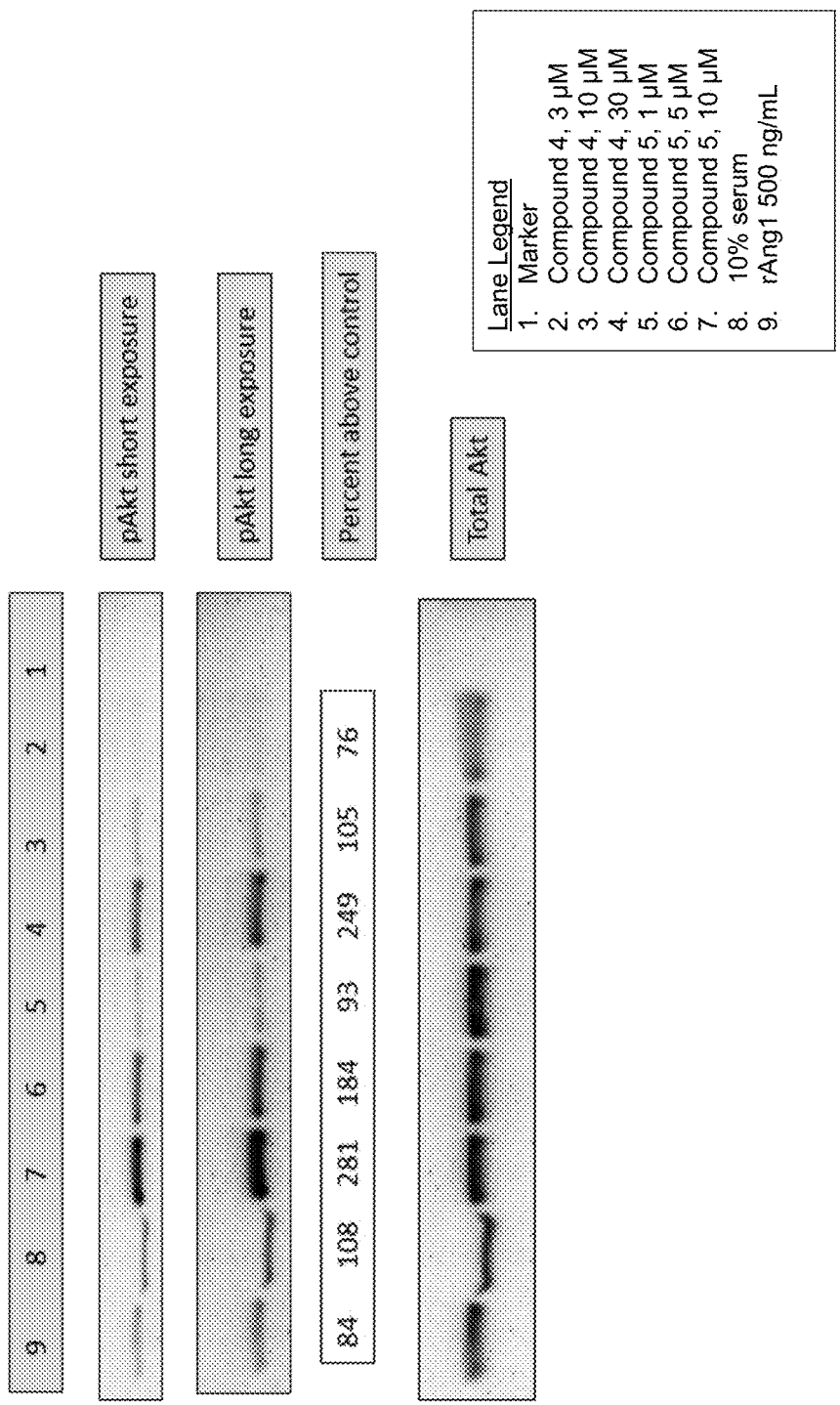
FIG. 4 illustrates pAkt activity in human umbilical vein endothelial cells in the presence of Compound 4 and Compound 5.

The levels of pAkt are shown in FIGS. 3 and 4. Noticeable and dose-dependent levels of pAkt were observed with Compound 2, with the 30 μM concentration resulting in a 300% signal above control. With respect to Compound 3, the 30 μM concentration resulted in an 80% signal above control. Compound 5 was included as a positive control, and gave reproducible results in two separate experiments, where the highest dose (10 μM) was observed to produce pAkt levels 278% above control. Overall, the relative potencies for activation of pAkt were Compound 2>Compound 4>Compound 3. However, noticeable and reproducible levels of pAkt were present above control at the 30 μM concentration in each set. Consistent levels of total Akt observed across samples indicated equal loading occurred in each sample tested.

EMBODIMENTS

The following non-limiting embodiments provide illustrative examples of the invention, but do not limit the scope of the invention.

Embodiment 1. A compound of the formula:

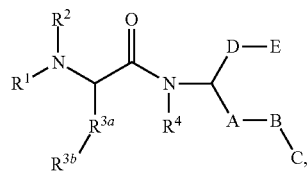

wherein:
A is alkylene that is unsubstituted or substituted, or a bond;
B is substituted or unsubstituted cycloalkylene, substituted or unsubstituted heterocycloalkylene, substituted arylene, substituted or unsubstituted heteroarylene that contains a sulfur atom as a ring member, or substituted or unsubstituted heteroarylene in which two ring members are heteroatoms and all other ring members of the heteroaryl are carbon atoms;
C is heterocycloalkyl, aryl, heteroaryl, alkyl, or cycloalkyl, any of which is unsubstituted or substituted, or hydrogen;
D is alkylene that is unsubstituted or substituted, or a bond;
E is cycloalkyl, heterocycloalkyl, aryl, or heteroaryl, any of which is unsubstituted or substituted;
$R^1$ is hydrogen, an acyl group, an alkoxycarbonyl group, an amidine group, or an amide group;
$R^2$ is alkyl, alkenyl, alkynyl, cycloalkyl, or cycloalkenyl, any of which is unsubstituted or substituted, or hydrogen;
$R^{3a}$ is alkylene that is unsubstituted or substituted, or a bond;
$R^{3b}$ is alkyl, alkenyl, alkynyl, cycloalkyl, cycloalkenyl, heterocycloalkyl, aryl, or heteroaryl, any of which is unsubstituted or substituted, or hydrogen; and
$R^4$ is alkyl, alkenyl, alkynyl, cycloalkyl, or cycloalkenyl, any of which is unsubstituted or substituted, or hydrogen;
wherein at least one of $R^2$ and $R^4$ is not hydrogen, or a pharmaceutically-acceptable salt or zwitterion thereof.

Embodiment 2. The compound of embodiment 1, wherein:
A is a bond;
B is heteroarylene that contains a sulfur atom as a ring member, or heteroarylene in which two ring members are heteroatoms and all other ring members of the heteroaryl are carbon atoms, any of which is unsubstituted or substituted;
C is aryl, heteroaryl, alkyl, or cycloalkyl, any of which is unsubstituted or substituted;
D is alkylene that is unsubstituted or substituted;
E is aryl or heteroaryl, any of which is unsubstituted or substituted;
$R^1$ is an acyl group or an alkoxycarbonyl group;
$R^2$ is alkyl that is substituted or unsubstituted, or hydrogen;
$R^{3a}$ is alkylene that is unsubstituted or substituted;
$R^{3b}$ is aryl or heteroaryl, any of which is unsubstituted or substituted; and
$R^4$ is alkyl that is substituted or unsubstituted, or hydrogen.

Embodiment 3. The compound of embodiment 1 or 2, wherein:
C is heteroaryl that is unsubstituted or substituted;
E is aryl that is unsubstituted or substituted; and
$R^1$ is an alkoxycarbonyl group.

Embodiment 4. The compound of any one of embodiments 1-3, wherein:
B is a thiazole group that is unsubstituted or substituted;
D is methylene;
$R^{3a}$ is methylene; and
$R^{3b}$ is aryl that is unsubstituted or substituted.

Embodiment 5. The compound of any one of embodiments 1-4, wherein:
B is a 2-substituted thiazol-4-yl group or a 4-substituted thiazol-2-yl group;
E is 4-substituted phenyl; and
$R^{3b}$ is phenyl.

Embodiment 6. The compound of any one of embodiments 1-5, wherein C is a thiophenyl group that is substituted or unsubstituted.

Embodiment 7. The compound of any one of embodiments 1-6, wherein C is a thiophen-2-yl group that is substituted or unsubstituted.

Embodiment 8. The compound of any one of embodiments 1-7, wherein $R^1$ is a methoxycarbonyl group.

Embodiment 9. The compound of any one of embodiments 1-8, wherein:
$R^2$ is methyl or hydrogen;
$R^4$ is methyl or hydrogen; and
wherein at least one of $R^2$ and $R^4$ is methyl.

Embodiment 10. The compound of any one of embodiments 1-9, wherein $R^2$ and $R^4$ are methyl.

Embodiment 11. The compound of any one of embodiments 1-9, wherein $R^2$ is hydrogen and $R^4$ is methyl.

Embodiment 12. The compound of any one of embodiments 1-9, wherein $R^2$ is methyl and $R^4$ is hydrogen.

Embodiment 13. The compound of any one of embodiments 1-12, wherein B is a 2-substituted thiazol-4-yl group.

Embodiment 14. The compound of any one of embodiments 1-13, wherein E is wherein:
X is methyl or hydrogen;
m is 0 or 1;
n is 0, 1, or 2; and
$R^5$ is hydrogen, hydroxyl, methyl, ethyl, phenyl, para-toluyl, N-piperidinyl, N-piperazinyl, N-pyrrolidinyl, $OR^6$, or $N(R^6)_2$, wherein each $R^6$ is independently hydrogen, methyl, ethyl, n-propyl, i-propyl, or n-butyl.

Embodiment 15. The compound of any one of embodiments 1-14, wherein:
X is hydrogen;
m is 1;
n is 2; and
$R^5$ is hydroxyl.

Embodiment 16. The compound of any one of embodiments 1-10, wherein the compound is:

Embodiment 17. The compound of any one of embodiments 1-9 or 11, wherein the compound is:

Embodiment 18. The compound of any one of embodiments 1-9 or 12, wherein the compound is:

Embodiment 19. A compound that activates Tie-2, wherein the compound that activates Tie-2 comprises a carbamate linkage of a secondary amine.

Embodiment 20. A compound that activates Tie-2, wherein the compound that activates Tie-2 comprises an amide linkage of a secondary amine and a carbamate linkage of a primary amine.

Embodiment 21. A compound that activates Tie-2, wherein the compound that activates Tie-2 comprises an amide linkage of a secondary amine and a carbamate linkage of another secondary amine.

Embodiment 22. A Tie-2 activator, wherein the Tie-2 activator has a solubility in water of at least 30 mg/mL at about 23° C.

Embodiment 23. The Tie-2 activator of embodiment 22, wherein the Tie-2 activator has a solubility in water of at least 50 mg/mL at about 23° C.

Embodiment 24. The Tie-2 activator of embodiment 22 or 23, wherein the Tie-2 activator has a solubility in water of at least 200 mg/mL at about 23° C.

What is claimed is:
1. A method of increasing cell survival, comprising administering to a patient in need thereof a therapeutically-effective amount of a compound of the formula:

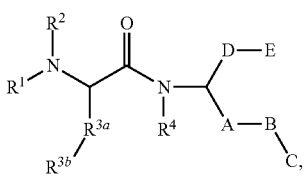

wherein:
A is alkylene that is unsubstituted or substituted, or a bond;
B is thiazole, which is unsubstituted or substituted;
C is thiophene, which is unsubstituted or substituted;
D is alkylene that is unsubstituted or substituted, or a bond;
E is phenyl, which is unsubstituted or substituted;
$R^1$ is hydrogen, an acyl group, an alkoxycarbonyl group, an amidine group, or an amide group;
$R^2$ is alkyl, alkenyl, alkynyl, cycloalkyl, or cycloalkenyl, any of which is unsubstituted or substituted, or hydrogen;
$R^{3a}$ is alkylene that is unsubstituted or substituted, or a bond;
$R^{3b}$ is alkyl, alkenyl, alkynyl, cycloalkyl, cycloalkenyl, heterocycloalkyl, aryl, or heteroaryl, any of which is unsubstituted or substituted, or hydrogen; and
$R^4$ is alkyl, alkenyl, alkynyl, cycloalkyl, or cycloalkenyl, any of which is unsubstituted or substituted,
or a pharmaceutically-acceptable salt or zwitterion thereof.

2. The method of claim 1, wherein:
A is a bond;
B is thiazole, which is unsubstituted or substituted;
C is thiophene;
D is alkylene that is unsubstituted or substituted;
E is phenyl, which is unsubstituted or substituted;
$R^1$ is an acyl group or an alkoxycarbonyl group;
$R^2$ is alkyl that is substituted or unsubstituted, or hydrogen;
$R^{3a}$ is alkylene that is unsubstituted or substituted;
$R^{3b}$ is aryl or heteroaryl, any of which is unsubstituted or substituted; and
$R^4$ is alkyl that is substituted or unsubstituted.

3. The method of claim 2, wherein:
C is thiophene;
E is phenyl that is unsubstituted or substituted; and
$R^1$ is an alkoxycarbonyl group.

4. The method of claim 3, wherein:
B is a thiazole;
D is methylene;
$R^{3a}$ is methylene; and
$R^{3b}$ is aryl that is unsubstituted or substituted.

5. The method of claim 4, wherein:
B is a thiazole;
E is 4-substituted phenyl; and
$R^{3b}$ is phenyl.

6. The method of claim 5, wherein $R^1$ is a methoxycarbonyl group.

7. The method of claim 6, wherein:
$R^2$ is methyl or hydrogen; and
$R^4$ is methyl.

8. The method of claim 7, wherein $R^2$ and $R^4$ are methyl.

9. The method of claim 7, wherein $R^2$ is hydrogen and $R^4$ is methyl.

10. The method of claim 7, wherein E is

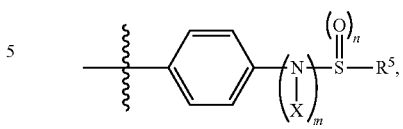

wherein:
X is methyl or hydrogen;
m is 0 or 1;
n is 0, 1, or 2; and
$R^5$ is hydrogen, hydroxyl, methyl, ethyl, phenyl, para-toluyl, N-piperidinyl, N-piperazinyl, N-pyrrolidinyl, $OR^6$, or $N(R^6)_2$, wherein each $R^6$ is independently hydrogen, methyl, ethyl, n-propyl, i-propyl, or n-butyl.

11. The method of claim 10, wherein:
X is hydrogen;
m is 1;
n is 2; and
$R^5$ is hydroxyl.

12. The method of claim 8, wherein the compound is:

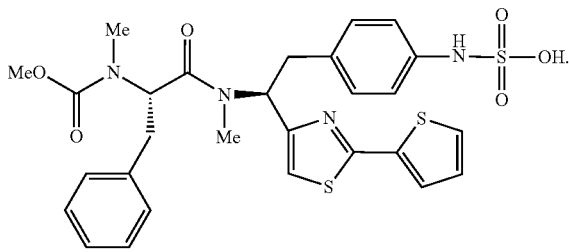 [SMILES: COC(=O)N(C)[C@@H](Cc1ccccc1)C(=O)N(C)[C@@H](Cc1ccc(NS(=O)(=O)O)cc1)c1csc(-c2cccs2)n1]

13. The method of claim 9, wherein the compound is:

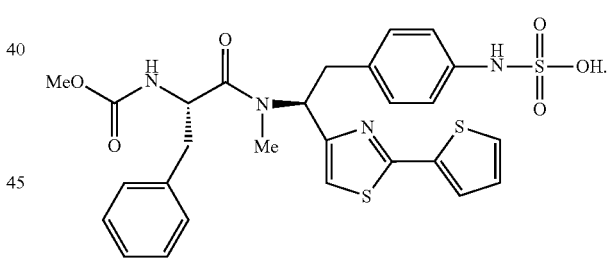

14. The method of claim 1, wherein administering the compound increases production of pAkt in the patient relative to the absence of administering the compound.

15. The method of claim 1, wherein the compound is administered by intravenous, intravitreal, subcutaneous, intramuscular, oral, rectal, aerosol, parenteral, ophthalmic, pulmonary, transdermal, vaginal, otic, nasal, or topical administration.

16. The method of claim 1, wherein the compound is administered in an amount of from about 1 mg to about 300 mg.

17. The method of claim 1, wherein the increase in cell survival is measured according to protein electrophoresis and blotting quantified by a percentage of density of signal of a sample blot band compared to a control blot band in a Phospho-Akt Activation Assay.

18. The method of claim 17, wherein the administration results in a signal of about 300% above the control.

19. A pharmaceutical composition comprising a compound of the formula:

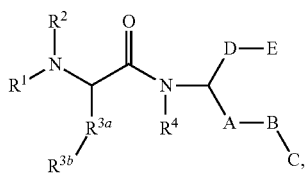

wherein:
A is alkylene that is unsubstituted or substituted, or a bond;
B is thiazole, which is unsubstituted or substituted;
C is thiophene, which is unsubstituted or substituted;
D is alkylene that is unsubstituted or substituted, or a bond;
E is phenyl, which is unsubstituted or substituted;
$R^1$ is hydrogen, an acyl group, an alkoxycarbonyl group, an amidine group, or an amide group;
$R^2$ is alkyl, alkenyl, alkynyl, cycloalkyl, or cycloalkenyl, any of which is unsubstituted or substituted, or hydrogen;
$R^{3a}$ is alkylene that is unsubstituted or substituted, or a bond;
$R^{3b}$ is alkyl, alkenyl, alkynyl, cycloalkyl, cycloalkenyl, heterocycloalkyl, aryl, or heteroaryl, any of which is unsubstituted or substituted, or hydrogen; and
$R^4$ is alkyl, alkenyl, alkynyl, cycloalkyl, or cycloalkenyl, any of which is unsubstituted or substituted,
or a pharmaceutically-acceptable salt or zwitterion thereof, and a pharmaceutically acceptable excipient.

20. The pharmaceutical composition of claim 19, wherein the pharmaceutical composition further comprises a carrier, stabilizer, diluent, dispersing agent, suspending agent, thickening agent, or one or more additional active ingredients.

21. The pharmaceutical composition of claim 20, wherein the additional active ingredients are selected from the group consisting of antimicrobial agents, anti-inflammatory agents, and anesthetics.

22. The pharmaceutical composition of claim 19, wherein the compound is selected from:

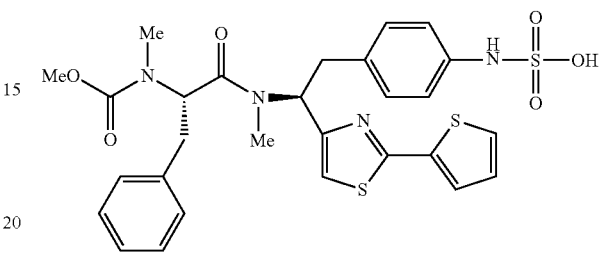

and

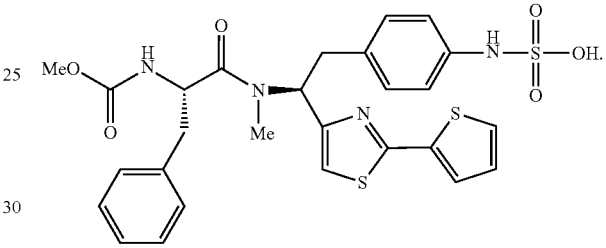

* * * * *